US009914958B2

(12) United States Patent
Wong et al.

(10) Patent No.: US 9,914,958 B2
(45) Date of Patent: Mar. 13, 2018

(54) NUCLEIC ACID-BASED LINKERS FOR DETECTING AND MEASURING INTERACTIONS

(71) Applicants: President and Fellows of Harvard College, Cambridge, MA (US); Children's Medical Center Corporation, Boston, MA (US)

(72) Inventors: Wesley Philip Wong, Cambridge, MA (US); Kenneth Anders Halvorsen, Glenmont, NY (US)

(73) Assignees: President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/356,282

(22) PCT Filed: Nov. 5, 2012

(86) PCT No.: PCT/US2012/063538
§ 371 (c)(1),
(2) Date: May 5, 2014

(87) PCT Pub. No.: WO2013/067489
PCT Pub. Date: May 10, 2013

(65) Prior Publication Data
US 2014/0255939 A1    Sep. 11, 2014

Related U.S. Application Data

(60) Provisional application No. 61/666,655, filed on Jun. 29, 2012, provisional application No. 61/556,194, filed on Nov. 5, 2011.

(51) Int. Cl.
*C12Q 1/68*    (2006.01)
*G01N 33/53*    (2006.01)

(52) U.S. Cl.
CPC .......... *C12Q 1/6816* (2013.01); *C12Q 1/6804* (2013.01); *C12Q 1/6813* (2013.01); *G01N 33/5308* (2013.01)

(58) Field of Classification Search
None
See application file for complete search history.

(56) References Cited

U.S. PATENT DOCUMENTS 5,571,677 A    11/1996 Gryaznov
5,635,352 A *    6/1997 Urdea ................. C12Q 1/6813
                                                                        435/6.1

(Continued)

FOREIGN PATENT DOCUMENTS

JP    H06-508753 A    10/1994
JP    2000-312589 A    11/2000

(Continued)

OTHER PUBLICATIONS

Bustamante et al., Entropic elasticity of lambda-phage DNA. Science. Sep. 9, 1994;265(5178):1599-600.

(Continued)

*Primary Examiner* — Betty J Forman
(74) *Attorney, Agent, or Firm* — Wolf, Greenfield & Sacks, P.C.

(57) ABSTRACT

The invention provides compositions comprising nucleic acid complexes for use in monitoring binding interactions and in measuring association and/or dissociation kinetics with or without force, detecting analytes, screening aptamers, and encoding/encrypting information. In some instances, the nucleic acid complexes are double-stranded nicked nucleic acids comprising a scaffold nucleic acid hybridized to one or more oligonucleotides. In some instances, a first and/or a second oligonucleotide are linked (Continued)

to moieties that are known to interact with each other or which are suspected of interacting with each other.

34 Claims, 19 Drawing Sheets

(56) References Cited

U.S. PATENT DOCUMENTS

| | | | |
|---|---|---|---|
| 5,902,724 A * | 5/1999 | Lane | C12Q 1/6804 435/6.19 |
| 6,251,660 B1 | 6/2001 | Muir et al. | |
| 8,491,454 B2 | 7/2013 | Wong et al. | |
| 8,795,143 B2 | 8/2014 | Wong et al. | |
| 2002/0177144 A1 | 11/2002 | Remacle et al. | |
| 2003/0143549 A1 | 7/2003 | Yang et al. | |
| 2007/0117109 A1 | 5/2007 | Rothemund | |
| 2007/0154899 A1 * | 7/2007 | Coull | C12Q 1/6818 435/6.12 |
| 2007/0155017 A1 | 7/2007 | Wyatt | |
| 2008/0312103 A1 | 12/2008 | Nemoto et al. | |
| 2009/0087838 A1 | 4/2009 | Reif et al. | |
| 2009/0286694 A1 | 11/2009 | Zainiev et al. | |
| 2010/0015608 A1 * | 1/2010 | Kolpashchikov | C12Q 1/6816 435/6.11 |
| 2010/0035247 A1 | 2/2010 | Burton | |
| 2010/0137120 A1 | 6/2010 | Wong et al. | |
| 2010/0206730 A1 | 8/2010 | Hunkapiller et al. | |
| 2010/0216658 A1 * | 8/2010 | Chaput | B01J 19/0046 506/9 |
| 2011/0086774 A1 * | 4/2011 | Dunaway | G01N 33/6803 506/9 |
| 2011/0268654 A1 | 11/2011 | Hilderbrand et al. | |
| 2012/0058008 A1 | 3/2012 | Corbett et al. | |
| 2013/0004523 A1 | 1/2013 | Zubarev et al. | |
| 2013/0130884 A1 | 5/2013 | Wong et al. | |
| 2013/0196341 A1 | 8/2013 | Neely et al. | |
| 2013/0225429 A1 | 8/2013 | Curry | |
| 2013/0310260 A1 | 11/2013 | Kim et al. | |
| 2013/0344508 A1 | 12/2013 | Schwartz et al. | |
| 2014/0284213 A1 | 9/2014 | Sabin et al. | |
| 2015/0027894 A1 | 1/2015 | Puleo et al. | |
| 2015/0099650 A1 | 4/2015 | Snood et al. | |
| 2015/0361422 A1 | 12/2015 | Sampson et al. | |

FOREIGN PATENT DOCUMENTS

| | | |
|---|---|---|
| JP | 2003-219897 A | 8/2003 |
| JP | 2005-536234 A | 12/2005 |
| JP | 2008-259453 A | 10/2008 |
| JP | 2009-521230 | 6/2009 |
| WO | WO 93/01313 A1 | 1/1993 |
| WO | WO2000/40751 * | 7/2000 |
| WO | WO 2004/016767 A2 | 2/2004 |
| WO | WO 2007/076128 A2 | 7/2007 |
| WO | WO 2011/005221 A1 | 1/2011 |
| WO | WO 2011/153211 A1 | 12/2011 |
| WO | WO 2014/011800 A1 | 1/2014 |
| WO | WO 2015/006626 A1 | 1/2015 |
| WO | WO 2016/089588 A1 | 6/2016 |
| WO | WO 2017/003950 A2 | 1/2017 |

OTHER PUBLICATIONS

Bustamante et al.,Ten years of tension: single-molecule DNA mechanics. Nature. Jan. 23, 2003;421(6921):423-7.
Chilkoti et al., Molecular Origins of the Slow Streptavidin-Biotin Dissociation Kinetics. J Am Chem Soc. 1995;117(43):10622-8.
Chivers et al., A streptavidin variant with slower biotin dissociation and increased mechanostability. Nat Methods. May 2010;7(5):391-3. doi: 10.1038/nmeth.1450. Epub Apr. 11, 2010.
Deniz et al., Single-molecule biophysics: at the interface of biology, physics and chemistry. J R Soc Interface. Jan. 6, 2008;5(18):15-45.
Douglas et al., Self-assembly of DNA into nanoscale three-dimensional shapes. Nature. May 21, 2009;459(7245):414-8. doi: 10.1038/nature08016.
Evans et al., Dynamic strength of molecular adhesion bonds. Biophys J. Apr. 1997;72(4):1541-55.
Evans et al., Forces and bond dynamics in cell adhesion. Science. May 25, 2007;316(5828):1148-53.
Evans. Probing the relation between force—lifetime—and chemistry in single molecular bonds. Annu Rev Biophys Biomol Struct. 2001;30:105-28.
França et al., A review of DNA sequencing techniques. Q Rev Biophys. May 2002;35(2):169-200.
Green, Avidin and streptavidin. Methods Enzymol. 1990;184:51-67.
Greenleaf et al., High-resolution, single-molecule measurements of biomolecular motion. Annu Rev Biophys Biomol Struct. 2007;36:171-90.
Halvorsen et al., Massively Parallel Single-Molecule Manipulation Using Centrifugal Force. Biophys J. Jun. 2, 2010;98(11):L53-5.
Halvorsen, Probing Weak Single-Molecule Interactions: Development and Demonstration of a New Instrument. Boston University, College of Engineering dissertation. 2007: 102 pages.
Hanke et al., Entropy loss in long-distance DNA looping. Biophys J. Jul. 2003;85(1):167-73.
Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.
Khalil et al., Single M13 bacteriophage tethering and stretching. Proc Natl Acad Sci U S A. Mar. 20, 2007;104(12):4892-7. Epub Mar. 13, 2007.
Klumb et al., Energetic roles of hydrogen bonds at the ureido oxygen binding pocket in the streptavidin-biotin complex. Biochemistry. May 26, 1998;37(21):7657-63.
Kufer et al., Single-molecule cut-and-paste surface assembly. Science. Feb. 1, 2008;319(5863):594-6. doi:10.1126/science.1151424.
Neuman et al., Single-molecule force spectroscopy: optical tweezers, magnetic tweezers and atomic force microscopy. Nat Methods. Jun. 2008;5(6):491-505. doi: 10.1038/nmeth.1218.
Quek et al., Mechanically controlled binary conductance switching of a single-molecule junction. Nat Nanotechnol. Apr. 2009;4(4):230-4. doi:10.1038/nnano.2009.10. Epub Mar. 1, 2009.
Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.
Rothemund, Folding DNA to create nanoscale shapes and patterns. Nature. Mar. 16, 2006;440(7082):297-302.
Shroff et al., Biocompatible force sensor with optical readout and dimensions of 6 nm3. Nano Lett. Jul. 2005;5(7):1509-14.
Shroff et al., Optical measurement of mechanical forces inside short DNA loops. Biophys J. Mar. 15, 2008;94(6):2179-86. Epub Dec. 7, 2007.
Smith et al., Overstretching B-DNA: the elastic response of individual double-stranded and single-stranded DNA molecules. Science. Feb. 9, 1996;271(5250):795-9.
Strunz et al., Dynamic force spectroscopy of single DNA molecules. Proc Natl Acad Sci U S A. Sep. 28, 1999;96(20):11277-82.
Svoboda et al., Direct observation of kinesin stepping by optical trapping interferometry. Nature. Oct. 21, 1993;365(6448):721-7.
Wong et al., The effect of integration time on fluctuation measurements: calibrating an optical trap in the presence of motion blur. Opt Express. Dec. 11, 2006;14(25):12517-31.
Zhang et al., Mechanoenzymatic cleavage of the ultralarge vascular protein, von Willebrand Factor. Science. Jun. 5, 2009;324(5932):1330-4.
International Search Report and Written Opinion for PCT/US2012/063538 dated Mar. 15, 2013.
International Preliminary Report on Patentability for PCT/US2012/063538 dated May 15, 2014.
Halvorsen et al., Binary DNA nanostructures for data encryption. PLoS One. 2012;7(9):e44212. doi: 10.1371/journal.pone.0044212. Epub Sep. 11, 2012.

(56) References Cited

OTHER PUBLICATIONS

Halvorsen et al., Nanoengineering a single-molecule mechanical switch using DNA self-assembly. Nanotechnology. Dec. 9, 2011;22(49):494005. doi: 10.1088/0957-4484/22/49/494005. Epub Nov. 21, 2011.

Kim et al., A mechanically stabilized receptor-ligand flex-bond important in the vasculature. Nature. Aug. 19, 2010;466(7309):992-5. doi: 10.1038/nature09295.

Leier et al., Cryptography with DNA binary strands. Biosystems. Jun. 2000;57(1):13-22.

Wiita et al., Force-dependent chemical kinetics of disulfide bond reduction observed with single-molecule techniques. Proc Natl Acad Sci U S A. May 9, 2006;103(19):7222-7. Epub Apr. 27, 2006.

Aaij et al., The gel electrophoresis of DNA. Biochim Biophys Acta. May 10, 1972;269(2):192-200.

Baumann et al., Ionic effects on the elasticity of single DNA molecules. Proc Natl Acad Sci U S A. Jun. 10, 1997;94(12):6185-90.

Bellot et al., Recovery of intact DNA nanostructures after agarose gel-based separation. Nat Methods. Mar. 2011;8(3):192-4. doi: 10.1038/nmeth0311-192.

Bishop et al., Electrophoretic separation of viral nucleic acids on polyacrylamide gels. J Mol Biol. Jun. 28, 1967;26(3):373-87.

Chandrasekaran et al., Label-free Detection of Specific Nucleic Acid Sequences using DNA Nanoswitches. The NRA Institute, University at Albany, State University of New York.

Chandrasekaran et al., Programmable DNA Nanoswitches for Detection of Nucleic Acid Sequences. ACS Sens., 2016, 1 (2), pp. 120-123.

Douglas et al., A logic-gated nanorobot for targeted transport of molecular payloads. Science. Feb. 17, 2012;335(6070):831-4. doi: 10.1126/science.1214081.

Fazio et al., DNA curtains and nanoscale curtain rods: high-throughput tools for single molecule imaging. Langmuir. Sep. 16, 2008;24(18):10524-31. doi: 10.1021/la801762h. Epub Aug. 7, 2008.

Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.

Hassur et al., UV shadowing—a new and convenient method for the location of ultraviolet-absorbing species in polyacrylamide gels. Anal Biochem. May 1974;59(1):162-4.

Hellman et al., Electrophoretic mobility shift assay (EMSA) for detecting protein-nucleic acid interactions. Nat Protoc. 2007;2(8):1849-61.

Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.

Jones et al, Nanomaterials. Programmable materials and the nature of the DNA bond. Science. Feb. 20, 2015;347(6224):1260901. doi: 10.1126/science.1260901.

Kim et al., Multiplexed single-molecule assay for enzymatic activity on flow-stretched DNA. Nat Methods. May 2007;4(5):397-9. Epub Apr. 15, 2007.

Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.

Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.

McDonell et al., Analysis of restriction fragments of T7 DNA and determination of molecular weights by electrophoresis in neutral and alkaline gels. J Mol Biol. Feb. 15, 1977;110(1):119-46.

Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.

Nelson et al., Tethered particle motion as a diagnostic of DNA tether length. J Phys Chem B. Aug. 31, 2006;110(34):17260-7. Abstract only.

Pei et al, A DNA nanostructure-based biomolecular probe carrier platform for electrochemical biosensing. Adv Mater. Nov. 9, 2010;22(42):4754-8. doi: 10.1002/adma.201002767.

Rief et al., Sequence-dependent mechanics of single DNA molecules. Nat Struct Biol. Apr. 1999;6(4):346-9.

Sacca et al., DNA origami: the art of folding DNA. Angew Chem Int Ed Engl. Jan. 2, 2012;51(1):58-66. doi: 10.1002/anie.201105846. Epub Dec. 7, 2011.

Seeman, Nanomaterials based on DNA. Annu Rev Biochem. 2010;79:65-87. doi: 10.1146/annurev-biochem-060308-102244.

Seeman, DNA in a material world. Nature. Jan. 23, 2003;421(6921):427-31.

Thorne, Electrophoretic separation of polyoma virus DNA from host cell DNA. Virology. Jun. 1966;29(2):234-9.

Thuring et al., A freeze-squeeze method for recovering long DNA from agarose gels. Anal Biochem. May 26, 1975;66(1):213-20.

Williams et al., Entropy and heat capacity of DNA melting from temperature dependence of single molecule stretching. Biophys J. Apr. 2001;80(4):1932-9.

Winfree et al., Design and self-assembly of two-dimensional DNA crystals. Nature. Aug. 6, 1998;394(6693):539-44.

Zadeh et al., NUPACK: Analysis and design of nucleic acid systems. J Comput Chem. Jan. 15, 2011;32(1):170-3. doi: 10.1002/jcc.21596.

Zheng et al., From molecular to macroscopic via the rational design of a self-assembled 3D DNA crystal. Nature. Sep. 3, 2009;461(7260):74-7. doi: 10.1038/nature08274.

Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.

Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.

Doshi et al., In vitro nanobody discovery for integral membrane protein targets. Sci Rep. Oct. 24, 2014;4:6760. doi: 10.1038/srep06760.

Park et al., Dual blockade of cyclic AMP response element—(CRE) and AP-1-directed transcription by CRE-transcription factor decoy oligonucleotide. gene-specific inhibition of tumor growth. J Biol Chem. Jan. 15, 1999;274(3):1573-80.

* cited by examiner

121 Plain oligos spanning the entire M13 template

```
001  AACATCCAATAAATCATACAGGCAAGGCAAAGAATTAGCAAAATTAAGCAATAAAGCCTC
002  AGAGCATAAAGCTAAATCGGTTGTACCAAAAACATTATGACCCTGTAATACTTTTGCGGG
003  AGAAGCCTTTATTTCAACGCAAGGATAAAAATTTTTAGAACCCTCATATATTTTAAATGC
004  AATGCCTGAGTAATGTGTAGGTAAAGATTCAAAAGGGTGAGAAAGGCCGGAGACAGTCAA
005  ATCACCATCAATATGATATTCAACCGTTCTAGCTGATAAATTAATGCCGGAGAGGGTAGC
006  TATTTTTGAGAGATCTACAAAGGCTATCAGGTCATTGCCTGAGAGTCTGGAGCAAACAAG
007  AGAATCGATGAACGGTAATCGTAAAACTAGCATGTCAATCATATGTACCCCGGTTGATAA
008  TCAGAAAAGCCCCAAAAACAGGAAGATTGTATAAGCAAATATTTAAATTGTAAACGTTAA
009  TATTTTGTTAAAATTCGCATTAAATTTTTGTTAAATCAGCTCATTTTTTAACCAATAGGA
010  ACGCCATCAAAAATAATTCGCGTCTGGCCTTCCTGTAGCCAGCTTTCATCAACATTAAAT
011  GTGAGCGAGTAACAACCCGTCGGATTCTCCGTGGGAACAAACGGCGGATTGACCGTAATG
012  GGATAGGTCACGTTGGTGTAGATGGGCGCATCGTAACCGTGCATCTGCCAGTTTGAGGGG
013  ACGACGACAGTATCGGCCTCAGGAAGATCGCACTCCAGCCAGCTTTCCGGCACCGCTTCT
014  GGTGCCGGAAACCAGGCAAAGCGCCATTCGCCATTCAGGCTGCGCAACTGTTGGGAAGGG
015  CGATCGGTGCGGGCCTCTTCGCTATTACGCCAGCTGGCGAAAGGGGGATGTGCTGCAAGG
016  CGATTAAGTTGGGTAACGCCAGGGTTTTCCCAGTCACGACGTTGTAAAACGACGGCCAGT
017  GCCAAGCTTGCATGCCTGCAGGTCGACTCTAGAGGATCCCCGGGTACCGAGCTCGAATTC
018  GTAATCATGGTCATAGCTGTTTCCTGTGTGAAATTGTTATCCGCTCACAATTCCACACAA
019  CATACGAGCCGGAAGCATAAAGTGTAAAGCCTGGGGTGCCTAATGAGTGAGCTAACTCAC
020  ATTAATTGCGTTGCGCTCACTGCCCGCTTTCCAGTCGGGAAACCTGTCGTGCCAGCTGCA
021  TTAATGAATCGGCCAACGCGCGGGGAGAGGCGGTTTGCGTATTGGGCGCCAGGGTGGTTT
022  TTCTTTTCACCAGTGAGACGGGCAACAGCTGATTGCCCTTCACCGCCTGGCCCTGAGAGA
023  GTTGCAGCAAGCGGTCCACGCTGGTTTGCCCCAGCAGGCGAAAATCCTGTTTGATGGTGG
024  TTCCGAAATCGGCAAAATCCCTTATAAATCAAAAGAATAGCCCGAGATAGGGTTGAGTGT
025  TGTTCCAGTTTGGAACAAGAGTCCACTATTAAAGAACGTGGACTCCAACGTCAAAGGGCG
026  AAAAACCGTCTATCAGGGCGATGGCCCACTACGTGAACCATCACCCAAATCAAGTTTTTT
027  GGGGTCGAGGTGCCGTAAAGCACTAAATCGGAACCCTAAAGGGAGCCCCCGATTTAGAGC
028  TTGACGGGGAAAGCCGGCGAACGTGGCGAGAAAGGAAGGGAAGAAAGCGAAAGGAGCGGG
029  CGCTAGGGCGCTGGCAAGTGTAGCGGTCACGCTGCGCGTAACCACCACACCCGCCGCGCT
030  TAATGCGCCGCTACAGGGCGCGTACTATGGTTGCTTTGACGAGCACGTATAACGTGCTTT
031  CCTCGTTAGAATCAGAGCGGGAGCTAAACAGGAGGCCGATTAAAGGGATTTTAGACAGGA
032  ACGGTACGCCAGAATCCTGAGAAGTGTTTTTATAATCAGTGAGGCCACCGAGTAAAAGAG
033  TCTGTCCATCACGCAAATTAACCGTTGTAGCAATACTTCTTTGATTAGTAATAACATCAC
034  TTGCCTGAGTAGAAGAACTCAAACTATCGGCCTTGCTGGTAATATCCAGAACAATATTAC
035  CGCCAGCCATTGCAACAGGAAAAACGCTCATGGAAATACCTACATTTTGACGCTCAATCG
036  TCTGAAATGGATTATTTACATTGGCAGATTCACCAGTCACACGACCAGTAATAAAAGGGA
037  CATTCTGGCCAACAGAGATAGAACCCTTCTGACCTGAAAGCGTAAGAATACGTGGCACAG
038  ACAATATTTTGAATGGCTATTAGTCTTTAATGCGCGAACTGATAGCCCTAAAACATCGC
039  CATTAAAAATACCGAACGAACCACCAGCAGAAGATAAAACAGAGGTGAGGCGGTCAGTAT
040  TAACACCGCCTGCAACAGTGCCACGCTGAGAGCCAGCAGCAAATGAAAAATCTAAAGCAT
041  CACCTTGCTGAACCTCAAATATCAAACCCTCAATCAATATCTGGTCAGTTGGCAAATCAA
042  CAGTTGAAAGGAATTGAGGAAGGTTATCTAAAATATCTTTAGGAGCACTAACAACTAATA
043  GATTAGAGCCGTCAATAGATAATACATTTGAGGATTTAGAAGTATTAGACTTTACAAACA
044  ATTCGACAACTCGTATTAAATCCTTTGCCCGAACGTTATTAATTTTAAAAGTTTGAGTAA
045  CATTATCATTTTGCGGAACAAAGAAACCACCAGAAGGAGCGGAATTATCATCATATTCCT
```

Fig. 1A-1

046 GATTATCAGATGATGGCAATTCATCAATATAATCCTGATTGTTTGGATTATACTTCTGAA
047 TAATGGAAGGGTTAGAACCTACCATATCAAAATTATTTGCACGTAAAACAGAAATAAAGA
048 AATTGCGTAGATTTTCAGGTTTAACGTCAGATGAATATACAGTAACAGTACCTTTTACAT
049 CGGGAGAAACAATAACGGATTCGCCTGATTGCTTTGAATACCAAGTTACAAAATCGCGCA
050 GAGGCGAATTATTCATTTCAATTACCTGAGCAAAAGAAGATGATGAAACAAACATCAAGA
051 AAACAAAATTAATTACATTTAACAATTTCATTTGAATTACCTTTTTTAATGGAAACAGTA
052 CATAAATCAATATATGTGAGTGAATAACCTTGCTTCTGTAAATCGTCGCTATTAATTAAT
053 TTTCCCTTAGAATCCTTGAAAACATAGCGATAGCTTAGATTAAGACGCTGAGAAGAGTCA
054 ATAGTGAATTTATCAAAATCATAGGTCTGAGAGACTACCTTTTTAACCTCCGGCTTAGGT
055 TGGGTTATATAACTATATGTAAATGCTGATGCAAATCCAATCGCAAGACAAAGAACGCGA
056 GAAAACTTTTTCAAATATATTTTAGTTAATTTCATCTTCTGACCTAAATTTAATGGTTTG
057 AAATACCGACCGTGTGATAAATAAGGCGTTAAATAAGAATAAACACCGGAATCATAATTA
058 CTAGAAAAAGCCTGTTTAGTATCATATGCGTTATACAAATTCTTACCAGTATAAAGCCAA
059 CGCTCAACAGTAGGGCTTAATTGAGAATCGCCATATTTAACAACGCCAACATGTAATTTA
060 GGCAGAGGCATTTTCGAGCCAGTAATAAGAGAATATAAAGTACCGACAAAAGGTAAAGTA
061 ATTCTGTCCAGACGACGACAATAAACAACATGTTCAGCTAATGCAGAACGCGCCTGTTTA
062 TCAACAATAGATAAGTCCTGAACAAGAAAAATAATATCCCATCCTAATTTACGAGCATGT
063 AGAAACCAATCAATAATCGGCTGTCTTTCCTTATCATTCCAAGAACGGGTATTAAACCAA
064 GTACCGCACTCATCGAGAACAAGCAAGCCGTTTTTATTTTCATCGTAGGAATCATTACCG
065 CGCCCAATAGCAAGCAAATCAGATATAGAAGGCTTATCCGGTATTCTAAGAACGCGAGGC
066 GTTTTAGCGAACCTCCCGACTTGCGGGAGGTTTTGAAGCCTTAAATCAAGATTAGTTGCT
067 ATTTTGCACCCAGCTACAATTTTATCCTGAATCTTACCAACGCTAACGAGCGTCTTTCCA
068 GAGCCTAATTTGCCAGTTACAAAATAAACAGCCATATTATTTATCCCAATCCAAATAAGA
069 AACGATTTTTTGTTTAACGTCAAAAATGAAAATAGCAGCCTTTACAGAGAGAATAACATA
070 AAAACAGGGAAGCGCATTAGACGGGAGAATTAACTGAACACCCTGAACAAAGTCAGAGGG
071 TAATTGAGCGCTAATATCAGAGAGATAACCCACAAGAATTGAGTTAAGCCCAATAATAAG
072 AGCAAGAAACAATGAAATAGCAATAGCTATCTTACCGAAGCCCTTTTTAAGAAAAGTAAG
073 CAGATAGCCGAACAAAGTTACCAGAAGGAAACCGAGGAAACGCAATAATAACGGAATACC
074 CAAAAGAACTGGCATGATTAAGACTCCTTATTACGCAGTATGTTAGCAAACGTAGAAAAT
075 ACATACATAAAGGTGGCAACATATAAAAGAAACGCAAAGACACCACGGAATAAGTTTATT
076 TTGTCACAATCAATAGAAAATTCATATGGTTTACCAGCGCCAAAGACAAAAGGGCGACAT
077 TCAACCGATTGAGGGAGGGAAGGTAAATATTGACGGAAATTATTCATTAAAGGTGAATTA
078 TCACCGTCACCGACTTGAGCCATTTGGGAATTAGAGCCAGCAAAATCACCAGTAGCACCA
079 TTACCATTAGCAAGGCCGGAAACGTCACCAATGAAACCATCGATAGCAGCACCGTAATCA
080 GTAGCGACAGAATCAAGTTTGCCTTTAGCGTCAGACTGTAGCGCGTTTTCATCGGCATTT
081 TCGGTCATAGCCCCCTTATTAGCGTTTGCCATCTTTTCATAATCAAAATCACCGGAACCA
082 GAGCCACCACCGGAACCGCCTCCCTCAGAGCCGCCACCCTCAGAACCGCCACCCTCAGAG
083 CCACCACCCTCAGAGCCGCCACCAGAACCACCACCAGAGCCGCCGCCAGCATTGACAGGA
084 GGTTGAGGCAGGTCAGACGATTGGCCTTGATATTCACAAACAAATAAATCCTCATTAAAG
085 CCAGAATGGAAAGCGCAGTCTCTGAATTTACCGTTCCAGTAAGCGTCATACATGGCTTTT
086 GATGATACAGGAGTGTACTGGTAATAAGTTTTAACGGGGTCAGTGCCTTGAGTAACAGTG
087 CCCGTATAAACAGTTAATGCCCCCTGCCTATTTCGGAACCTATTATTCTGAAACATGAAA
088 GTATTAAGAGGCTGAGACTCCTCAAGAGAAGGATTAGGATTAGCGGGGTTTTGCTCAGTA
089 CCAGGCGGATAAGTGCCGTCGAGAGGGTTGATATAAGTATAGCCCGGAATAGGTGTATCA
090 CCGTACTCAGGAGGTTTAGTACCGCCACCCTCAGAACCGCCACCCTCAGAACCGCCACCC

Fig. 1A-2

091 TCAGAGCCACCACCCTCATTTTCAGGGATAGCAAGCCCAATAGGAACCCATGTACCGTAA
092 CACTGAGTTTCGTCACCAGTACAAACTACAACGCCTGTAGCATTCCACAGACAGCCCTCA
093 TAGTTAGCGTAACGATCTAAAGTTTTGTCGTCTTTCCAGACGTTAGTAAATGAATTTTCT
094 GTATGGGATTTTGCTAAACAACTTTCAACAGTTTCAGCGGAGTGAGAATAGAAAGGAACA
095 ACTAAAGGAATTGCGAATAATAATTTTTTCACGTTGAAAATCTCCAAAAAAAAGGCTCCA
096 AAAGGAGCCTTTAATTGTATCGGTTTATCAGCTTGCTTTCGAGGTGAATTTCTTAAACAG
097 CTTGATACCGATAGTTGCGCCGACAATGACAACAACCATCGCCCACGCATAACCGATATA
098 TTCGGTCGCTGAGGCTTGCAGGGAGTTAAAGGCCGCTTTTGCGGGATCGTCACCCTCAGC
099 AGCGAAAGACAGCATCGGAACGAGGGTAGCAACGGCTACAGAGGCTTTGAGGACTAAAGA
100 CTTTTTCATGAGGAAGTTTCCATTAAACGGGTAAAATACGTAATGCCACTACGAAGGCAC
101 CAACCTAAAACGAAAGAGGCAAAAGAATACACTAAAACACTCATCTTTGACCCCCAGCGA
102 TTATACCAAGCGCGAAACAAAGTACAACGGAGATTTGTATCATCGCCTGATAAATTGTGT
103 CGAAATCCGCGACCTGCTCCATGTTACTTAGCCGGAACGAGGCGCAGACGGTCAATCATA
104 AGGGAACCGAACTGACCAACTTTGAAAGAGGACAGATGAACGGTGTACAGACCAGGCGCA
105 TAGGCTGGCTGACCTTCATCAAGAGTAATCTTGACAAGAACCGGATATTCATTACCCAAA
106 TCAACGTAACAAAGCTGCTCATTCAGTGAATAAGGCTTGCCCTGACGAGAAACACCAGAA
107 CGAGTAGTAAATTGGGCTTGAGATGGTTTAATTTCAACTTTAATCATTGTGAATTACCTT
108 ATGCGATTTTAAGAACTGGCTCATTATACCAGTCAGGACGTTGGGAAGAAAAATCTACGT
109 TAATAAAACGAACTAACGGAACAACATTATTACAGGTAGAAAGATTCATCAGTTGAGATT
110 TAGGAATACCACATTCAACTAATGCAGATACATAACGCCAAAAGGAATTACGAGGCATAG
111 TAAGAGCAACACTATCATAACCCTCGTTTACCAGACGACGATAAAAACCAAAATAGCGAG
112 AGGCTTTTGCAAAAGAAGTTTTGCCAGAGGGGGTAATAGTAAAATGTTTAGACTGGATAG
113 CGTCCAATACTGCGGAATCGTCATAAATATTCATTGAATCCCCCTCAAATGCTTTAAACA
114 GTTCAGAAAACGAGAATGACCATAAATCAAAAATCAGGTCTTTACCCTGACTATTATAGT
115 CAGAAGCAAAGCGGATTGCATCAAAAAGATTAAGAGGAAGCCCGAAAGACTTCAAATATC
116 GCGTTTTAATTCGAGCTTCAAAGCGAACCAGACCGGAAGCAAACTCCAACAGGTCAGGAT
117 TAGAGAGTACCTTTAATTGCTCCTTTTGATAAGAGGTCATTTTGCGGATGGCTTAGAGC
118 TTAATTGCTGAATATAATGCTGTAGCTCAACATGTTTTAAATATGCAACTAAAGTACGGT
119 GTCTGGAAGTTTCATTCCATATAACAGTTGATTCCCAATTCTGCGAACGAGTAGATTTAG
120 TTTGACCATTAGATACATTTCGCAAATGGTCAATAACCTGTTTAGCTATATTTTCATTTG
121 GGGCGCGAGCTGAAAAGGTGGCATCAATTCTACTAATAGTAGTAGCATT

Oligo for M13 linearization
000A CTACTAATAGTAGTAGCATTAACATCCAATAAATCATACA BtsCI cut site oligo

Labeled oligos
001A 5' dual biotin - AACATCCAATAAATCATACAGGCAAGGCAAAGAATTAGCAAAATTAAGCAATAAAGCCTC
033A TCTGTCCATCACGCAAATTAACCGTTGTAGCAATACTTCTTTGATTAGTAATAACATCAC - 3'thiol
044A 5' dig - ATTCGACAACTCGTATTAAATCCTTTGCCCGAACGTTATTAATTTTAAAAGTTTGAGTAA
121A GGGCGCGAGCTGAAAAGGTGGCATCAATTCTACTAATAGTAGTAGCATT - dT internal biotin 3' biotin

Fig. 1A-3

NUCLEIC ACID-BASED LINKERS FOR DETECTING AND MEASURING INTERACTIONS

RELATED APPLICATIONS

This application is a national stage filing under 35 U.S.C. § 371 of International Application No. PCT/US2012/063538 filed Nov. 5, 2012, which was published under PCT Article 21(2) in English, and which claims the benefit under 35 U.S.C. § 119(e) of U.S. provisional application Ser. No. 61/556,194, filed Nov. 5, 2011 and U.S. provisional application Ser. No. 61/666,655, filed Jun 29, 2012, each of which is incorporated by reference herein in its entirety.

BACKGROUND OF INVENTION

The ability to precisely manipulate individual molecules has led to stunning new discoveries in physics, biology, and medicine (Deniz A. A. et al. (2008) J. R. Soc. Interface, 5: 15; Ritort F. et al. (2006) J. Phys.: Condens. Matter 18: R531), as well as powerful new methods in nanoscale engineering. For example, single-molecule force measurements have revealed the basic mechanical properties of nucleic acids (Bustamante C. et al. Nature 421: 423-7), the dynamics and functioning of molecular motors (Svoboda K. et al. (1993) Nature 365: 721-7; Greenleaf W. J. et al. (2007) Annu. Rev. Biophys. Biomol. Struct. 36: 171), and the role of hydrodynamic forces in the circulatory system in regulating enzymatic activity (Zhang X. et al. (2009) Science 324: 1330). In addition, these measurements have yielded fundamental insights into the dynamical strength of molecular interactions (Evans E. (2001) Annu. Rev. Biophys. Biomol. Struct. 30: 105-28), which have led to the development of creative new tools for nanoscale assembly (Kufer S. K. et al. (2008) Science 319: 594).

Mechanical forces can be applied to individual molecules using a broad range of tools, including optical traps, magnetic tweezers, mechanical cantilevers, and the centrifuge force microscope (Neuman K. C. et al. (2008) Nature Methods 5: 491-505; Halvorsen K. et al. (2010) Biophys. J. 98: L53-5). Yet a common requirement of these methods is that single-molecule constructs must be specifically tethered between two surfaces (e.g., beads, cover slips or cantilevers) to enable their manipulation and detection. This leads to one of the major challenges in single-molecule experimentation—verifying that exactly one molecular tether is being pulled, and distinguishing this tether from non-specific and unintended interactions that may occur (e.g., surface-surface interactions, formation of multiple bonds). The success and reliability of single-molecule experiments depends upon the creation of reliable, verifiable and robust linking techniques. This is particularly important for bond rupture studies (e.g., characterizing the strength of molecular adhesion bonds (Evans E. et al. (1997) Biophys. J. 72: 1541-55), DNA base pairing (Strunz T. et al. Proc. Natl Acad. Sci. 96: 11277), and cell adhesion and signaling (Evans E. A. et al. (2007) Science 316: 1148)), as the dissociation between two molecules can be difficult to positively identify due to the lack of an obvious mechanical signature.

SUMMARY OF INVENTION

The invention provides, inter alia, compositions comprising a switchable single-molecule linker comprised of two members of a binding pair, such as a receptor and a ligand, integrated onto a nucleic acid (e.g., DNA backbone), methods of making such linkers, and methods of using such linkers, including for example in single-molecule force studies and as molecular on-rate or off-rate sensors using, for example, standard gel electrophoresis.

The ability to manipulate and observe single biological molecules has led to both fundamental scientific discoveries and new methods in nanoscale engineering. A common challenge in many single-molecule experiments is reliably linking molecules to surfaces and identifying and monitoring their interactions. The invention overcomes this challenge by providing a novel nano-engineered nucleic acid based linker (e.g., a DNA-based linker) that behaves as a force-activated switch, providing a molecular signature that can eliminate errant data arising from non-specific and multiple interactions.

It is to be understood that, for convenience, the invention may refer to the linker of the invention as being "DNA-based". These recitations are not to be construed as limiting the nature of the linker to solely DNA. Accordingly, the DNA-based compositions of the invention are to be construed as exemplary embodiments of the nucleic acid based compositions of the invention.

By integrating both members of a binding pair, such as a receptor and a ligand, into a single piece of DNA using for example DNA self-assembly, a single tether can be positively identified by force-extension behavior, and binding pair interactions, such as receptor-ligand binding and unbinding, can be easily identified by a sudden changes in tether length. Additionally, under proper conditions the exact same pair of molecules can be repeatedly bound and unbound. The approach is simple, versatile and modular, and can be easily implemented using standard commercial reagents and laboratory equipment. In addition to improving the reliability and accuracy of force measurements, this single-molecule mechanical switch paves the way for high-throughput serial measurements, high-throughput identification of binding partners for targets of interest, single-molecule on-rate and off-rate studies, investigations of population heterogeneity, detection of analytes in samples and diagnostic applications relating thereto, and encoding systems for encrypting and decrypting information, among other things.

As an example, the linker of the invention, which is referred to herein interchangeably as a nucleic acid complex, may be used as a molecular off-rate (and possibly on-rate) sensor. It was discovered that the two states of the linker (which may be referred to herein as the bound and unbound states or the closed and open states) migrate differently on a standard electrophoresis gel, giving a direct measure of the percentage of bound and unbound product. The following protocol can then be used to measure the off-rate between the receptor and ligand: 1) create stock of linker molecule, 2) add excess ligand or receptor to force all unbound linkers to remain unbound, 3) use a crosslinking agent (e.g., photoactive crosslinker) to "freeze" the bound product at different times, 4) run a gel and measure the decrease in bound products over time. This has been demonstrated successfully, inter alia, where the receptor and ligand are opposite DNA strands that hybridize to each other, and for antigen and antibody binding.

Accordingly, in one aspect, the invention provides a nucleic acid complex comprising a single-stranded scaffold nucleic acid hybridized to a plurality of single-stranded oligonucleotides, wherein a first single-stranded oligonucleotide in the plurality is linked to a first binding partner. It is to be understood that the scaffold nucleic acid and the oligonucleotides are referred to as being single-stranded prior to their hybridization to each other.

In some embodiments, the first binding partner is a nucleic acid such as an oligonucleotide (e.g., a bridge oligonucleotide). In some embodiments, the first single-stranded oligonucleotide binds to the scaffold at non-contiguous yet complementary regions, thereby creating a loop in the nucleic acid complex (FIG. 2B). The loop so created may comprise single- and double-stranded regions. In some embodiments, the first single-stranded oligonucleotide binds to two, non-contiguous regions of the scaffold nucleic acid, both of which are internal to the scaffold nucleic acid. In some embodiments, the two, non-contiguous regions are separated from each other by at least 100, 200, 300, 400, 500, 600, 700, 800, 900, 1000, 1500, 2000, 2500, 3000, 3500, 4000, or more nucleotides. In some embodiments, the two, non-contiguous regions are separated from each other by a number of nucleotides including and between 4-100 nucleotides. In some embodiments, the two, non-contiguous regions are located about the center of the scaffold nucleic acid, and may be equi-distant from the center.

As used herein, regions that are internal to the scaffold, exclude the most 5' and the most 3' nucleotides of the scaffold.

In some embodiments, a second single-stranded oligonucleotide in the plurality is linked to a second binding partner. The second binding partner may be known to have affinity for the first binding partner. The second binding partner may be known or unknown (e.g., it may be a library member that is being screened for binding affinity for the first binding partner).

In some embodiments, the first and second binding partners are not nucleic acid in nature. In some embodiments, the first or the second binding partner is nucleic acid in nature and the other binding partner is not nucleic acid in nature. In some embodiments, the first and second binding partners are both amino acid in nature (e.g., they may be peptides, proteins or protein fragments).

In some embodiments, the first binding partner is a receptor and the second binding partner is a ligand of the receptor. In some embodiments, the first binding partner is an antibody or an antigen-binding antibody fragment and the second binding partner is an antigen (or an epitope-bearing antigen fragment) that is recognized and bound by the antibody or antibody fragment. In some embodiments, the first binding partner is a hapten and the second binding partner is a hapten binding partner. In some embodiments, the first binding partner is a lectin and the second binding partner is a lectin-binding moiety such as a carbohydrate. It is to be understood that the binding partners may be used in an isolated form (e.g., physically separate from components or moieties with which they naturally occur). In some embodiments, they may be bound to a support such as a cell (e.g., a cell surface receptor or ligand).

In some embodiments, the first single-stranded oligonucleotide and the second single-stranded oligonucleotide are separated from each other by at least 10, 20, 30, 40, 50, 60, 70, 80, 90, 100, 110, 120, 130, 140, 150, 160, 170, 180, 190, 200, 220, 240, 260, 280, 300, 350, 400, 500, 600, 700, 800, 900, 1000, 1500, 2000, 2500, 3000, 3500, 4000, 5000 or more nucleotides. In some embodiments, the first single-stranded oligonucleotide and the second single-stranded oligonucleotide are located about equi-distant about the center of the scaffold nucleic acid. In some embodiments, the first and second single-stranded oligonucleotides bind to regions of the scaffold nucleic acid that are internal to the scaffold (i.e., such regions exclude the most 5' and the most 3' nucleotides of the scaffold).

In some embodiments, a third single-stranded oligonucleotide in the plurality is linked to a third binding partner. In some embodiments, a fourth single-stranded oligonucleotide in the plurality is linked to a fourth binding partner. It is to be understood that the terms first, second, third and fourth, are intended to distinguish between the various binding partners being discussed and are not intended to limit the number, arrangement, or combination of binding partners bound to the scaffold nucleic acid (and thus incorporated into the complex) or to connote the position of the binding partner relative to the other binding partner(s) or to the complex as a whole (e.g., the first oligonucleotide or the first binding partner need not be at the 5' or 3' end of the complex, and rather may be internally located). Accordingly, the nucleic acid complex may comprise a binding partner at one (i.e., either the 5' or the 3' end) or at both of its ends (i.e., at the 5' and 3' end). A non-limiting example of such a binding partner is a biotin or a double biotin moiety. The binding partners at the end(s) of the complex may be used to anchor or immobilize the complex to a solid support such as but not limited to a bead or a slide. Accordingly, certain "terminal" binding partners may be common between different complexes in a plurality. In some embodiments, the "internal" binding partners may be different between complexes in a plurality. In some embodiments, the internal binding partners may be the same between complexes in a plurality. The terminal binding partners may interact with each other or with other moieties in the complex, or they may interact with moieties in the sample or on a support such as a solid support. The internal binding partners may interact with each other or with other moieties in the complex, or they may interact with moieties in the sample.

In some embodiments, the nucleic acid complex may comprise one or two terminal binding partners and one or two internal binding partners.

In some embodiments, the oligonucleotides of the plurality may be of equal or about equal length. The oligonucleotides may be at least 20, 30, 40, 50, 60, 70, 80, 90, 100, 110, 120, or more nucleotides in length. The complexity of the plurality of oligonucleotides (i.e., the number of different oligonucleotides in the plurality) will depend in part on the length of the oligonucleotides. In some embodiments, the plurality will consist of at least 20, 30, 40, 50, 60, 70, 80, 90, 100, 110, 120, 130, 140, 150, or more different oligonucleotides.

In various aspects and embodiments described herein, the scaffold nucleic acid is the single-stranded M13 bacteriophage genome.

Thus, in another aspect, the invention provides a nucleic acid complex comprising a single-stranded scaffold nucleic acid hybridized to a plurality of single-stranded oligonucleotides, each of which hybridizes to a contiguous nucleotide sequence, and a bridge oligonucleotide hybridized to two non-contiguous nucleotide sequences of the scaffold nucleic acid. In some embodiments, the complex comprises one or more bridge oligonucleotides, each hybridized to two non-contiguous nucleotide sequences of the scaffold nucleic acid, wherein each bridge oligonucleotide binds to different regions of the scaffold nucleic acid.

Thus, in another aspect, the invention provides a nucleic acid complex comprising a scaffold nucleic acid hybridized to a plurality of oligonucleotides, wherein a first oligonucleotide is linked to a first binding partner, and a second oligonucleotide is linked to a second binding partner. In some embodiments, the first and second binding partners are known or suspected of having affinity for each other. In some embodiments, the first and second binding partners have binding affinity for an analyte that is neither the first nor the second binding partner. In some embodiments, the most 5' hybridized oligonucleotide and/or the most 3' hybridized oligonucleotide are linked to other binding partners such as but not limited to biotin or avidin.

In some embodiments, a binding partner is linked covalently to an oligonucleotide. In some embodiments, a binding partner is linked non-covalently to an oligonucleotide. In some embodiments, the bond between a binding partner and an oligonucleotide (e.g., on the modified oligonucleotides of the invention) has a greater binding strength than the bond between first and second (i.e., internal) binding partners, thereby ensuring that, for example, when the complex is under tension, the bond between the internal binding partners will usually dissociate before the bond between either binding partner and its oligonucleotide "anchor".

In another aspect, the invention provides a composition comprising one or more of any of the foregoing nucleic acid complexes. The plurality may be homogeneous (where all the complexes are identical) or it may be heterogeneous (where at least one complex is different from the others).

In another aspect, the invention provides a composition comprising any one of the foregoing nucleic acid complexes and a solid support. In some embodiments, the nucleic acid complex is linked to the solid support. Such linkage may be covalent linkage or it may be non-covalent linkage. In some embodiments, the nucleic acid complex comprises terminally located biotin and the solid support comprises avidin (including streptavidin). Alternatively, the nucleic acid complex may comprise terminally located avidin (including streptavidin) and the solid support may comprise biotin. In some embodiments, the solid support is a bead.

In some embodiments, the composition comprises a plurality of different nucleic acid complexes. In some embodiments, the nucleic acid complexes in the plurality differ from each other at the first binding partner, the second binding partner, or the first and the second binding partners. In some embodiments, the nucleic acid complexes in the plurality differ from each other based on distance between the first and second single-stranded (i.e., internal) oligonucleotides when the complex is elongated (i.e., when it is not in a looped conformation due to the interaction between the first and second binding partners). In some embodiments, the nucleic acid complexes in the plurality comprise the same binding partners but differ from each other based on the distance between the binding partners.

In another aspect, the invention provides a kit comprising a single-stranded scaffold nucleic acid, and a plurality of single-stranded oligonucleotides, each having a sequence complementary to a sequence on the scaffold nucleic acid, wherein when the oligonucleotides are hybridized to the scaffold nucleic acid no overlap exists between the oligonucleotides. In some instances, each oligonucleotide, in this first subset of oligonucleotides, has a sequence that is complementary to a contiguous sequence on the scaffold nucleic acid intending that every nucleotide in the oligonucleotide is hybridized with a nucleotide in the scaffold, and no "single-stranded bubbles" exist following hybridization. The oligonucleotides may be housed individually and separately in the kit or they may be pooled together, or subsets of the oligonucleotides may be pooled together. In some embodiments, the kit may comprise the scaffold nucleic acid in a circular form and optionally an oligonucleotide that hybridizes to the scaffold in a region that comprises a restriction enzyme cut site such as a BtsCI cut site.

Such an oligonucleotide may be referred to as a "linearization" oligonucleotide. The scaffold and the linearization oligonucleotide may be housed together or separately. In some embodiments, the linearization oligonucleotide is oligo 000A as provided in FIG. 1A.

In some embodiments, the kit further comprises a first single-stranded oligonucleotide linked to a first binding partner. In some embodiments, the kit further comprises a second single-stranded oligonucleotide linked to a second binding partner. In some embodiments, the first and second binding partners have binding affinity to each other. In some embodiments, the first and second binding partners have binding affinity to an analyte that is not a binding partner bound to the single-stranded oligonucleotides of the complex.

In some embodiments, the kit comprises an oligonucleotide comprising a thiol (or other reactive linkage group) on one of its ends (i.e., a terminal reactive group or a terminal thiol). In some embodiments, the thiol is present on the 3' end of the oligonucleotide. In some embodiments, the kit comprises two different oligonucleotides each comprising a thiol (or other reactive linkage group) on one end. In some embodiments, the thiol linked oligonucleotide is oligo 033A as provided in FIG. 1A.

In some embodiments, the kit further comprises third and/or fourth oligonucleotides that hybridize to the scaffold at the most 5' and most 3' regions of the scaffold, wherein each oligonucleotide comprises a terminal or near terminal biotin (e.g., biotin may be linked to the oligonucleotide at the most 5' nucleotide or at the most 3' nucleotide, or at any nucleotide within 5 nucleotides of either the 5' or the 3' end). In some embodiments, these biotin-bearing oligonucleotides are oligos 001A and/or 121A as provided in FIG. 1A.

In some embodiments, the kit further comprises one or more bridge oligonucleotides that each hybridize to two, non-contiguous regions of the scaffold. The non-contiguous regions on the scaffold to which the bridge oligonucleotides bind may be nested relative to each other or they may be consecutively ordered along the length of the complex, as described herein. In some embodiments, one or more bridge oligonucleotides are selected from the group consisting of oligos 033-044A, 033-044B, 033-044C, 033-044D, 033-077A, 033-077B, 033-077C, and 033-077D.

In some embodiments, the kit comprises oligos 001-121, as provided in FIG. 1A. In some embodiments, the kit comprises oligos 001A, 002-120 and 121A as provided in FIG. 1A. It is to be understood that any of the "internal" oligonucleotides may comprise thiol (or other reactive group). Typically, the oligonucleotides comprising thiol (or other reactive group) may be housed separately from the remaining (e.g., unmodified and/or terminally modified) oligonucleotides.

In some embodiments, the kit further comprises a solid support, such as but not limited to a bead (e.g., a magnetic bead).

In another aspect, the invention provides a method comprising combining a single-stranded scaffold nucleic acid with a plurality of single-stranded oligonucleotides, each having a sequence complementary to a sequence on the scaffold nucleic acid, under conditions that allow the single-stranded oligonucleotides to hybridize to the scaffold nucleic acid in a sequence-specific manner without overlap. The plurality comprises a first single-stranded oligonucleotide linked to a first binding partner. In some instances, each oligonucleotide has a sequence that is complementary to a contiguous sequence on the scaffold nucleic acid intending that every nucleotide in the oligonucleotide is hybridized with a nucleotide in the scaffold, and no "single-stranded bubbles" exist following hybridization of the oligonucleotide to the scaffold. In some instances, the entire sequence of each oligonucleotide is complementary to a contiguous sequence on the scaffold nucleic acid. In some embodiments, the scaffold nucleic acid is isolated. In some embodiments, all oligonucleotides in the plurality are present in an equimolar concentration that is about 10-fold greater than the molar concentration of the scaffold nucleic acid. In some embodiments, the plurality comprises a second single-stranded oligonucleotide linked to a second binding partner. The first and second binding partners may have affinity for each other or they may have affinity for an analyte (i.e., the same analyte) that is neither the first or the second binding partner. In some embodiments, the second single-stranded oligonucleotide is present in a molar concentration that equal to the concentration of the scaffold nucleic acid. In some embodiments, the method produces a nucleic acid complex that is at least 80%, 85%, 90%, or 95% double-stranded, or is 100% double-stranded.

In another aspect, the invention provides a method comprising combining a single-stranded scaffold nucleic acid with a plurality of single-stranded oligonucleotides, each having a sequence complementary to a sequence on the scaffold nucleic acid, under conditions that allow the single-stranded oligonucleotides to hybridize to the scaffold nucleic acid without overlap, to form an intermediate (e.g., an intermediate of a final product), and combining the intermediate with a first single-stranded oligonucleotide linked to a binding partner or with a bridge oligonucleotide that binds to two non-contiguous sequences of the scaffold nucleic acid, under conditions that allow the first single-stranded oligonucleotide or the bridge oligonucleotide to hybridize to the intermediate without overlap with other bound oligonucleotides. In some instances, each oligonucleotide has a sequence that is complementary to a contiguous nucleotide sequence on the scaffold nucleic acid intending that every nucleotide in the oligonucleotide is hybridized with a nucleotide in the scaffold, and no "single-stranded bubbles" exist following hybridization of the oligonucleotide to the scaffold. In some instances, the entire sequence of each oligonucleotide is complementary to a contiguous sequence on the scaffold nucleic acid. In some embodiments, the intermediate is at least 80%, at least 85%, at least 90%, or at least 95% double-stranded, or more. In some embodiments, the method produces a nucleic acid complex that is 100% double-stranded.

In another aspect, the invention provides a method comprising combining a single-stranded scaffold nucleic acid with a plurality of single-stranded oligonucleotides, each having a sequence complementary to a sequence (e.g., a contiguous sequence) on the scaffold nucleic acid, and one or more bridge oligonucleotides each having a sequence complementary to two non-contiguous sequences on the scaffold nucleic acid, under conditions that allow the oligonucleotides to hybridize to the scaffold nucleic acid without overlap. In some embodiments, the method produces a nucleic acid complex that is at least 80%, at least 85%, at least 90%, or at least 95% double-stranded, or more. In some embodiments, the method produces a nucleic acid complex that is 100% double-stranded. The loop formed between the two non-contiguous regions comprises single-stranded and/or double-stranded regions. The two non-contiguous sequences may be spaced apart on the scaffold nucleic acid by 10 or more, or 20 or more nucleotides.

In another aspect, the invention provides a method comprising placing any of the foregoing nucleic acid complexes comprising a first and a second binding partner under conditions that allow for binding of the first and second binding partners to each other, and detecting a change in binding between a first binding partner a second binding partner. In some embodiments, the first and second binding partners are linked to separate oligonucleotides that are hybridized to a single scaffold nucleic acid. The change in binding may be detected under tension, in some embodiments. The change in binding may be determined using any methodology. The change in binding may be evidenced by a change in length of the nucleic acid complex using any methodology including for example gel electrophoresis. Typically, the length of the nucleic acid complex, when the first and second binding partners are bound to each other, is different from length of the nucleic acid complex when the first and second binding partners are not bound to each other. In some instances, length of the complex, when the first and second binding partners are bound to each other, is less than the length of the complex when the first and second binding partners are not bound to each other.

In some embodiments, length is the distance between the two ends of the complex. In some embodiments, length is "apparent" length. Apparent length is the length of the complex as observed using a particular technique, such as for example gel electrophoresis. In such electrophoretic embodiments, apparent length is typically determined relative to a set of nucleic acid standards of known length. In such embodiments, apparent length is determined by the distance the complex travels in a particular gel electrophoresis environment, and this distance is typically compared to the distances that nucleic acids of known length travel in the same environment. This distance may alternatively be compared to the distances that the complex travels when it is in its open conformation (i.e., when the first and the second binding partners are not bound to each other) and/or its closed conformation (i.e., when the first and the second binding partners are bound to each other).

In some embodiments, once the first and second binding partners are bound to each other, the nucleic acid complex is combined with excess soluble forms of the first or second binding partners or fragments thereof that bind to the first or the second binding partner (and thus compete with their bound counterpart), prior to detecting a change in binding.

In another aspect, the invention provides a method comprising combining any of the foregoing nucleic acid complexes comprising a scaffold nucleic acid hybridized to a plurality of oligonucleotides (including, for example, an intermediate complex as described above) with one or more bridge oligonucleotides that each hybridize to two non-contiguous sequences of the scaffold nucleic acid, under conditions that allow the bridge oligonucleotides to bind to their respective two non-contiguous sequences, and detecting a change in binding between the nucleic acid complex and the one or more bridge oligonucleotides (i.e., binding of the one or more bridge oligonucleotides, each to two non-contiguous sequences in the nucleic acid complex). The change in binding may be detected as a change in length of the complex. The length of the complex, when the one or more bridge oligonucleotides are bound to the two non-contiguous sequences (and thus the scaffold), is different from the length of the complex when the one or more bridge oligonucleotides are not bound to the two non-contiguous regions (and thus the scaffold). In some embodiments, the length of the complex, when one or more bridge oligonucleotides are bound to their respective two, non-contiguous sequences, is less than the length of the complex when the one or more bridge oligonucleotides are not bound to the two non-contiguous regions. In some embodiments, the change in binding is detected under tension. In some embodiments, once the bridge oligonucleotide is bound to the two non-contiguous sequences in the nucleic acid complex, the nucleic acid complex is combined with excess soluble form of the bridge oligonucleotide, or a fragment of the bridge oligonucleotide, or an oligonucleotide that is complementary to the bridge oligonucleotide, or a fragment thereof, prior to detecting binding.

Change in binding including presence or absence of binding, in any of the aspects and embodiments of the invention, may be detected using any suitable methodology including but not limited to gel electrophoresis, optical tweezers, atomic force microscopy (AFM), centrifuge force microscopy (CFM), magnetic tweezers, tethered particle motion, and single-molecule fluorescence imaging.

In some embodiments, length refers to the shortest distance between the 5' and 3' ends of the complex. Length in a gel electrophoresis context may be referred to herein as apparent length because it is determined by the distance the complex travels in a gel electrophoresis environment compared to the distance linear nucleic acids of known length travel in the same environment (e.g., on the same gel) or the distance that the open and/or closed conformation complexes travel in the same gel environment. In another aspect, the invention provides use of any of the foregoing nucleic acid complexes to measure association and/or dissociation kinetics between binding partners. In related aspects, the invention provides a method comprising detecting a rate of association or dissociation between a first and a second binding partner wherein the first and the second binding partners are linked to any of the foregoing nucleic acid complexes, wherein association or dissociation is detected by a change in length of the nucleic acid complex.

In some embodiments, one or both binding partners are known. In some embodiments, one binding partner is a member of a library of putative binding partners and the method is intended as a screening method to identify binding partners with affinity for a particular target (i.e., the other binding partner) or as a comparison of a plurality of putative or known binding partners based on affinity. Accordingly, in some embodiments, the binding partners are known to have affinity for each other, while in other embodiments, it may not be known a priori whether they have affinity for each other, or the degree of affinity (i.e., the binding strength) in a given pair may not be known. In some embodiments, association and dissociation kinetics may be determined by measuring the lengths (or apparent lengths) of complexes over a span of time, optionally under one or a variety of conditions. Length measurements may be obtained using techniques known in the art including those described herein.

In some embodiments, association and/or dissociation (or a change in length of the nucleic acid complex) is detected using gel electrophoresis, atomic force microscopy (AFM), optical tweezers, centrifuge force microscopy (CFM), magnetic tweezers, tethered particle motion, or single molecule fluorescence imaging.

In some embodiments, the method comprises repeatedly detecting association and dissociation of the same first and second binding partners using the same nucleic acid complex. In some embodiments, the rate of association or dissociation is detected in the presence of excess soluble forms of the first or the second binding partner.

In some embodiments, the binding pair is comprised of a receptor and a ligand for the receptor. In some embodiments, the binding pair is comprised of two nucleic acids. In some embodiments, the binding pair is an antibody and antigen.

In another aspect, the invention provides a method comprising combining any of the foregoing nucleic acid complexes comprising a first and a second binding partner with a sample, under conditions that allow for binding of the first and second binding partners to an analyte, if present in the sample, that is neither the first nor the second binding partner, and detecting binding of the first and the second binding partners to the analyte, if present in the sample, based on a change in length of the nucleic acid complex. Binding of the first and the second binding partners to the analyte may be determined based on a change in length of the nucleic acid complex.

In another aspect, the invention provides a method comprising placing any of the foregoing nucleic acid complexes comprising a first binding partner and a library member, spaced apart from each other along the length of the complex, under conditions that allow for binding of the first binding partner and the library member provided the library member has sufficient affinity for the first binding partner, and detecting binding of the first binding partner to the library member, based on a change in the length of the nucleic acid complex, wherein the nucleic acid binding partner is a nucleic acid. Binding of the first binding partner and the library member may be determined based on a change in length of the nucleic acid complex. The library member may be a nucleic acid such as an aptamer. In some embodiments, the method further comprises obtaining a nucleic acid complex comprising a library member having sufficient affinity for the first binding partner, and amplifying and sequencing the library member.

In another aspect, the invention provides a method comprising placing a plurality of any of the foregoing nucleic acid complexes comprising a first and a second binding partner under conditions that allow for binding of the first and second binding partners to each other, wherein the nucleic acid complexes comprise the same first and second binding partners but differ from each other based on distance between the first and second binding partners (or first and second single-stranded oligonucleotides to which the binding partners are bound), detecting a change in binding between the first binding partner and the second binding partner as a function of distance between the first and second binding partners.

In another aspect, the invention provides a method of measuring interaction kinetics, including bulk interaction kinetics. In some embodiments, the method includes (a) forming a looped nucleic acid (e.g., DNA) construct, as described herein, that relies on an interaction (e.g., binding) of two molecules, such as for example a receptor and ligand, to each other, (b) quenching the interaction (e.g., with excess receptor or ligand to prevent rebinding after dissociation), and (c) monitoring the relative amount of looped construct over time to measure kinetics. The construct may comprise one copy of a receptor and one copy of its respective ligand, and quenching may occur in the presence of excess receptor or excess ligand. The construct may comprise two copies of receptor, the construct may be formed in the presence of ligand, and quenching may occur in the presence of excess receptor. The construct may comprise two copies of ligand, the construct may be formed in the presence of receptor, and quenching may occur in the presence of excess ligand.

In another aspect, the invention provides a system comprising (a) a set of nucleic acid structures, each structure capable of being converted from a first state to a second state upon addition of a key component, wherein the first state and the second state are distinguishable from each other, and (b) a set of key components, each key component capable of binding to and thereby converting a nucleic acid structure from a first state to a second state, wherein the set of key components are physically separate from the set of nucleic acid structures, wherein a combination of nucleic acid structures in prescribed first or second states is used to convey non-nucleic acid information.

In some embodiments, the system further comprises (c) a set of distractor components that do not bind to the nucleic acid structures and the key components. In some embodiments, the distractor components are combined with the set of nucleic acid structures and/or the set of key components. In some embodiments, the set of key components converts only a subset of the nucleic acid structures from a first state to a second state.

In some embodiments, the nucleic acid structures are single-stranded nucleic acids of various known lengths. In some embodiments, the key components are single-stranded oligonucleotides that hybridize to and convert the nucleic acid structures to double-stranded nucleic acids of various known lengths.

In some embodiments, the nucleic acid structures are any of the foregoing nucleic acid complexes of various known lengths in an open (e.g., unbound or unlooped) conformation, the key components are single-stranded oligonucleotides that hybridize to and convert the nucleic acid structures to nucleic acid complexes of various known lengths in a closed (e.g., bound or looped) conformation.

In some embodiments, the nucleic acid structure is a mixture of single-stranded oligonucleotides and the key component is a scaffold nucleic acid that is able to bind all of the single-stranded oligonucleotides in the mixture to form a nucleic acid complex of the invention for example by self-assembly processes. In some embodiments, the first state is a mixture of oligonucleotides and the second state is a nucleic acid complex of the invention, in open or closed conformation, depending on the oligonucleotides present in the first state. Thus, it should be understood that the term "nucleic acid structure" as used in these aspects and embodiments does not intend a single molecule (e.g., a single nucleic acid) and rather can embrace a plurality of molecules that may or may not be physically attached to each other.

In some embodiments, the key component is one or more oligonucleotides, one or more analytes, or one or more scaffold nucleic acids.

In another aspect, the invention provides a method comprising encoding non-nucleic acid information using a nucleic acid construct that represents a bit with two states.

In some embodiments, the nucleic acid construct is a nucleic acid complex able to convert from an open (or unbound or unlooped) to a closed (or bound or looped) state (or vice versa) upon contact with a key component.

In some embodiments, the nucleic acid construct is able to convert from a single-stranded state to a double-stranded state upon contact with a key component. In some embodiments, the nucleic acid construct is a single-stranded oligonucleotide and the key component is a key oligonucleotide that is complementary to the single-stranded oligonucleotide. The key oligonucleotide may be the same length or of different length than the single-stranded oligonucleotide.

In some embodiments, the nucleic acid construct is a mixture of single-stranded oligonucleotides and the key component is a scaffold nucleic acid that binds to each of the oligonucleotides in the mixture.

In some embodiments, the key component is a one or more oligonucleotides (e.g., key oligonucleotides), one or more analytes (e.g., key analytes), or one or more scaffold nucleic acids (e.g., key scaffold nucleic acid).

In some embodiments, the nucleic acid construct is provided in a composition comprising a plurality of nucleic acid constructs. In some embodiments, each nucleic acid construct represents a bit with two states.

In some embodiments, the nucleic acid construct is provided in a composition comprising one or more distractor components. In some embodiments, the key component is provided in a composition comprising one or more distractor components. In some embodiments, the distractor components are distractor oligonucleotides, distractor analytes, and/or distractor scaffolds. Distractor components do not bind to the nucleic acid structures or the key components used in the method.

In some embodiments, the plurality of nucleic acid constructs comprises physically separate subsets of nucleic acid constructs. In some embodiments, the nucleic acid constructs within a subset are distinguishable from each other based on length. In some embodiments, the nucleic acid constructs are oligonucleotides of different lengths.

In some embodiments, the method further comprises encrypting non-nucleic acid information using one or more nucleic acid constructs in a first state. Non-nucleic acid information may be alphabetical information (e.g., text) or numerical information (e.g., serial numbers). In some embodiments, the method further comprises contacting the composition with a key component that converts a nucleic acid construct from a first state to a second state, thereby rendering the nucleic acid construct in the second state. The second state of the construct relays non-nucleic acid information.

In some embodiments, the key component is a plurality of key components and the nucleic acid construct is a plurality of nucleic acid constructs. In some embodiments, a subset of nucleic acid constructs in a composition are converted from a first to a second state.

In some embodiments, the first state is a mixture of single-stranded oligonucleotides and the second state is a double-stranded nucleic acid comprising a key scaffold nucleic acid hybridized to the single-stranded oligonucleotides.

In some embodiments, the first state is an open (or unbound or unlooped) nucleic acid complex of the invention and the second state is a closed (or bound or looped) nucleic acid complex of the invention comprising, for example, a key oligonucleotide or a key analyte.

In some embodiments, the first state is a single-stranded nucleic acid and the second state is a double-stranded nucleic acid comprising a key oligonucleotide hybridized to the single-stranded nucleic acid.

In another aspect, the invention provides a method comprising deciphering non-nucleic acid information from a nucleic acid sample by combining the nucleic acid sample with one or more key single-stranded oligonucleotides, and analyzing the sample for the presence of double-stranded nucleic acids formed from hybridization of the one or more key single-stranded oligonucleotides to complementary nucleic acids in the nucleic acid sample, wherein presence, pattern and/or length of the double-stranded fragments provide coded information.

In some embodiments, the sample is analyzed using gel electrophoresis with an intercalating dye. In some embodiments, the one or more key single-stranded oligonucleotides are of various lengths. In some embodiments, the one or more key single-stranded oligonucleotides are of the same or different length as their complementary single-stranded nucleic acids in the sample.

In another aspect, the invention provides a method comprising deciphering non-nucleic acid information from a nucleic acid sample by combining the nucleic acid sample with one or more key components, and analyzing the sample for the presence of closed nucleic acid complexes formed from hybridization of the one or more key components to nucleic acids in the sample, wherein presence, pattern and/or length of the closed nucleic acid complexes provide coded information. In some embodiments, the sample is analyzed using gel electrophoresis. In some embodiments, the closed nucleic acid complexes differ from each other according to length.

In another aspect, the invention provides a method comprising deciphering non-nucleic acid information from a nucleic acid sample by combining the nucleic acid sample with one or more key components, and analyzing the sample for the presence of one or more nucleic acid complexes each comprising a scaffold nucleic acid hybridized to a plurality of single-stranded oligonucleotides, wherein presence, pattern, state and/or length of the nucleic acid complexes provide coded information. In some embodiments, the nucleic acid complexes are analyzed using gel electrophoresis. In some embodiments, the nucleic acid complexes differ from each other according to length.

In another aspect, the invention provides a method of authenticating a product comprising labeling a non-nucleic acid product with a nucleic acid sample comprising a plurality of nucleic acid structures, wherein each of the nucleic acid structures is in a first state and is capable of conversion to a second state upon binding to a key component, and wherein the nucleic acid structures in their respective second states are distinguishable from each other.

In some embodiments, the key component is one or more single-stranded oligonucleotides. In some embodiments, the key component is one or more scaffold nucleic acids. In some embodiments, the key component is one or more analytes. In some embodiments, the same key component could be used to convert all or a subset of nucleic acid structures from their first to their second states.

In some embodiments, the first state is a mixture of single-stranded oligonucleotides, the key component is a scaffold nucleic acid, and the second state is a double-stranded nucleic acid comprising a scaffold nucleic acid hybridized to the single-stranded oligonucleotides. In some embodiments, the first state is a single-stranded nucleic acid, the key component is a complementary single-stranded nucleic acid, and the second state is a double-stranded nucleic acid formed from the hybridization of the two single-stranded nucleic acids. In some embodiments, the first state is a nucleic acid complex in an open (or unlooped or unbound) conformation, the key component is one or more bridge oligonucleotides or one or more analytes, and the second state is the nucleic acid complex in a closed (or looped or bound) conformation.

In some embodiments, the second states are distinguishable from each other based on length. In some embodiments, the second states are distinguishable from each other using gel electrophoresis.

These and other aspects and embodiments of the invention will be described in greater detail herein.

DETAILED DESCRIPTION OF INVENTION

The invention relates broadly to nucleic acid based complexes comprising double-stranded nucleic acid and one or more various types of binding partners for targets of interest. Also provided are methods of using such complexes to determine kinetics of binding interactions, such as on- and/or off-rates, to determine affinities of binding interactions, to identify new binding partners for targets of interest, to detect one or more targets in a sample, and to encrypt and decrypt messages, among other things.

The invention provides in part a single-molecule attachment technique that facilitates reliable and accurate single-molecule force measurements. Using DNA self-assembly techniques, a unique linker has been nano-engineered that behaves as a force-activated single-molecule switch. This switch changes conformation under force to signify bond rupture, providing an identifiable molecular signature that distinguishes between the presence and absence of a binding interaction between binding partners, thereby eliminating the possibility of accidentally measuring nonspecific, multiple and unknown interactions. Furthermore, this construct enables the same pair of binding partners to be brought back together following rupture, opening the way to at least high-throughput serial measurements, single-molecule on-rate and off-rates determination, analysis of population heterogeneity, and identification of new binding partners for targets of interest. The approach provided herein is simple, versatile and modular, and can be easily implemented using standard commercial reagents and laboratory equipment.

Also presented herein in various aspects are applications and methods that utilize the linker construct to measure chemical kinetics and force-dependent kinetics of molecular interactions, to detect the presence of molecules and reagents, to screen collections of molecules for particular targets of interest, and to encrypt and decrypt information, inter alia.

Figure 2A:
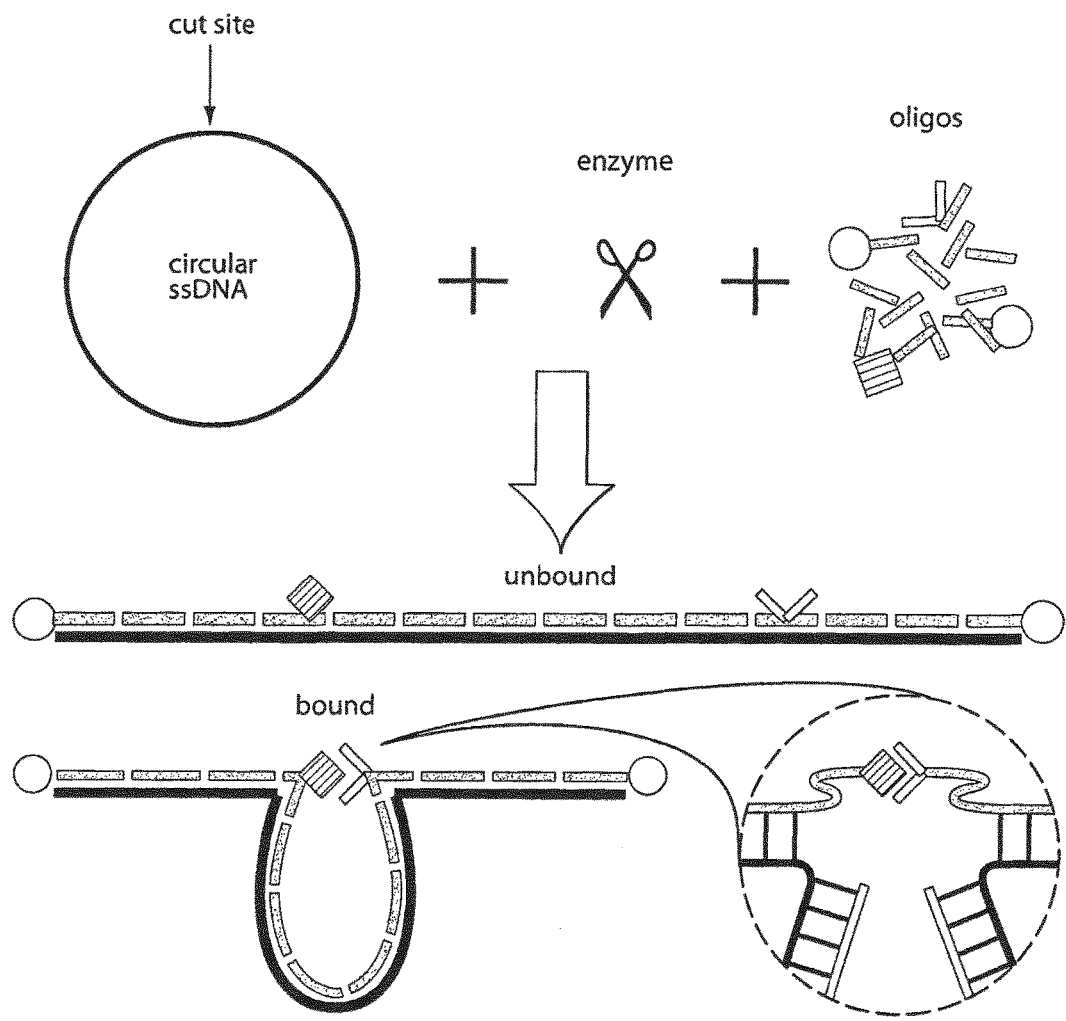
FIG. 2A. Looped linker construction using DNA origami: circular single-stranded DNA is enzymatically cleaved at a single site and mixed with over 100 oligonucleotides to self-assemble into a looped linker with functional groups.
Figure 2B:
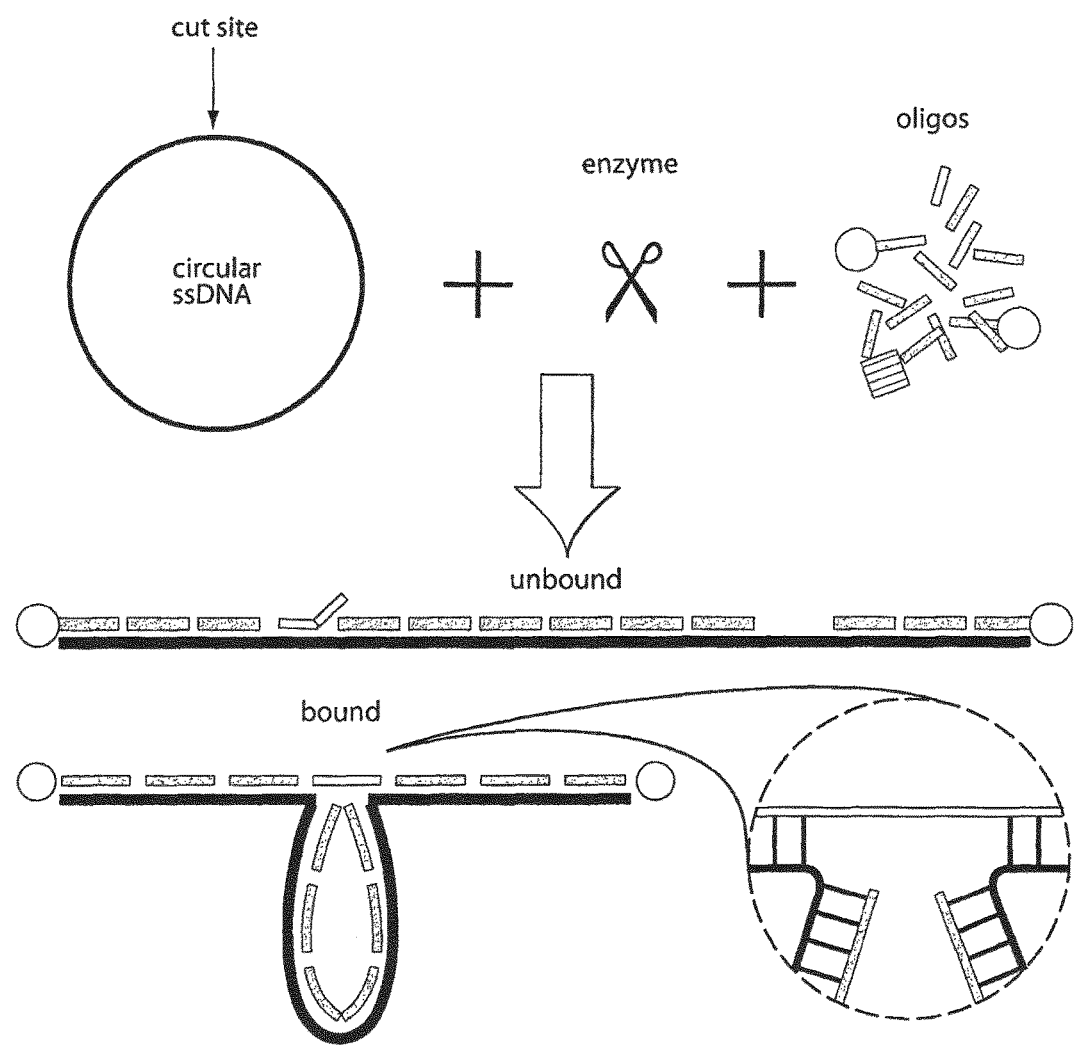
FIG. 2B. Looped linker construction using DNA origami. Circular single-stranded DNA is enzymatically cleaved at a single site and mixed with over 100 oligonucleotides to self-assemble into a looped linker held together by a single "bridge" or "staple" oligonucleotide.

Certain complexes of the invention are constructed using DNA origami methods (Rothemund P. W. K. (2006) Nature 440: 297-302; Douglas S. M. et al. (2009) Nature 459: 414-8). By mixing a long piece of single-stranded DNA with a carefully designed mixture of oligonucleotides, looped single-molecule linkers are constructed via DNA self-assembly. In some embodiments, the complexes comprise an integrated binding pair (e.g., a receptor-ligand pair) (for example, FIG. 2A). As used herein, the terms linker and complex are used interchangeably.

Certain complexes (or linkers) of the invention are each comprised of a single "scaffold" nucleic acid and a plurality of oligonucleotides hybridized thereto. The scaffold nucleic acid and the oligonucleotides are single-stranded prior to hybridization to each other. Accordingly, the scaffold nucleic acid and the oligonucleotides may be referred to herein as being "single-stranded" and it is to be understood that this refers to their state prior to such hybridization.

The invention refers to the scaffold nucleic acid hybridized to a plurality of oligonucleotides as a nucleic acid complex. Such complexes may be at least 50%, at least 60%, at least 70%, at least 80%, at least 90%, at least 95%, at least 96%, at least 97%, at least 98%, at least 99%, or 100% double-stranded. In some embodiments, they are at least 80% double stranded. The complexes of the invention may therefore comprise double-stranded and single-stranded regions. As used herein, a double-stranded region is a region in which all nucleotides on the scaffold are hybridized to their complementary nucleotides on the oligonucleotide. These double-stranded regions may comprise "single-stranded nicks" as the hybridized oligonucleotides are not ligated to each other. The single-stranded regions are scaffold sequences that are not hybridized to oligonucleotides. The invention contemplates the use of complexes having one or more single-stranded regions in between double-stranded regions (typically as a result of unhybridized nucleotides in between adjacent hybridized oligonucleotides).

In some instances, the nucleic acid complex is formed by first hybridizing unmodified (or fixed) oligonucleotides to the scaffold nucleic acid to form a nucleic acid complex intermediate, and then hybridizing modified (or variable) oligonucleotides to the scaffold nucleic acid to form the nucleic acid complex. The modified oligonucleotides may be combined with (and typically hybridized to) the scaffold simultaneously or sequentially. As used herein, a nucleic acid complex intermediate refers to a scaffold that is hybridized to some but not the entire complement of oligonucleotides that is designed to bind to the entire length of the scaffold.

The scaffold nucleic acid may be of any length sufficient to allow association (i.e., binding) and dissociation (i.e., unbinding) of binding partners to occur, to be detected, and to be distinguished from other events. In some instances, the scaffold nucleic acid is at least 1000 nucleotides in length, and it may be as long as 20,000 nucleotides in length (or it may be longer). The scaffold nucleic acid may therefore be 1000-20,000 nucleotides in length, 2000-15,000 nucleotides in length, 5000-12,000 in length, or any range therebetween. The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. In some embodiments, including those involving a gel electrophoresis readout, the scaffold nucleic acid may be at least 40, at least 50, at least 60, at least 70, at least 80, at least 90, at least 100, at least 200, at least 300, at least 400, at least 500, at least 600, at least 700, at least 800, or at least 900 nucleotides in length. The scaffold nucleic acid may therefore be 100-1000 nucleotides in length, or 100-300 nucleotides in length, without limitation. In some embodiments, the scaffold is about or less than 200 nucleotides in length. In some embodiments, the scaffold and oligonucleotides are chosen and the binding partners are positioned to yield loops of about 40-100 base pairs. The scaffold nucleic acid may also be non-naturally occurring nucleic acids such as polymerase chain reaction (PCR)-generated nucleic acids, rolling circle amplification (RCA)-generated nucleic acids, etc. It is important that the scaffold nucleic acid is rendered single-stranded either during or post synthesis. Methods for generating a single-stranded scaffold include asymmetric PCR. Alternatively, double-stranded nucleic acids may be subjected to strand separation techniques in order to obtain the single-stranded scaffold nucleic acids. The scaffold nucleic acid may comprise DNA, RNA, DNA analogs, RNA analogs, or a combination thereof, provided it is able to hybridize in a sequence-specific and non-overlapping manner to the oligonucleotides. In some instances, the scaffold nucleic acid is a DNA.

The scaffold nucleic acid is hybridized to a plurality of oligonucleotides. Each of the plurality of oligonucleotides is able to hybridize to the scaffold nucleic acid in a sequence-specific and non-overlapping manner (i.e., each oligonucleotide hybridizes to a distinct sequence in the scaffold). The complex may comprise varying lengths of double-stranded regions. As a non-limiting example, 90% or more, including 95%, 96%, 97%, 98%, 99% and 100% of the scaffold nucleic acid may be hybridized to oligonucleotides. It is to be understood that the scaffold may also comprise a plurality of nicks that are typically located between bound oligonucleotides. The length and the number of oligonucleotides used may vary. It will be understood that the greater the length of the oligonucleotides, the fewer that will be needed to hybridize to the scaffold nucleic acid. In some instances, the length and sequence of the oligonucleotides is chosen so that each oligonucleotide is bound to the scaffold nucleic acid at a similar strength. This is important if a single condition is used to hybridize a plurality of oligonucleotides to the scaffold nucleic acid. In some instances, the oligonucleotides are designed to be of approximately equal length. The oligonucleotides may be about 10, about 15, about 20, about 30, about 40, about 50, about 60, about 70, about 80, about 90 or about 100 nucleotides in length. The number of oligonucleotides in the plurality may be about 50, about 60, about 70, about 80, about 90, about 100, about 110, about 120, about 130, about 140, about 150, about 160, about 170, about 180, about 190, or about 200, without limitation.

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides. It will be understood that the number of oligonucleotides will depend in part on the application, the length of the scaffold, and the length of the oligonucleotides themselves.

According to the invention, certain of the oligonucleotides hybridized to the scaffold nucleic acid will be unmodified. Unmodified oligonucleotides include oligonucleotides that are not linked to binding partners such as the binding partners that the linkers are designed to test (e.g., an antibody or an antigen) and the binding partners used to immobilize the linker onto a solid support such as but not limited to a bead (e.g., biotin). The majority of oligonucleotides hybridized to a scaffold nucleic acid may be unmodified. Unmodified oligonucleotides may be referred to herein as "fixed" oligonucleotides.

Other oligonucleotides hybridized to the scaffold may be modified. Modified oligonucleotides include those that are linked to binding partners that the linkers are designed to test (e.g., a receptor and/or its ligand, an antibody and/or its antigen, etc.). Modified oligonucleotides also include those that are modified and thus used to immobilize the complex (or linker) onto a solid support such as but not limited to a bead. Such modified oligonucleotides including biotinylated oligonucleotides. Modified oligonucleotides may be referred to herein as "variable" oligonucleotides since these oligonucleotides may be modified by linking to a variety of binding partners depending on the method of use.

Regions comprising scaffold hybridized to unmodified oligonucleotides may be referred to herein as "fixed" regions. Regions comprising scaffold hybridized to modified oligonucleotides may be referred to herein as "variable" regions.

The spacing of modified (or variable) oligonucleotides along the length of the scaffold nucleic acid may vary. In some embodiments, the nucleic acid complex may comprise three or four variable regions (e.g., three or four modified oligonucleotides). As an example, a nucleic acid complex may comprise modified oligonucleotides at one or both of its ends as well as two internal modified oligonucleotides. The modified oligonucleotides at the ends of the complex may be used to immobilize the complex to a solid support such as a bead. The modified oligonucleotides internal to the complex may be linked individually to members of a binding pair (i.e., each of the two oligonucleotides is linked to a member of the binding pair such that the complex comprises the binding pair, with each member of the pair on a different oligonucleotide). The internal modified oligonucleotides may be symmetrically or quasi-symmetrically located around the center of the linker. In other words, they may be positioned equi-distant from the center of the scaffold (or the complex).

In some embodiments, the invention contemplates the use of a plurality of complexes each comprising the same binding pair. The difference between the complexes in the plurality is the distance between the binding pair members (i.e., the binding partners). For example, the plurality may comprise complexes in which the distance between the binding pair members is 300 base pairs, 200 base pairs, 150 base pairs, 100 base pairs, 80 base pairs, 60 base pairs, and 40 base pairs. The complexes are then analyzed for their ability to form looped structures based on interaction between the binding partners. It is expected that as the distance between the binding partners decreases, a greater internal force is exerted on the binding interaction. Accordingly, the binding interaction will continue until the internal force becomes too great and the complex assumes the more energetically favorable linear state. The kinetics and strength of a binding interaction between two binding partners can be analyzed using this approach.

Figure 3A:
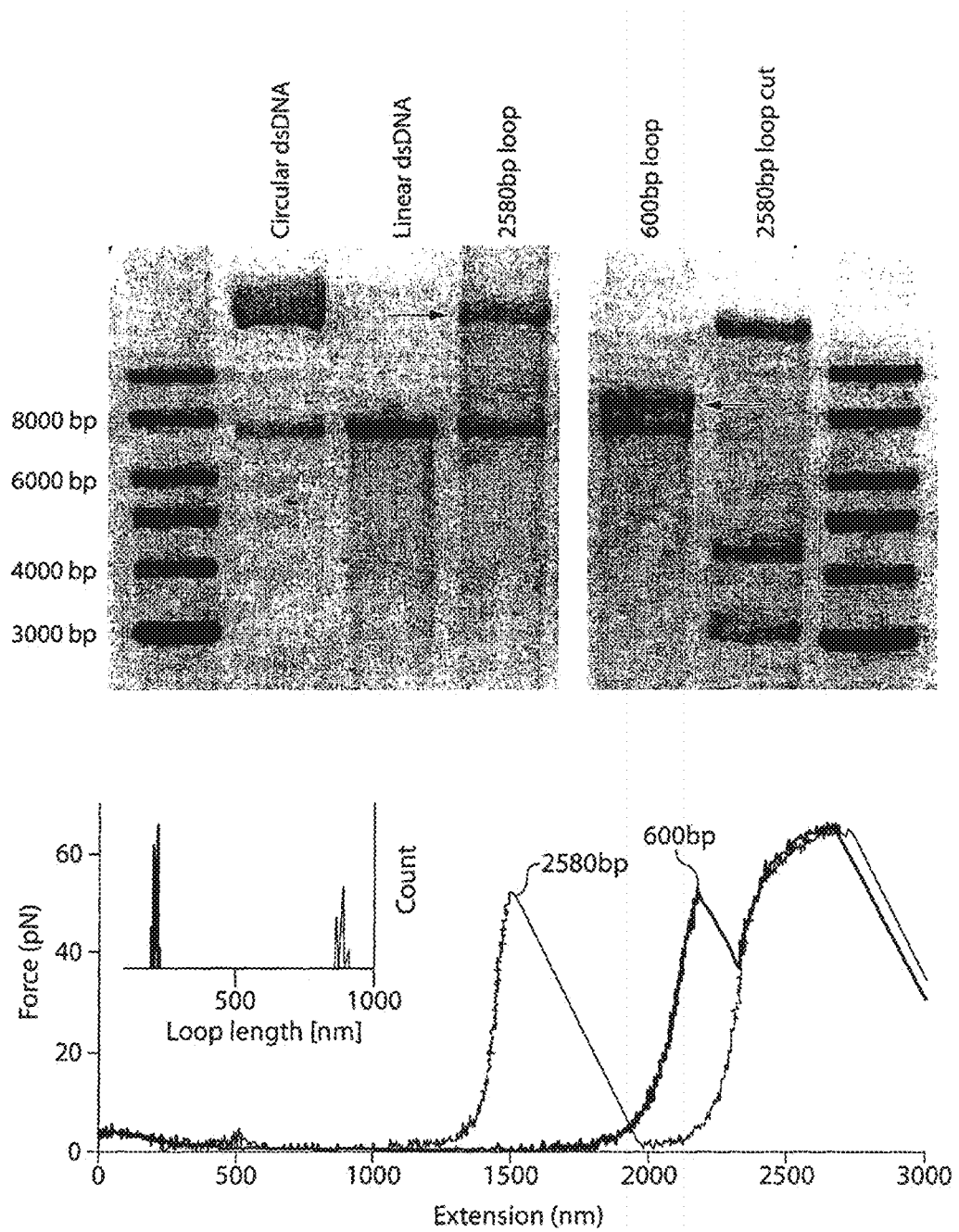
FIG. 3A. Verification of DNA bridge looped linker. Top: gel electrophoresis on a 0.7% agarose gel at 5 V cm-1 for 2 h, stained with SYBR® gold. Bottom: single-molecule pulling trajectories demonstrating the sudden increase in tether length that signifies bond rupture events. The inset shows a histogram of the change in tether length for the 2580 bp (red) and 600 bp (black) looped linkers.

Importantly, the distance between the internal modified oligonucleotides will be used to distinguish association and dissociation between binding partners linked to the complex. This is because when the binding partners are associated with each other, a loop will be formed comprising the double-stranded, nicked nucleic acid sequence that exists between the binding partners. When the binding partners are not associated to each other (i.e., unbound), then the loop does not form and the complex length is different. The complex length may be detected by direct measurements, for example, under tension, as described herein. When measured under tension, the transition from associated to dissociated binding partners is indicated by an increase in length of the complex. The length of the complex, in this and related aspects, intends the shortest distance between the two ends of the complex and is to be distinguished from the apparent length (discussed below) which is determined using gel electrophoresis and the length of the scaffold nucleic acid (which will not change as a result of association and disassociation of a binding pair). When measured using gel electrophoresis, the transition from associated to dissociated binding partners (or vice versa) is indicated by a difference in migration distance through the gel. In some instances, the transition from associated to dissociated binding partners (and thus closed to open states) is indicated by an increase in the migration distance through the gel (e.g., akin to a shorter nucleic acid). As shown in FIG. 3A, a circular scaffold such as circular M13 migrates the slowest, a linearized double-stranded version of M13 (without binding partner association) migrates fastest, and complexes having associated binding partners (i.e., having looped conformations) migrate in between. Importantly, the migration pattern differs based on the length of the loop, with loops that are on the order of about 2590 base pairs clearly distinguishable from loops that are on the order of about 600 base pairs.

The ability to distinguish loops of differing sizes facilitates the use of multiple complexes in a single assay where one or subsets of complexes (all having the same loop size) are specific for a particular analyte in a sample. In these aspects of the invention, the binding partners bound to the complex do not bind to each other but rather bind to the same analyte. Accordingly, in the presence of the analyte a loop is formed while in the absence of the analyte no loop is formed. The looped (or closed or bound) complex migrates to a different degree than does the linear (or open or unbound) complex. Additionally, loops of different sizes can be distinguished from each other and as a result the presence (or absence) of a multiple analytes (each detected by a complex having a loop of a particular size) can be determined simultaneously in a multiplexed assay. Such methods may be used to detect the presence of a single or multiple analytes and may form the basis of a diagnostic assay.

It is to be understood that the invention intends several variations on the nucleic acid complexes described herein. Typically, these variations all commonly comprise a nucleic acid complex having two or more binding partners. The binding partners may have binding specificity for each other or they may have binding specificity for a common analyte. Several of the methods of the invention rely on the association and/or dissociation of binding partners. A change in the complex (e.g., from an open to a closed conformation or from a closed to an open conformation) provides information about the kinetics and strength of the binding interaction. The binding partners may be non-covalently or covalently bound to the complex. Typically, even if the binding partners are not bound to each other, they are nevertheless bound to the nucleic acid complex.

Thus, in a first variation, the nucleic acid complex comprises two binding partners having binding specificity for each other. The binding partners are physically separate and thus spaced apart from each other along the length of the complex (i.e., when not bound to each other). When bound to each other, the nucleic acid complex assumes a looped (or closed or bound) conformation having a different length, including a different apparent length, compared to the nucleic acid complex in an open (or unbound) conformation.

In another variation, the nucleic acid complex comprises two binding partners having binding specificity for a common analyte. The binding partners are physically separate and thus spaced apart from each other (when not bound to the common analyte). When bound to the common analyte, the nucleic acid complex assumes a looped (or closed or bound) conformation having a different length, including a different apparent length, compared to the nucleic acid complex in an open (or unbound) conformation.

The invention further contemplates that a nucleic complex may comprise more than two linked binding partners. The number of binding partners may be 2, 4 or more. In some embodiments, pairs of binding partners are provided, with each pair having binding specificity for each other (i.e., rather than binding specificity for a common analyte). The location or arrangement of the binding partners may vary and may include serially positioned binding pairs or nested binding pairs, or combinations thereof. As an example, assume that A1 and A2 are a binding pair (e.g., first and second binding partners) and B1 and B2 are a different binding pair (e.g., third and fourth binding partners), then these may be arranged as 5'-A1-A2-B1-B2-3', or they may be arranged as 5'-A1-B1-B2-A2-3'.

The invention further contemplates that the binding partners in a pair may be both known, or one may be known and the other may be unknown. As an example of the latter instance, one binding partner may be a known moiety (e.g., a receptor) and the other binding partner may be a member of a library that is being screened for its binding affinity to the known moiety. The library may be an aptamer library and the member that binds with sufficient affinity to the known moiety may be identified by isolating the complex from a gel electrophoresis band, amplifying and sequencing.

In a second variation, the nucleic acid complex is used together with a non-covalently bound nucleic acid (e.g., a bridge oligonucleotide) that hybridizes to two non-contiguous regions of the scaffold nucleic acid, thereby creating a looped conformation in the nucleic acid complex. The invention contemplates that a single complex may be used together with 1, 2 or more bridge oligonucleotides. As an example, assume that A1 and A2 are the two non-contiguous regions to which a first bridge oligonucleotide binds and B1 and B2 are the two non-contiguous regions to which a second bridge oligonucleotide binds, then these regions may be arranged as 5'-A1-A2-B1-B2-3', or they may be arranged as 5' A1-B1-B2-A2-3'.

The invention contemplates that oligonucleotides bearing binding partners of a binding pair (or alternatively non-contiguous regions to which a bridge oligonucleotide may bind) may be located internally within the complex or they may be located at or near the terminal ends of the nucleic acid complex. Accordingly, in some instances, the oligonucleotide that is most 5' on the complex and the oligonucleotide that is the most 3' on the complex may each be linked to a member of a binding pair (e.g., first and second binding partners having affinity for each other). In similar embodiments, the 5' and/or 3' penultimate oligonucleotides in the complex may each be linked to a member of a binding pair. In these embodiments, the association of the binding partners will circularize or nearly circularize the complex. In these embodiments, the oligonucleotides linked to binding partners may or may not be additionally linked to another moiety such as an immobilization moiety such as biotin (see below). Transitions between associated and dissociated binding partners (and thus closed and open conformations, respectively) may be detected in a variety of ways including but not limited to gel electrophoresis. When gel electrophoresis is used, a transition from closed to open conformations (and vice versa) may be determined by a change in migration distance. Other ways of detecting transition between closed and open conformations (and vice versa) include but are not limited to optical tweezers, magnetic tweezers, tethered particle motion, a centrifuge force microscope as described in published PCT patent application WO2011/153211, atomic force microscopy (AFM), and light microscopy. As an example, if optical tweezers are used, the complex can be designed such that the most 3' oligonucleotide could be linked to one substrate (such as a bead) and the most 5' oligonucleotide could be linked to another substrate (such as a glass coverslip). Changes in length resulting from a change in binding between binding partners can be observed as a change in distance between the two substrates (e.g., between the bead and the coverslip). It is to be understood that the invention contemplates measuring binding changes (and thus changes in length of the complex) in the presence of an external force (e.g., under tension) or in the absence of such force. Still other approaches contemplated by the invention include directly detecting changes in length using single molecule fluorescence imaging, detecting changes in the average rheological properties of a solution of the complexes of the invention, and monitoring changes in hydrodynamic radius using dynamic light scattering.

The invention further contemplates the use of a DNA crosslinking agent to increase the strength of the complex. DNA crosslinking agents are known in the art and include without limitation psoralen. The complexes may also be exposed to crosslinking irradiation. In some embodiments, the crosslinked complexes may less likely to dissociate themselves when under tension or under other conditions that are intended to test the affinity of binding partners linked thereto. In still other instances, the invention contemplates crosslinking amino acid based moieties such as certain binding partners (e.g., to the complex). Protein crosslinking agents are known in the art and include without limitation NHS-diazirine (SDA).

The invention also contemplates labeling of the nucleic acid complex, the scaffold nucleic acid, any of the plurality of oligonucleotides, and/or the binding partners linked thereto. Labeling intends that any of these components are linked to a moiety that may be used to immobilize (permanently or transiently), detect, manipulate and/or modify. Moieties that are used to immobilize are described herein, are known in the art, and include without limitation biotin and avidin or derivatives thereof. Moieties that are used to detect are often times referred to as detectable moieties. Such moieties are also known in the art, and they include without limitation fluorophores, chromophores, radioisotopes, magnetic particles, enzyme substrates, and the like.

The complexes of the invention, in some instances, comprise oligonucleotides that are linked to a binding partner such as for example an antibody or an antigen (and may be referred to herein as modified oligonucleotides). The linkage between the oligonucleotide and the binding partner may be covalent or non-covalent depending on the strength of binding required for a particular application. These modified oligonucleotides may be generated by first incorporating a reactive group (or moiety) into the oligonucleotide, preferably at or near one of its ends, and then reacting this group (or moiety) with the binding partner of interest which may or may not be modified itself. An example of such a conjugation protocol is provided herein. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group is amenable to the methods of the invention, provided it participates in an interaction of sufficient affinity to prevent dissociation of the binding partner from its oligonucleotide.

It is to be understood that the scaffold nucleic acid and the oligonucleotides of the invention may be DNA or RNA in nature, or some combination thereof, or some analog or derivative thereof. The term nucleic acid refers to a polymeric form of nucleotides of any length, including deoxyribonucleotides, ribonucleotides, or analogs thereof. In some embodiments, the nucleic acids will be DNA in nature, and may optionally comprise modifications at their 5' end and/or their 3' end.

In some embodiments, the binding partners may include without limitation antibodies (or antibody fragments) and antigens, receptors and ligands, aptamers and aptamer receptors, nucleic acids and their complements, and the like.

Methods of Use

The nucleic acid complexes of the invention, including single-molecule linkers or complexes, can be used in myriad applications, including for example, measuring the kinetics of molecular interactions, identifying molecular binding partners (from a known or unknown candidates), and encrypting and decrypting information. Various additional aspects of the invention are described below.

Various methods of the invention detect changes in binding based on a change in length of the complex. As described herein, changes in length may be measuring using any number of methods including but not limited to gel electrophoresis, single molecule force probes such as optical tweezers, magnetic tweezers, tethered particle motion, atomic force microscope (AFM), centrifuge force microscopy (CFM), and single molecule fluorescence imaging.

Competitive binding assays to measure molecular/chemical kinetics. Some aspects of the invention provide methods of measuring the kinetics of molecular interactions using the nucleic acid complexes described herein. As described above, a nucleic acid complex can exist in one of two conformational states: bound or unbound. These conformational states may be referred to as closed and open, respectively. As an example, a nucleic acid complex that comprises a pair of binding partners having specificity to each other (e.g., ligand and receptor) is in its open state if the binding partners do not bind to each other and the scaffold nucleic acid remains linear. A nucleic acid complex is in its closed state if the binding partners bind to each other and the scaffold nucleic acid forms a looped conformation. By monitoring the change in these states, the kinetics of the binding interaction between the binding partners can be determined. In some embodiments, the conformational state can be resolved on an electrophoretic gel, as described elsewhere herein. In other embodiments, the conformational state can be resolved using single-molecule force probes, including but not limited to optical tweezers, magnetic tweezers, tethered particle motion, atomic force microscopy (AFM), centrifuge force microscope (CFM). In other embodiments, the conformational state can be observed directly using single-molecule fluorescence imaging.

The following protocol can be used to measure the kinetics (e.g., off-rate) of molecular binding partners on a linker: 1) providing a nucleic acid complex that comprises two binding partners (e.g., A and A') bound to each other (i.e., in a closed conformation), 2) add excess of a soluble form of one binding partner (A) that will bind to its binding complement (A') when the A-A' bound to the complex dissociate from each other, essentially fixing the dissociated complex in an open conformation, 3) determine the conformational state of the complexes over a period of time in order to determine the off-rate of the A-A' interaction. With time, the closed conformation will convert to the open conformation. The rate at which that conversion occurs is an indicator of the strength of binding between those binding partners. The soluble form of the binding partner (A) may be present at a 2-fold, 3-fold, 5-fold, 10-fold, 50-fold, 100-fold, or more excess over the amount (or concentration) of the complex-bound form of the binding partner (A).

Figure 8:
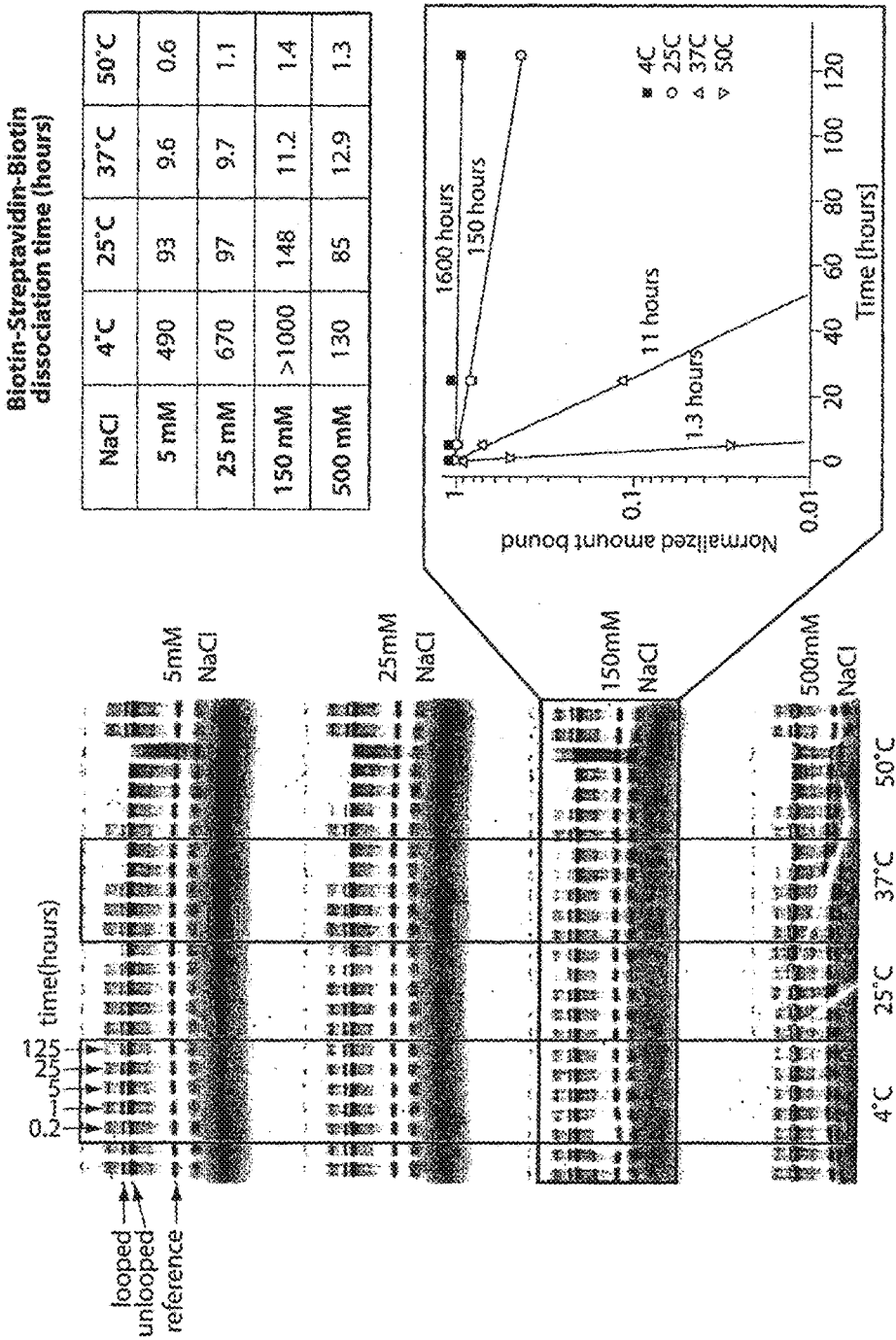
FIG. 8. Biotin-Streptavidin-Biotin dissociation kinetics. An array of 16 different experimental conditions were tested on a single 96-well gel. Each of four combs has a different salt, and within each comb are experiments at four temperatures. Dissociation was measured at 5 different times: 0.2, 1, 5, 25, and 125 hours. An expanded view of one salt condition shows widely varying off-rates with temperature. The resulting data are summarized in the table, showing time constants ranging from less than 1 hour to over 1000 hours.

FIGS. 7 and 8 demonstrate the formation of looped constructs. FIG. 7D, for example, illustrates the formation of looped constructs having two biotins in the presence of streptavidin (t=0). Excess biotin was added at various times in order to quench the re-formation of looped constructs following their natural dissociation under the particular conditions. These data can be used to determine the on-rate, and thus also the dissociation constant Kd, of binding pairs such as biotin and streptavidin. Preliminary analysis of these particular data yields a Kd on the order of $10^{-14}$, which is the same as reported in the literature.

Figure 6A:
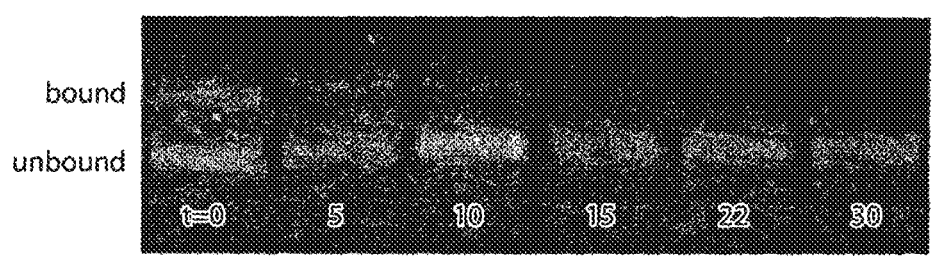
FIG. 6. (A) is a photograph of an electrophoretic gel showing the bound and unbound conformations in the presence of psoralen at various times. (B) is a graph of the fraction of complex that is bound (or looped) as a function of time. (C) is a photograph of an electrophoretic gel showing the closed conformation of a complex comprising digoxin and anti-digoxigenin binding partners (left lane) and the loss of the closed conformation upon addition of excess anti-digoxigenin antibody.
Figure 6B:
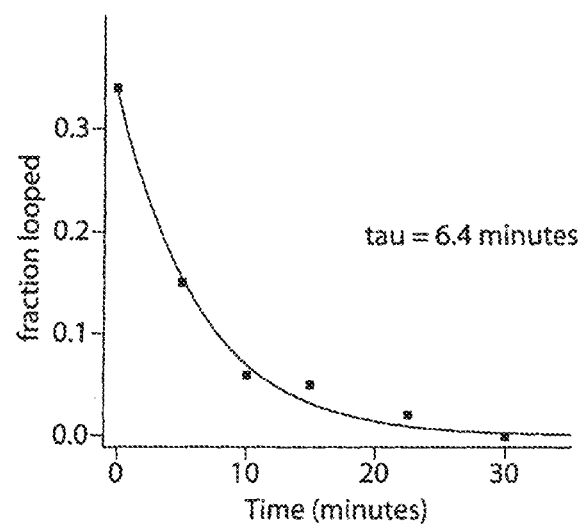

FIGS. 6A and B show the results of an assay using an excess of bridge oligonucleotide. The excess bridge oligonucleotide competes with the hybridized bridge oligonucleotide for binding to the complex. This experiment was carried out at elevated temperature in order to accelerate the kinetics. The bridge oligonucleotide was 50 nucleotides in length. The competition assay could also be carried out using excess oligonucleotide that is complementary to the bridge oligonucleotide.

Figure 6C:
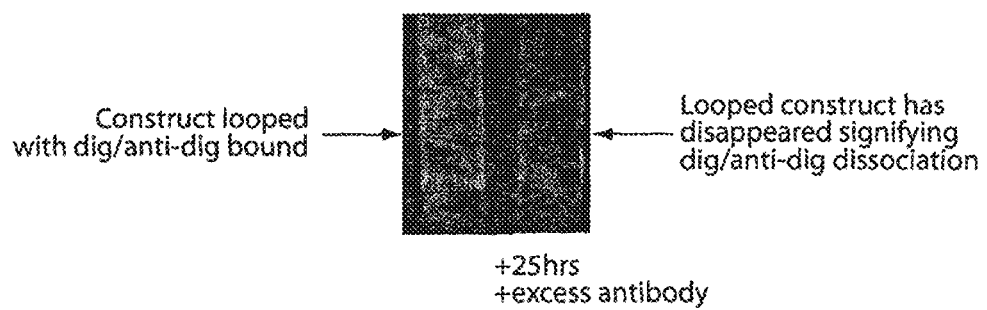
Figure 7A:
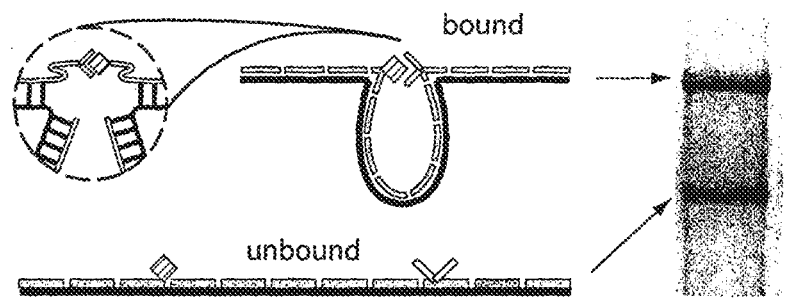
FIG. 7. Demonstration of molecular kinetics with a nanoswitch. (A) The DNA nanoswitch has two distinct states, depending on the binding of a receptor-ligand pair, that can be distinguished by gel electrophoresis, (B) In the presence of excess ligand, a nanoswitch in the bound state will become trapped in the unbound state upon dissociation. (C) Dissociation of biotin-streptavidin at 50° C. and 150 mM NaCl causes the amount of looped product to decrease over time (see gel image). The amount of looped construct is quantified from the gel to determine the kinetics of dissociation. (D) Looped constructs comprising two biotin oligos were made in the presence of streptavidin (t=0), followed by quenching in the presence of excess biotin at various time. These data can be used to determine on-rate and dissociation constant Kd.
Figure 7B:
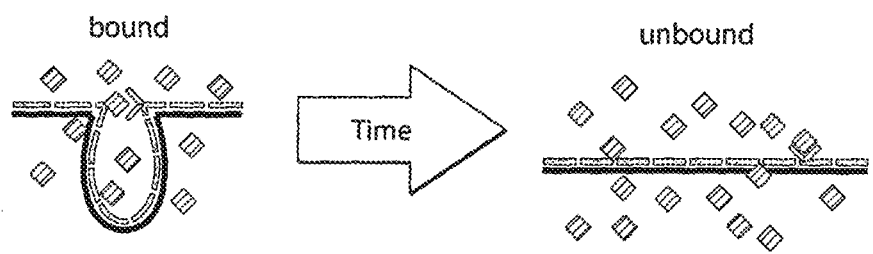
Figure 7C:
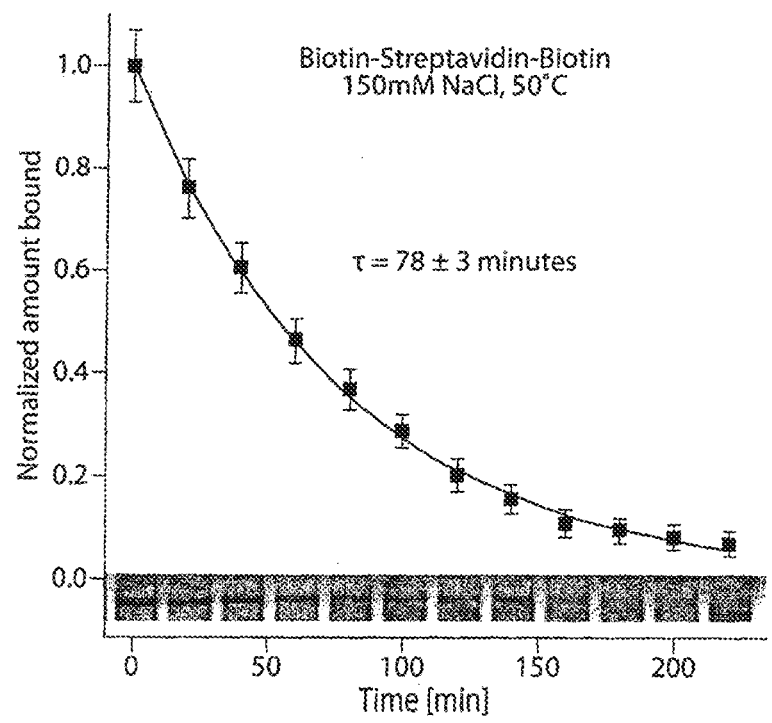
Figure 7D:
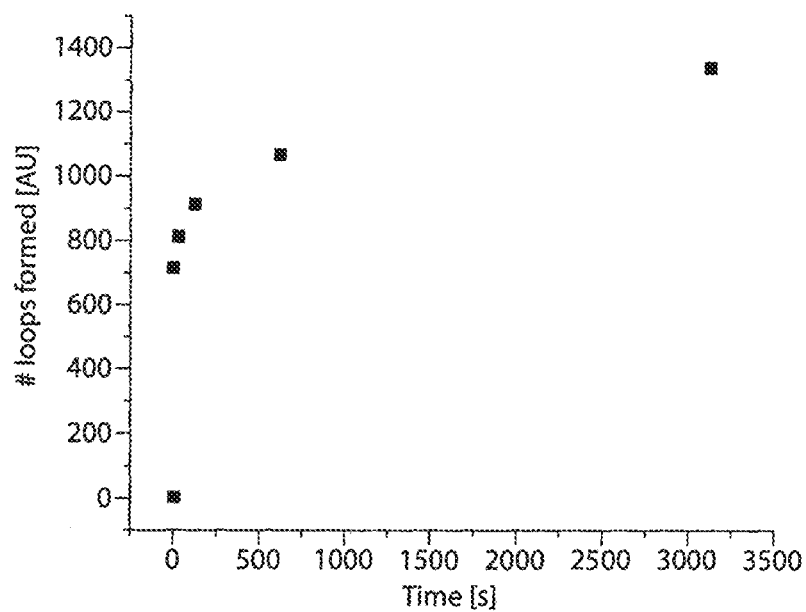

FIG. 6C shows the results of an assay using an excess of antibody. In this assay, the binding partners bound to the complex are digoxin and anti-digoxigenin antibody. In the absence of excess anti-digoxigenin antibody, the closed complex is formed, as shown by the presence of a band in FIG. 6C (left lane). In the presence of excess anti-digoxigenin antibody, the complex converts to an open state as indicated by the loss of the band corresponding to the closed state, as shown in FIG. 6C (right lane).

In some embodiments, the protocol may include the use a photoactive crosslinker such as psoralen to preserve the complex conformation at different times prior to sampling. Crosslinking provides a "snapshot" of how much of the complex is in a bound/closed state at any given time and may be necessary to preserve the conformation in instances where the kinetics are faster than the gel running time. Other photoactive or non-photoactive crosslinking agents can be used in the methods provided herein.

Internal mechanical force as a measure of force-dependent kinetics. Some aspects of the invention provide methods of measuring force-dependent kinetics of binding interactions using the nucleic acid complexes described herein by creating a force that is internal to the complex (rather than applying an external force as can be done using optical tweezers or magnetic tweezers, for example). This method takes advantage of "internal" mechanical forces that are created when a double-stranded nucleic acid is circularized. (Shroff et al. *Biophysical Society* (2008) 94:2179-86) Changing the length of a nucleic acid loop varies the internal force of the complex, with force increasing as the length decreases. For example, binding partners on a scaffold nucleic acid that are separated by approximately 200 to 300 nucleotides will easily bind to form a closed loop configuration because there is very little, if any, internal force created by the loop. On the other hand, the same binding partners when separated by shorter distances will less readily form a closed loop conformation (and when formed, may more readily dissociate) as the force imposed by the scaffold nucleic acid approaches, is similar to, and/or exceeds the binding strength between the binding partners.

The following protocol can be used to measure the force-dependent kinetics of binding partners on a complex: 1) provide a plurality of complexes, each complex within the plurality comprising the same binding partner pair, wherein the number of nucleotides separating the binding partners on a scaffold nucleic acid varies within the plurality, and 2) determine the presence of bound versus unbound complexes as a function of separating distance, using for example gel electrophoresis. It is expected that as the loop length decreases, the ratio of bound to unbound complexes will decrease also. In some embodiments, the protocol may include the use a photoactive crosslinker such as psoralen to "freeze" complex conformation at different times prior to sampling the complexes. Other photoactive or non-photoactive crosslinking agents can be used in the methods provided herein. In some embodiments, the protocol can include the initial formation of a loop that predominantly consists of single-stranded DNA. To generate tension within these loops, oligonucleotides complimentary to portions of the looped scaffold regions are added and allowed to hybridize to the scaffold, thereby generated a mechanical force upon hybridization and formation of double-stranded regions within the loop. The force can be therefore be precisely and finely varied in time and magnitude by varying the amount of double-stranded versus single-stranded nucleic acid in the loop. (Shroff, Liphardt et al., Nano Letters 2005.)

A similar approach may be taken using bridge oligonucleotides. Thus, in some embodiments, a nucleic acid complex comprises a bridge oligonucleotide that hybridizes to two non-contiguous sequences of the scaffold nucleic acid. In embodiments where the bridge oligonucleotides binds to non-contiguous regions of the linker, the distance between the non-contiguous sequences may be varied among the complexes such that the internal force of the closed loop configuration varies, accordingly.

In some embodiments, the number of nucleotides separating the binding partners, or separating the two non-contiguous sequences to which a bridge oligonucleotide binds, is at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 or more nucleotides. In some embodiments, the distance is 40-100 nucleotides. Suitable distances will vary based on the application and will depend on the size of the binding partners, the degree of single- and double-strandedness of the looped region, the use of linkers to attach the binding partners to oligonucleotides within the complex, and the like.

Analyte detection. Some aspects of the invention provide methods for detecting the presence of an analyte of interest in a sample using the nucleic acid complexes described herein. In these aspects, the complex comprises two binding partners that have specificity for the same analyte. The binding partners may be identical to each other, provided that they can both bind to the analyte simultaneously. As an example, they may be identical antibodies provided the antigen to which they bind has several epitopes that can be bound by the antibodies simultaneously without interference. The binding partners may be different from each other but have binding affinity for the same analyte. As an example, they may be antibodies that bind to different epitopes on the same antigen provided they can bind to the antigen simultaneously without interference. The bound and unbound conformation of the complex can be used to determine the presence and absence of an analyte in a sample, respectively. If the analyte is present, the binding partners that are attached to the scaffold nucleic acid will bind to the analyte to form a closed loop conformation. In the absence of the analyte, binding will not occur, and the complex will remain open.

The following protocol can be used to detect an analyte in a sample: 1) combine a sample with a complex comprising binding partners of the analyte (e.g., antibodies to the analyte), and 2) determine the conformation of the complex for example by gel electrophoresis. Detection of a closed loop conformation is an indication that the analyte is present in the sample and binds to the two binding partners bound to the scaffold nucleic acid. As described herein, in other embodiments, the conformational state can be resolved using single-molecule force probes, including but not limited to optical tweezers, magnetic tweezers, tethered particle motion, atomic force microscopy (AFM), centrifuge force microscope (CFM). In other embodiments, the conformational state can be observed directly using single-molecule fluorescence imaging.

Screening methods and identification of binding partners. Some aspects of the invention provide methods for screening a collection of nucleic acid based binding partners such as but not limited to aptamers for a target binding partner using the nucleic acid complexes described herein. By attaching a known moiety and a candidate binding partner to different regions of the scaffold nucleic acid, and determining whether a looped conformation is formed between the two, a binding partner to the known moiety can be identified. If the candidate binding partner is a true binding partner of the known moiety, then it will bind to the known moiety, and the complex will form a closed loop conformation. If the candidate binding partner has virtually no affinity for the known moiety, the complex will remain open.

The following protocol can be used to screen for binding partners on a complex: 1) provide a collection of complexes that comprise a known moiety (e.g., a target molecule) and a unknown candidate binding partner (e.g., an aptamer from a library of aptamers), and 2) determine the conformation of the complex at one or more times for example by gel electrophoresis. Detection of a closed loop conformation is an indication that the candidate binding partner has affinity for the known moiety. It is also possible to order a number of candidate binding partners based on their degree of affinity for the known moiety. In other embodiments, the conformational state can be resolved using single-molecule force probes, including but not limited to optical tweezers, magnetic tweezers, tethered particle motion, atomic force microscopy (AFM), centrifuge force microscope (CFM). In other embodiments, the conformational state can be observed directly using single-molecule fluorescence imaging.

Encrypting and decrypting information. Some aspects of the invention provide methods of encoding information using a binary approach that takes advantage of the two-state nucleic acid complexes of the invention. The invention contemplates methods for encrypting and decrypting information using these complexes and decrypting information. The methods provide an inexpensive and fast way to send secure messages over a public channel. Unlike similar DNA encryption methods that require specialized laboratory work (e.g., PCR, sequencing, cloning) that can take hours to days (Clelland C. et al. (1999) Nature 399: 533-534; Leier A. et al. (2000) Biosystems 57: 13-22; Tanaka K. et al. (2005) Biosystems 81: 25-29; Cui, G. et al. (2008) In Bio-Inspired Computing: Theories and Applications. p. 37-42), the invention enables encrypting and decrypting messages in minutes, requiring as little as disposable droppers and a no-prep buffer-less (even handheld) gel system (e.g., Invitrogen E-gel systems).

Figure 9A:
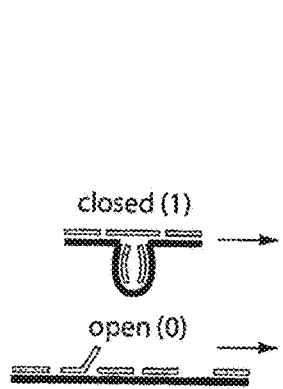
FIG. 9. DNA as a binary switch. The conformations of two-state DNA complexes can represent bits through open or closed states, representing 0 and 1 respectively. This concept was demonstrated with three different implementations: (A) a self-assembled construct with an addressable loop closure (Halvorsen, K. et al. (2011) Nanotechnology 22: 494005), (B) a switchable circular/linear construct, and (C) a double-stranded/single-stranded segment.
Figure 9B:
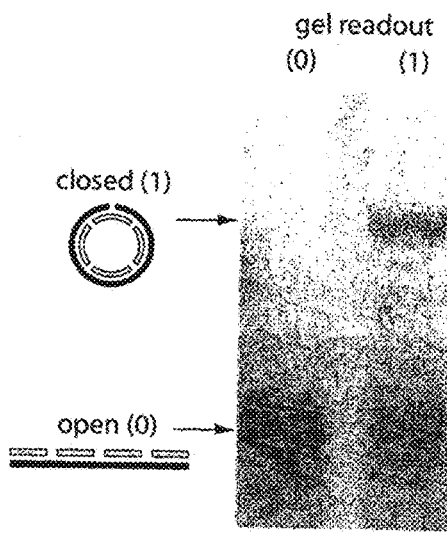
Figure 9C:
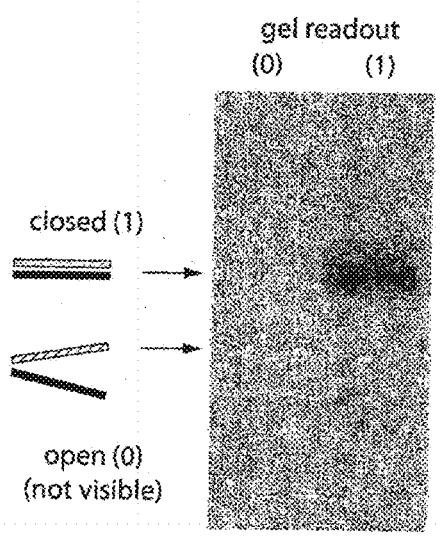

Binary data may be encoded in a number of ways. Three embodiments are shown in FIG. 9. FIG. 9A shows linear and looped structures that are visible and distinguishable in a gel. FIG. 9B shows linear and circularized structures that are visible and distinguishable in a gel. FIG. 9C shows single- and double-stranded nucleic acid fragments; only the double-stranded fragment is visible under certain situations. In each instance, addition of a single component triggers the nucleic acid complex to adopt a different conformation that is distinguishable and observable. In some embodiments, the complex is converted from an open structure to a closed structure, or from a closed structure to an open structure, or from a single-stranded to a double-stranded structure. The invention contemplates that messages may be encrypted in pools of nucleic acids and that such messages can be decrypted by the addition of one or more decryption keys (e.g., oligonucleotides or analytes). Any of the nucleic acid complexes of the invention may be used in an encoding system as described herein provided their transition between two different states can be triggered by the addition of key component (e.g., oligonucleotide or analyte) and that those two states are distinguishable.

The invention contemplates encoding information based a series of bits and bytes. Typically, each bit is a nucleic acid structure that can adopt one of two states depending on the presence (or absence) of a key component. The number of bits and bytes that may be used to encode information is limited only by the ability of the detection system to resolve the various structures. Each subset of bits corresponds to a byte. This is shown in FIG. 9. The Figure shows the use of 8 bits per byte. The bit is represented by a nucleic acid fragment that is either in single-stranded (and thus not visible) form or in double-stranded (and thus visible) form. Thus, the bits in this Example bits correspond to nucleic acid fragments that are 20, 22, 25, 28, 32, 37, 43 and 50 bases (or base pairs (bp) when in double-stranded form) in length. Each pool of nucleic acids will employ 8 bits (or fragments) for each byte of information, which in this example represents a particular letter. The message itself employs 11 bytes. The bits are designed in accordance with the invention to readout as either a 0 or a 1 (which correspond to open and closed states, or vice versa). Readouts are apparent after addition of a missing component. Each bit will have a key component. The information to be sent will be a function of the key components necessary to read the code. As with other encoded information systems, the key components may be sent to the intended recipient of the information separately from the encoded information. The key component for each bit may be one or more oligonucleotides or a fragment thereof, one or more analytes or a fragment thereof, or one or more scaffold nucleic acids that transform the state of the nucleic acid structure representing a bit. Key scaffold nucleic acids are long nucleic acids that bind to a plurality of single-stranded oligonucleotides. Key scaffold nucleic acids may or may not be based on the M13 genome.

In addition to the addition of a key component, readout can be controlled by varying the temperature, by interactions with light (Schafer C. et al. (2007) Journal of the American Chemical Society 129: 1488-1489), by applying mechanical force (Halvorsen K. et al. (2011); Quek S. et al. (2009) Nature Nanotechnology 4: 230-234), and the like. The state of these bits (0 or 1) can be decrypted quickly and unambiguously using gel electrophoresis, as shown in FIG. 9.

In greater detail, in some embodiments, each mechanical bit is formed by nucleic acid self-assembly processes and can be encrypted by omitting a critical component of its structure (e.g., a key single-stranded oligonucleotide or an analyte). In the absence of the key component, the bit may be reduced to an unstructured mixture of oligonucleotides or it may exist in a default state. The default state may be an open state or a closed state. As an example, the default state may be an open state that migrates a distance D in a gel and that is converted to a closed state that migrates a distance D' when combined with its respective key component. The default state may be an invisible state such as a single-stranded oligonucleotide that is converted to a visible state using, for example, gel electrophoresis and an intercalating dye. Messages encrypted as a collection of such bits are difficult to decipher because the 0 and 1 states for each bit are nearly indistinguishable mixtures of oligonucleotides. Decryption with a key is easily accomplished. For example, addition of the missing key may trigger self-assembly of a complex, or conversion of the complex from one state to another, or conversion from an invisible to a visible state.

In some embodiments, separation of each mechanical bit into two parts or two "keys" forms an asymmetric encryption system. This system has the "public key" property if the key is distributed physically because one key cannot be readily determined from the other without knowledge of the sequence.

In some embodiments, suitable countermeasures, such as adding "distractor" components such as distractor oligonucleotides or analytes or fragments thereof to the physical encryption key to obscure information, are contemplated and can make the identity of the decryption key (such as the nucleotide sequence of a decryption key oligonucleotide) difficult to obtain.

Figure 10:
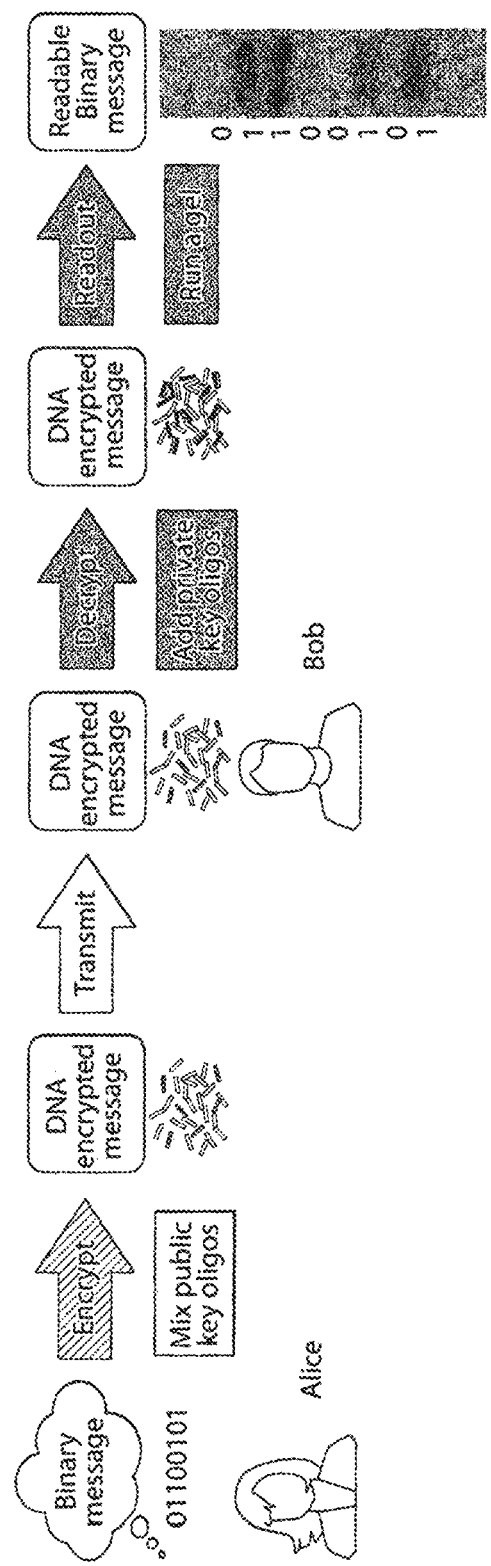
FIG. 10. Conceptualization of DNA encryption and decryption. A message is prepared by mixing together oligonucleotides that correspond to either a binary 0 or 1 for each bit. This mixture is sent to a recipient through a public channel. The recipient decrypts the message by adding the DNA decryption key. This causes the message to self-assemble, enabling rapid read out by gel electrophoresis.

As an example (described in detail in Example 3), consider how a sender (Alice) can send an encrypted message to a receiver (Bob) (FIG. 10) using the linear binary switch shown in FIG. 9C. In this instance, the receiver designs the system to be used by the sender to encrypt messages. The receiver therefore designs the nucleic acids corresponding to 1 and 0 for each bit as well as the decoding key oligonucleotide. The receiver maintains the decoding key (and thus it is private) but sends the 1 and 0 oligonucleotides to the sender. The sender then devises a message to be sent to the receiver using a combination of the 1 and 0 oligonucleotides. By choosing the 1 and 0 oligonucleotides for each bit, and optionally combining different bits in the same vial (e.g., fragments of differing length) to form a byte and then sending multiple bytes, the sender is able to transmit simple or complex encrypted messages to the receiver. The invention also contemplates methods in which the sender devises the encryption scheme and then sends the encoded message and the key oligonucleotide to the receiver (albeit, typically separately).

As noted above, different bits may be represented by different length oligonucleotides. In some embodiments, the DNA length can be 20, 25, 30, 35, 40, 45, 50, 55, 60, 65, 70, 75, 80, 85, 90, 95, 100, 200 or 300 nucleotides (or bases), or more including kilobases.

As an example, the receiver chooses bits corresponding to DNA fragment lengths of 20 nucleotides, 30 nucleotides and 40 nucleotides. The receiver then generates three equal length oligonucleotides for each bit (A, A' and B), two of which are complementary to each other and hybridize together (A and A') and one of which is inert (B) (see Example 3 for details of oligonucleotide design). For each bit, one of A or A' represents a 1 and the B represents a 0. Assuming that the receiver will keep A' as the key to unlock the encrypted message, separate vials of A and B are prepared and sent to the sender for use in making an encrypted message, wherein A and B represent the 1 and 0 values, respectively. Together, the A and B oligonucleotides for each bit are used to encrypt a binary based message. The sender then uses either A (for a 1) or B (for a 0) for each bit, mixes these in a single vial, and sends the mixture to the receiver over a public channel. The receiver decrypts the message by combining the oligonucleotide mixture with the private decryption key (in this example, the A' oligonucleotides for each bit) and running a gel.

Contemplated herein are encoding systems with equal or up to 3-bit, 4-bit, 5-bit, 6-bit, 7-bit, 8-bit, 9-bit 10-bit, 11-bit, 12-bit, 13-bit, 14-bit, 15-bit, 16-bit, 17-bit, 18-bit, 19-bit, 20-bit, 21-bit, 22-bit, 23-bit, 24-bit, 25-bit, 26-bit, 27-bit, 28-bit, 29-bit, 30-bit, 31-bit, 32-bit, 33-bit, 34-bit, 35-bit, 36-bit, 37-bit, 38-bit, 39-bit, 40-bit, 41-bit, 42-bit, 43-bit, 44-bit, 45-bit, 46-bit, 47-bit, 48-bit, 49-bit, 50-bit, 60-bit, 70-bit, 80-bit, 90-bit, 100-bit, 120-bit, 140-bit, 160-bit, 180-bit, 200-bit, 300-bit, 400-bit, 500-bit, 600-bit, 70-bit, 800-bit, 900-bit, 1000-bit, or 200-bit, or more storage capacity. Storage capacity could therefore range from 3-2000 bit, 3-1000 bit, 3-500 bit, 3-100 bit, 3-50 bit, 3-20 bit, or 3-10 bit capacity. Increasing storage capacity to 40 bits would enable storage of the ubiquitous 12 digit Universal Product Code (UPC).

Unlike encryption schemes that rely on mathematical algorithms, this method is not directly vulnerable to increasing computational power. Unauthorized decryption would require the physical generation and testing of approximately $4^N$ possible decryption keys, or 10,155 for a simple 8-bit encoding scheme (with an approximately 1 in 1063 chance of guessing a decryption key if there is an allotted 25% mismatched bases (Leier A. et al. (2000) Bio systems 57: 13-22; Lee I. et al. (2004) Nucleic Acids Research 32: 681-690). In addition, the number of possible decryption attempts is limited by the amount of physical material available within the encrypted message.

Attempts to crack the code can be further deterred with a two pronged approach: (1) limiting access to physical information about the message (e.g., the oligonucleotide sequences) and (2) making this physical information difficult to decipher. In some embodiments, one or more distractor strand are introduced into the physical mix. As used herein, a distractor strand may refer to an oligonucleotide of similar length and composition as the encoding strands but with different sequences (Leier A. et al. (2000); Gehani A. et al. (2004) DNA-based Cryptography. Aspects of Molecular Computing p. 34-50). These distractor strands can increase the time and effort required to obtain the sequences of the encoding oligonucleotides within the encrypted mixture, compounding the challenge already presented by the short lengths of the encoding oligonucleotides (Oberacher H. et al. (2004) Journal of the American Society for Mass Spectrometry 15: 32-42; Oberacher H. et al. (2009) Biopolymers 91: 401-409; Farand J. et al. (2009) Analytical Chemistry 81: 3723-3730), and the presence of multiple oligonucleotide populations. The presence of multiple "false" encryption keys also makes the true encryption key much more difficult to determine, even if the sequence could be obtained from the limited material in the sample. If the encryption key is private, this approach is very effective as the sender could in fact encode false messages into the mixture with distractor strands, and the attacker would have little way to identify the true message without knowledge of the decryption key sequence. The ease of decryption decreases (thereby impeding an unauthorized recipient) with the addition of a greater number of distractor strands and more bits per message encoded. In some embodiments, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 5000, or more distractor strands (or mixtures of distractor strands) may be added to the encryption vials. The number of distractor strands therefore may be in the range of 1-5000, 1-1000, 1-500, 1-100, or 1-10 without limitation. Distractor strands could be synthesized by automated methods or they could be fragments of genomic DNA that are optionally size fractionated to arrive at fragments of suitable lengths. In some embodiments, additional security can be obtained by modifying the ends of the oligonucleotides to prevent the chemical conjugation required for some sequencing techniques and profiling techniques, or by using other chemical modifications.

It is to be understood that the foregoing illustrates a simple encryption system that relies on the formation of double-stranded nucleic acid fragments (upon addition of a decryption key) and then visualization of the double-stranded nucleic acid fragments by virtue of their uptake of intercalating dyes (which typically do not bind effectively to single-stranded nucleic acids). However, the invention contemplates more complex systems that employ the open and closed conformations shown in FIGS. 7A and B. The invention also contemplates methods other than gel electrophoresis to view and/or decrypt encoded messages. For example, microarrays may be used in which each of the decryption strands for each bit is located in a different well.

Additional applications of these methods beyond information security (secure messaging) are also contemplates and include without limitation authentication and barcoding. The invention therefore contemplates the use of these methods for authentication, brand protection, and/or source tracking of any number and variety of items such as but not limited to legal documents such as personal identification documents (e.g., driver's licenses, passports, and the like), wills, commercial goods including high cost goods (e.g., clothing, accessories, handbags, jewelry, etc.), pharmaceuticals, cigarettes, antique or vintage items or other rare items (e.g., sports memorabilia, art works, paintings), and the like. In the case of pharmaceuticals, the barcode may convey information about lot numbers, productions sites, production dates, expiry dates, and the like, and in this way can counter any secondary market for such goods. In the case of personal identification documents (e.g., driver's license, passports) printed with DNA markers as additional prevention against fraud or identity theft, using one's own genomic DNA as an authentication key is also contemplated by the invention.

The encoded nucleic acid mixture may be provided as a separate vial or may be applied directly to the good or product. Several methods have been demonstrated for storing printed DNA on paper (Kawai J. et al. (2003) DNA book. Genome Research 13: 1488-1495; Hashiyada M. et al. (2004) The Tohoku Journal of Experimental Medicine 204: 109-117).

Force-Measuring Technologies

As discussed herein, various methods of the invention involve detecting interactions between binding partners by detecting changes in length of the nucleic acid complexes. Binding interactions, changes in complex length, transitions from open to closed (or closed to open) conformations, and kinetic modifications, inter alia, may be detected or determined using a number of methodologies including but not limited to gel electrophoresis, atomic force microscopy (AFM), optical tweezers, magnetic tweezers, tethered particle motion, centrifuge force microscopes (CFM), mechanical cantilevers, and the like. These methodologies are known in the art and some are described briefly below. It is to be understood that any of these methodologies can be used in conjunction with the various methods provided herein.

Atomic force microscopy. The force between two binding partners on a linker can be measured by atomic force microscopy (AFM) or scanning force microscopy (SFM). In some embodiments, AFM can be used to measure single molecule linker stretching and rupture forces. In some embodiments, the force measured may be on the order of a few picoNewtons (pN). In some embodiments, AFM is performed with either static or dynamic modes.

Optical tweezers. The force between two binding partners on a linker can be measured using optical tweezers (also referred to as a "single-beam gradient force trap"). Optical tweezers use a highly focused laser beam to provide an attractive or repulsive force (typically on the order of pN), depending on the refractive index mismatch, to physically hold and move microscopic dielectric objects, such as nucleic acids. In some embodiments, optical tweezers are used to manipulate a linker by exerting extremely small forces via a highly focused laser beam.

In some embodiments, optical traps can be used to detect nucleic acid displacement as a measure of molecular force. The optical trap may be used herein to manipulate and study single molecule linkers by interacting with a bead that has been attached to the linker.

Magnetic tweezers. The force between two binding partners on a linker can be measured using magnetic tweezers (MT). Magnetic tweezers exert force and torque to a molecule such as a nucleic acid complex of the invention. The extension of a molecule corresponds to its response to the applied stress. In some embodiments, a single linker is attached at one end to a tethering surface and at the other to a magnetic microparticle. The magnetic tweezers apparatus is equipped with magnets that are used to manipulate the magnetic particles whose position is measured with a video microscopy.

Centrifuge force microscopy. The force between two binding partners on a linker can be measured using centrifuge force microscopy (CFM). CFM exerts force to a molecule such as a nucleic acid complex of the invention using centrifugal force. The extension of a molecule corresponds to its response to the applied stress. In some embodiments, a complex is attached at one end to a tethering surface and at the other to a particle that can be visualized using for example light microscopy. The position of the particle and its movement relative to the tethering surface may be observed and measured as a function of the centrifugal force applied to the complex.

Other mechanical force-measuring technologies may be used with the embodiments described herein, for example, mechanical cantilevers, and the like.

EXAMPLES

Example 1

Switchable Single Molecular Linkers

Materials and Methods

Linker design and construction: All oligonucleotides were purchased from Bioneer, Inc., with the exception of the 5' double-biotin oligonucleotide (Integrated DNA Technologies), the digoxigenin oligonucleotides (Integrated DNA Technologies), and a few plain oligonucleotides ordered with next-day service (Invitrogen).

Figures 1, 1A, 2, 3, 4:
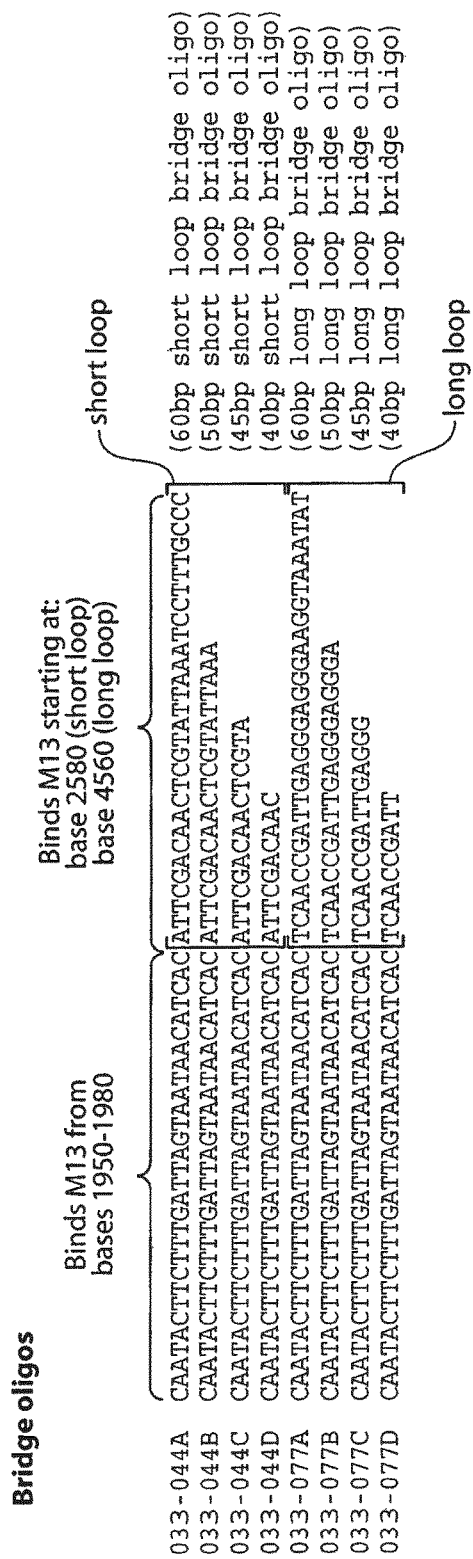
FIG. 1A. Sequences of all oligonucleotides used. The numbered oligonucleotides cover the entire sequence of the M13 scaffold strand, and the lettered strands are functionalized or special purpose oligonucleotides. The bridge oligonucleotides are labeled red for regions that bind M13 bases 1950-1980, green for regions that bind starting at M13 base 2580, and blue for regions that bind starting at M13 base 4560. Oligonucleotides numbers 001-121 (corresponding to SEQ ID NOs. 1-121) are those used to form the nucleic acid complexes of the invention. These oligonucleotides span the entire length of the M13 template. The nucleotide sequence of the M13 template can be found in US Patent Application Publication 20070117109 and in Rothemund P. W. K. (2006) Nature 440: 297-302. Oligonucleotide numbers 000A, 001A, 033A, 044A and 121A correspond to SEQ ID NOs. 122-126, respectively. Oligonucleotide numbers 033-044A-D and 033-077A-D correspond to SEQ ID NOs. 127-134, respectively.
FIG. 4. Single-molecule force spectroscopy results for the rupture of (left) DNA hybridization and (right) antibody-antigen interactions. Left: rupture force histogram for shearing a 20 bp DNA segment, demonstrating the filtering of erroneous data via the looped linker molecular signature. Right: survival trajectory for digoxigenin against its antibody under constant force, with results of maximum likelihood estimation superimposed.
Figure 1B:
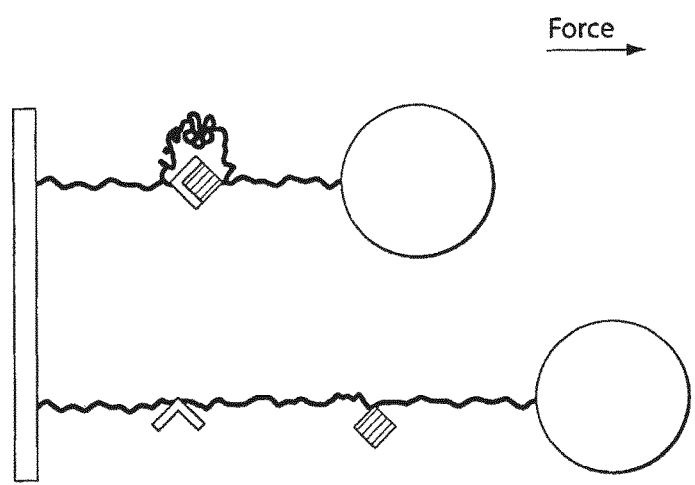
FIG. 1B. Single-molecule linking geometries: a cartoon showing receptor-ligand unbinding using a looped linker.

The full sequence of all the oligonucleotides used are shown in FIG. 1A and are based on the M13 sequence given by New England Biolabs and used for previous DNA origami work. The oligonucleotides are stored at 100 µM at −20° C., and all mixing of oligonucleotides is done at these stock concentrations unless noted. We will refer to the numbering throughout this section as we explain the construction of the various linkers.

Two different kinds of linkers were designed and assembled based on techniques outlined from previous DNA origami work (Rothemund P. W. K. (2006); Douglas S. M. et al. (2009)). Both linkers incorporate functional 'sticky' ends (we used double biotin on both ends) which act as anchors for single-molecule experiments, as well as two functional sites near the middle of the linker to form the loop. One set of constructs forms the loop by hybridizing a single 'bridge' oligonucleotide across two distinct locations, while the other set used two separate oligonucleotides each functionalized with digoxigenin or anti-digoxigenin, which can bind to each other as a receptor-ligand pair to form the loop.

To make these linkers, M13mp18 single-stranded DNA (New England Biolabs) was first linearized by hybridizing a 40-nucleotide oligonucleotide to form a double-stranded region and then cleaving this region with BtsCI restriction enzyme (New England Biolabs). The linearized single-stranded DNA was then mixed with complimentary oligonucleotides (Bioneer, Inc.) and subjected to a temperature ramp from 90 to 20° C. with a 1° C. min$^{-1}$ ramp in a PCR machine (Bio-Rad) to allow the oligonucleotides to anneal properly. For the linker with the bridge oligonucleotide formed loop, 121 oligonucleotides excluding the bridge oligonucleotides were added in tenfold molar excess, with the bridge oligonucleotides added in equimolar concentration to the scaffold strand. For the receptor-ligand loop construct, 120 oligonucleotides excluding the antibody oligonucleotide were in tenfold molar excess, which was added in equimolar concentration and subjected to a temperature ramp from 40 to 10° C. with a 0.5° C. min$^{-1}$ ramp after the other 120 were linked.

A more detailed protocol for looped linker construction is as follows:

Step 1: Single-stranded DNA (ssDNA) linearization. (1) Mix the following in a clean PCR tube: 5 µL M13mp18 ssDNA (NEB product N4040S D 0.25 mg/mL or 100 nM), 2.5 µL 10× buffer 4 (NEB), 0.5 µL 100 µM cut-site oligonucleotide (oligo 000A), and 16.5 µL water. (2) Briefly bring to 95° C. (30 seconds), lower to 50° C., and add 1 µL BtsCI enzyme. (3) Incubate for 1 hour at 50° C. (4) Heat deactivate the BtsCI enzyme by incubating at 95° C. for 1 minute.

To assay the linearization efficiency, add 1.21 µL of a mixture of all numbered oligonucleotides to 5 µL of linearized ssDNA and construct the double-stranded DNA (dsDNA) piece by heating to 90° C. and cooling to 20° C. at 1° C./minute or slower. The product can either be run on a 0.7% agarose gel to separate circular from linear, or the strand can be cut with a single cut enzyme (we added 1µ AfeI) to make sure most or all of the ssDNA was linearized.

Step 2: Conjugating protein to oligo. The protocol we used for conjugating protein to oligonucleotide was loosely based on the Pierce protocol provided with the sulfo-SMCC. (1) Deprotect the SH oligonucleotides by mixing the following in a clean PCR tube: 5 µL 0.5M TCEP (Pierce), 40 µL water, and 5 µL oligo 033A at 100 µM. Let the mixture sit for at least 30 minutes at room temperature. (2) Make 10 mM Sulfo-SMCC solution as follows: add 20 µL DMSO to 2 mg Sulfo-SMCC and pipette up and down to mix well, dilute into 450 µL of PBS, and use immediately. (3) Activate the protein as follows: suspend protein in PBS at 1 mg/ml concentration (use desalting column or centrifuge filter if necessary to concentrate or change buffer), use 20× molar excess of Sulfo-SMCC for 1 mg/ml protein (e.g., 1 mg/ml Antibody-20×: 20 µL protein @6.7 µM+0.27 µL Sulfo-SMCC @10 mM), and react for 30 minutes at room temperature. (4) Wash TCEP from oligonucleotides just before Sulfo-SMCC reaction is finished as follows: use QIAGEN® PCR clean up kit, following the protocol except eluting into 50 µL PBS for 10 µM final concentration. (5) Wash the Sulfo-SMCC from the activated protein as follows: pre-equilibrate a ZEBA™ desalt column (Pierce) with PBS, complete one or two passes of the protein through the column to eliminate Sulfo-SMCC, and re-suspend at 5 µM concentration. (6) Mix the activated protein with the de-protected oligonucleotides as follows: use 1:1 molar ratio or excess of protein (e.g. 1:1-2 µL oligonucleotide @10 µM+4 µL antibody @5 µM), and react for 30 minutes at room temperature.

Step 3: Purifying protein conjugated oligo. Once the protein has been conjugated to the oligonucleotides, it may be necessary to purify the conjugated oligonucleotide from unreacted byproducts depending on the yield of the reaction. We were typically able to get 5-50% yields, and even with a 50% yield we had trouble getting the loop to form with the digoxigenin antibody complex without purification. This is probably due to unconjugated oligonucleotides competing with the conjugated ones and due to excess protein reacting with dig-labeled oligonucleotides on the DNA construct.

To purify, the same product was run in a 4-20% polyacrylamide gel (Bio-rad) enough to separate the conjugated and unconjugated oligonucleotides (FIG. 3B), typically 150V for 40 minutes in 1× Tris/Borate/EDTA (TBE) buffer. The gel was then stained for 10-15 minutes in a 1× solution of Sybr Gold (Invitrogen) and used a razor blade to cut out the relevant band(s). Once the gel slices were cut, an electroelution kit and supplied protocol was used to extract the conjugated oligonucleotides from the gel. Briefly, the slices were placed in a midi sized electroelution tube (Gerard biotech) with 600 µL of buffer, and ran them in a horizontal electrophoresis at 150V for an additional hour. The final concentration was estimated based on the known amount of oligonucleotide put into each gel lane, the conjugation yield, and the amount of dilution in the electroelution step.

Step 4: Assembly of DNA linkers. Several different linkers have been made over the course of this study. All of these utilize the same basic protocol which was adapted from other DNA origami work (Rothemund P. W. K. (2006)) without further optimization. This involves mixing the oligonucleotides with the M13 ssDNA (typically in a 10× molar excess) and subjecting the mixture to a temperature ramp from 90° C. to 20° C. at 1° C./minute. This protocol may be slower than necessary, as it was based on folding complex 2D shapes rather than simply making a linear piece of dsDNA as we are doing here. A thermal cycler was used to apply the temperature ramp, but heating a water bath and letting it cool to room temperature over the same time provides the similar results.

The following mixtures of oligonucleotides were used in the construction of various linkers: (a) for plain linear, mix of all numbered oligonucleotides; (b) for linear with double biotin ends, mix of all numbered oligonucleotides except substitute 001A for 001 and 121A for 121; (c) for short loop with double biotin ends, same mixture as linear with double biotin ends, but do not include 033 or 044 (or use truncated versions of 033 and 044 to ensure all bases of M13 are paired); (d) for long loop with double biotin ends, same mixture as linear with double biotin ends, but do not include 033 or 077 (or use truncated versions of 033 and 077 to ensure all bases of M13 are paired).

To make the desired construct, mix the following in a clean PCR tube and apply the temperature ramp to anneal oligonucleotides: 5 µL of linearized ssDNA from above, 1.2 µL of one of the above mixtures (for 10:1 oligo:DNA ratio). For looped constructs, additionally add: (a) 1 µL of 1000× dilute digoxigenin oligo 044A for dig-antibody construct (b) 1 µL 1000× dilute bridge oligo 033-044B for short loop with 50 bp oligonucleotide bridge (c) 1 µL 1000× dilute bridge oligo 033-077B for long loop with 50 bp oligonucleotide bridge.

The temperature ramp completes the protocol, except for the dig-antibody construct. For the dig-antibody looped construct, add an additional 1 µL of purified antibody conjugated oligonucleotide at an approximate concentration of 100 nM once the first temperature ramp is complete. Note that if a larger volume of lower concentration oligonucleotide is used, it is important to maintain the proper buffer conditions for hybridization. Additional concentrated buffer may need to be added in this case. To anneal this oligo, we used a temperature ramp from 40° C. to 10° C. at 0.5° C./minute, though we did not exhaustively test simpler or shorter protocols. For the looped constructs, we typically got a 50% looping yield following this protocol. This looped product can be excised and purified from a gel as we did with the antibody conjugated oligo, but we did not find this purification step to be necessary for this study.

DNA-Protein conjugation: A 3' thiol-modified oligonucleotide was reduced and linked to monoclonal and polyclonal anti-digoxigenin (Roche Applied Science) using sulfo-SMCC (Pierce) and the accompanying protocol. The NHS group on the SMCC was first linked to free amines on the antibody (at 1 mg ml-1) with a 30 min reaction at room temperature using 20-fold molar excess of SMCC in PBS at pH 7.4. At the same time, the thiol oligonucleotide was deprotected and reduced by incubating in 50 mM TCEP (Pierce) for 20 min and then cleaned using a PCR clean up kit (Qiagen). Following the first SMCC reaction, excess SMCC was removed with a Zeba desalting column (Pierce), pre-equilibrated with PBS buffer. The activated protein was then mixed with the reduced thiol oligonucleotide in a 1:1 molar ratio for 30 min at RT.

Figure 3B:
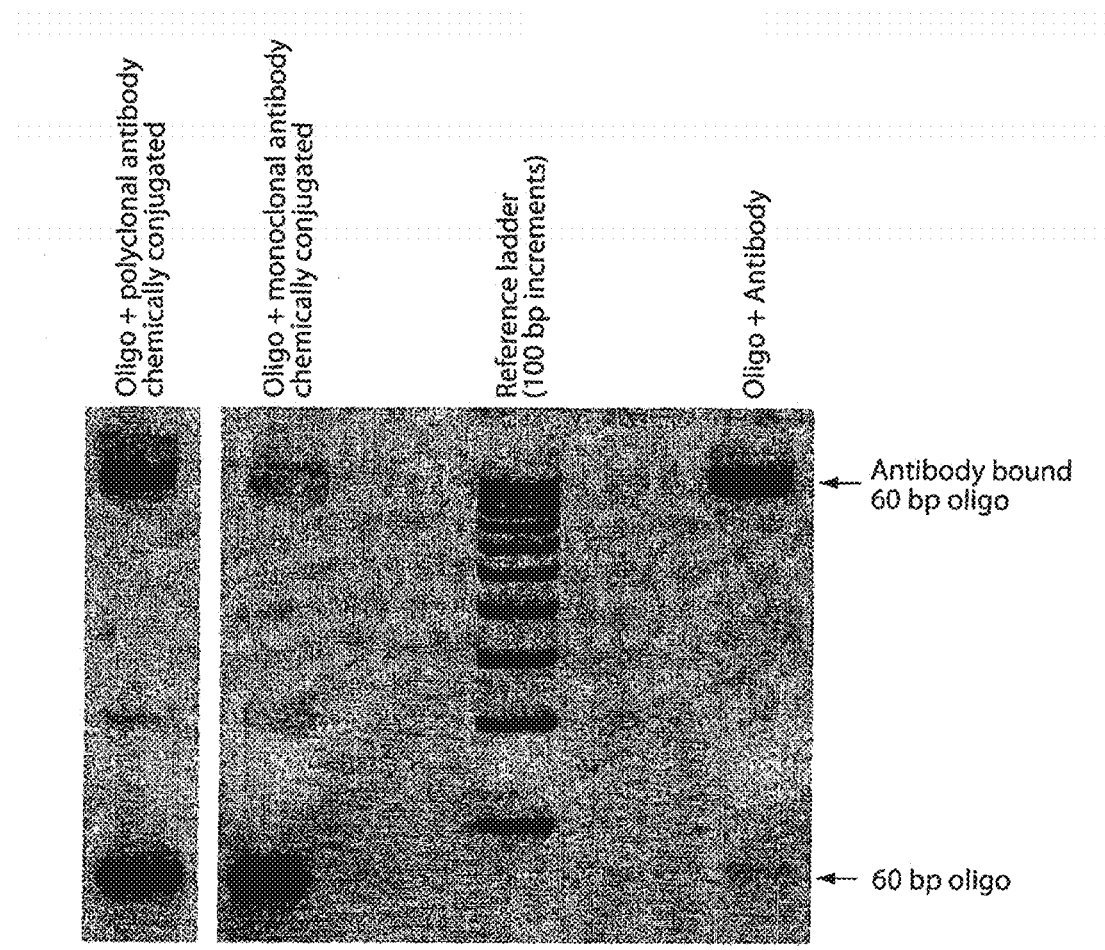
FIG. 3B. Gel verification of antibody-oligonucleotide conjugation. The left hand lanes show chemical conjugation of the oligonucleotide with polyclonal and monoclonal antibody, respectively. The right hand lane is a mixture of digoxigenin labeled oligonucleotide and anti-digoxigenin without chemical conjugation.
Figure 4:
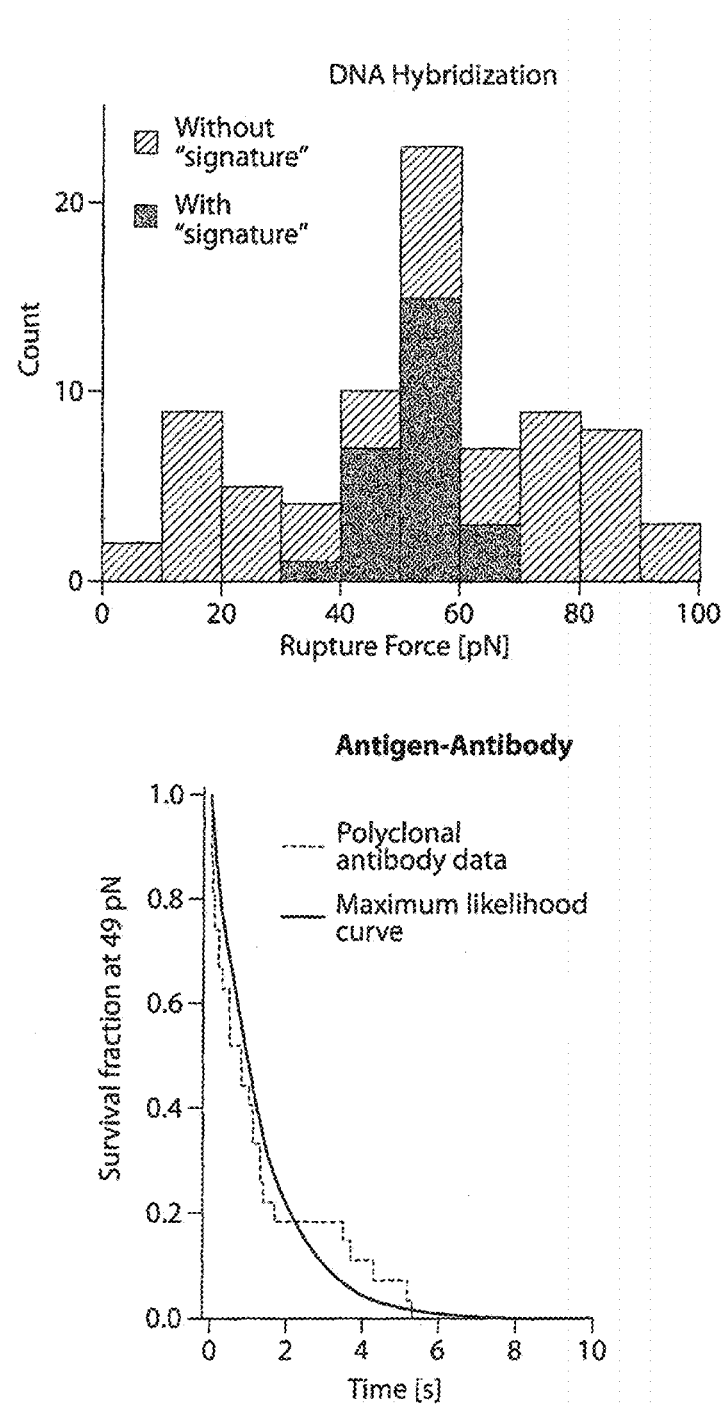

Conjugation was verified by visualization on a 4-20% polyacrylamide gel (Bio-Rad) run in 1×TBE buffer at 150 V for 40 min, where a shift from the protein linkage was readily apparent (see FIG. 3B). Typically, 5-50% of the oligonucleotides were conjugated to protein, and purification of the protein-DNA conjugate was accomplished by excising the gel band and using an electro-elution kit with the accompanying protocol (Gerard biotech).

Single-molecule force spectroscopy: The final unpurified linkers with double-biotin ends were incubated with streptavidin polystyrene beads (Corpuscular) for 15 min, and then injected into a chamber with PBS buffer for use in the optical trap. The optical trap setup consists of a single stationary trap and a piezo-controlled micropipette integrated into an inverted light microscope (Nikon). The setup is functionally identical to previously described instruments (Zhang X et al. (2009) Science 324: 1330; Halvorsen K. (2007) Ph.D. Thesis, Boston University, Massachusetts), but with 160× overall magnification instead of 400×. High-speed video microscopy is used to measure bead positions in 1D with a resolution of ~4 nm at ~2 kHz. The optical trap is calibrated using the blur-corrected power spectrum fit (Wong W. P. et al. (2006) Opt. Express 14: 12517-31), with additional calibration information provided by the dsDNA overstretching transition (Smith S. B. et al. (1996) Science 271: 795).

Single-molecule force measurements are performed by bringing linker functionalized beads held in the optical trap into contact with streptavidin-coated beads held in the micropipette to form molecular tethers. Tension in each tether is applied by moving the bead in the micropipette, and quantified by measuring the displacement of the bead in the optical trap. The observed distance between the beads gives a measure of the tether length.

Results and Discussion

Looped single-molecule linkers were created via DNA self-assembly. Two different kinds of linker constructs were generated and tested: (i) linkers looped by a short complementary strand of DNA to study the kinetics of DNA base pairing, and (ii) linkers looped by a receptor-ligand pair to study protein-protein interactions. As detailed below, the proper assembly and functionality of these linkers was verified using gel-shift assays and optical trap measurements. Their effectiveness for single-molecule force spectroscopy was demonstrated by measuring the kinetics of bond rupture for both DNA hybridization and an antibody-antigen interactions, and by showing how the molecular signature of a looped tether can be used to improve the accuracy of the data.

Verification of the linker assembly: The linkers looped by a single DNA oligonucleotide bridge were tested first, as they served as a good model system for testing and optimizing linker assembly, independent of protein-coupling efficiency. For these oligonucleotide bridge constructs, two different loop lengths were made: 2580 base pairs and 600 base pairs. Additionally, the length of the bridge oligonucleotide on one side was varied to be 30 bp, 20 bp, 15 bp, and 10 bp, while the other side was maintained at 30 bp. The formations of both long and short loops were easily distinguishable from those of unlooped products by a gel shift due to slower migration on a 0.7% agarose gel (FIG. 3A), for both the 30 bp and 20 bp bridge constructs. Looped constructs in the gel were not observed when using the 15 bp or 10 bp bridge oligo, presumably due to the harsh conditions of electrophoresis (e.g. low salt, high temperature, high voltage). Confirmation that the shifted gel band was indeed the looped construct was accomplished by cutting the construct with a single-cut enzyme in the loop region (FIG. 3A). The shifted band (looped DNA) was largely unaffected by the enzyme, while the lower band (unlooped DNA) was completely digested into two separate pieces.

Next, these products (with double-biotin ends) were verified directly in the optical trap by pulling them end to end with linear ramps of force (FIG. 3A). Unlooped linkers show characteristic DNA force-extension behavior with typical contour lengths of 2000-2300 nm, consistent with the number of DNA bases within the construct. The looped linkers initially start with a shorter contour length, then exhibit a sudden increase to this full contour length when the DNA bridge ruptures under the application of mechanical stress. An average increase in contour length of 884 nm and 208 nm was measured for the long and short loops, respectively (FIG. 3A, inset), which is within a few nanometers of the expected length changes of 877 and 204 nm predicted from the worm-like chain polymer model using a contour length of 0.34 nm per base pair (Bustamante C. et al. (1994) Science 265: 1599-600; Bustamante C. et al. (2003) Nature 421 423-7). As can be seen in FIG. 3A, after bridge rupture both curves roughly follow the curve for the unlooped linker. As the linker was stressed above 65 pN, the DNA overstretching transition could be observed, which served as an additional mechanical signature for identifying single-molecule tethers. Pulling the molecule through this transition always resulted in detachment of the linker from the functionalized beads, presumably due to the force-induced melting of the biotinylated anchor oligonucleotides off of the ssDNA scaffold. While this effectively limits the use of this linker to measurements below about 65 pN, this could likely be overcome by covalently cross-linking the DNA linker or by using much longer anchoring oligonucleotides. Regarding the observed length of the linkers, a distribution of lengths is expected from multiple-tether measurements, even if every tether is identical on a molecular level. Because the bead in the pipette is rotationally constrained, tethers may be held at different angles, causing the measured distance between the beads to differ from the molecular tether length.

Receptor-ligand looped linkers were also created in order to measure the force-dependent kinetics of an antibody-antigen interaction. Oligonucleotides coupled to digoxigenin and to its antibody were assembled to form linkers with a loop length of 600 base pairs. The verification of these constructs was conducted in the same way as for the DNA bridge looped linkers, using both gel electrophoresis shift assays and single-molecule pulling experiments. The polyclonal looped construct was readily observed in a gel as a distinct shifted band (identical to the DNA bridge looped construct in FIG. 3A). In some instances, the monoclonal construct was not observed, likely due to the much lower affinity between digoxigenin and its monoclonal antibody and is consistent with the lack of a band for the 10 bp and 15 bp DNA bridge constructs. Both the monoclonal and polyclonal constructs were observed in the optical trap and exhibited force-extension curves that matched those of the 600 bp oligonucleotide bridge construct.

Demonstration of single-molecule force spectroscopy: The dynamic strength of DNA hybridization was tested with the optical trap by repeatedly applying linear force ramps to the DNA bridge constructs to determine the distribution of the rupture force. The molecular signature of the looped linker served as a powerful filtering method to distinguish the rupture of the DNA bridge from non-specific, unknown and multiple interactions. This is illustrated in FIG. 4 (left) for the rupture force of the 20 bp bridge, where positive identification of the correct rupture transition (using the change in tether length, overall tether length, and overstretching of the linker) enabled the removal of erroneous data that accounted for 57% (34/60) of the measured events. In the resulting data, a mean rupture force of 52 pN was measured with a standard deviation of 6 pN at a nominal loading rate of 100 pN nm$^{-1}$ (this was a combination of experiments with a mean loading rate of 98 pN nm$^{-1}$ and a standard deviation of 35 pN nm$^{-1}$). This agrees within error with the expected force of 39±15 pN for the mechanical shearing of DNA (based upon their empirical formula) (Strunz T. (1999) Proc. Natl Acad. Sci. 96: 11277).

When testing the other DNA bridge lengths, fewer rupture events were observed for the 30 bp bridge, as the biotin-streptavidin bonds anchoring the linker often ruptured first. In addition, there was evidence of the 15 bp and 10 bp bridges in single-molecule pulling experiments, despite not observing these constructs with the gel-shift assay. While the formation of these loops should be energetically favorable even with the additional entropic cost of closing the loop (Hanke A. et al. (2003) Biophys. J. 85: 167-73), it is possible that the conditions of electrophoresis lower the stability of these constructs leading to their absence in the gel assays.

As another demonstration, the force-dependent unbinding kinetics of digoxigenin with its antibody was measured in the optical trap (FIG. 4 (right)). By recording repeated measurements of bond rupture under a constant force, a characteristic lifetime of 1.3 s (with a 95% confidence band of 0.9-2.0 s) at a force of 49±2 pN for the polyclonal antibody was found, using maximum likelihood estimation with an exponential decay model. This interaction was relatively strong, in agreement with other single-molecule measurements that used it as a molecular anchor (Khalil A. S. et al. (2007) Proc. Natl Acad. Sci. 104: 4892). Without the looped linker, the high bond strength of this interaction can make rupture measurements difficult, as it can be difficult to distinguish the rupture of digoxigenin-antibody from the failure of molecular anchors in the absence of an additional molecular signature.

Figure 5:
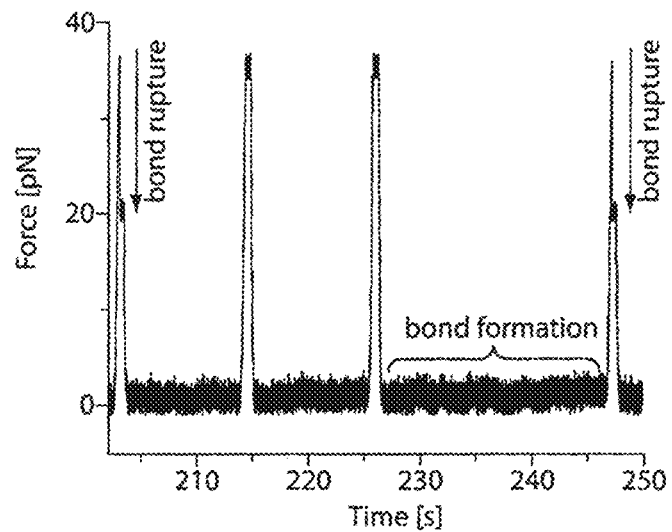
FIG. 5. Trajectory demonstrating repeated rupture and formation of a single receptor-ligand pair (digoxigenin with its monoclonal antibody): (left) force versus time and (right) force versus extension traces for repeated cycles of force application and release. Bond rupture events are observable by a sudden drop in force and an increase in tether length, as demarcated by red arrows. Rebinding/bond formation during a low force clamp can be observed by subsequent bond rupture under the application of force.
Figure 5:
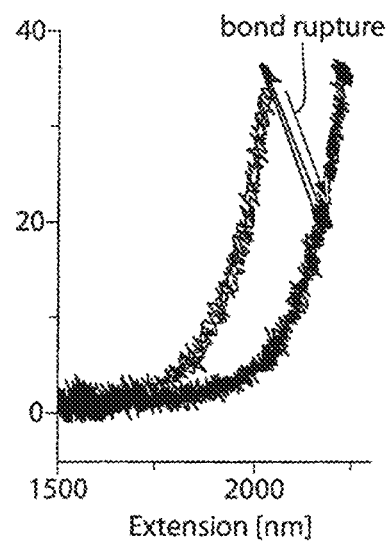

Bond rupture was measured, and single-molecule bond formation was observed. In many cases with the digoxigenin-antibody construct, the complex was reformed after dissociation by bringing the beads closer together and waiting for a short time (FIG. 5). Reformation of the oligonucleotide bridge after rupture under similar conditions was not possible, suggesting that the formation of secondary structure or the extra time to diffusively align the two strands slowed the rebinding kinetics. This may be overcome by increasing the concentration of the bridge oligonucleotide in the vicinity of the nucleic acid complex.

Conclusion

Presented herein is a simple and effective method for producing functional looped linkers using DNA self-assembly, which can increase the accuracy and reliability of single-molecule force measurements. The method is versatile enough to be useful for a wide range of molecular interactions, and simple enough to be made by researchers of diverse backgrounds without significant investment of time or money (see the appendix). This functionality was demonstrated by constructing and testing two different looped linkers, designed for studying the dynamic strength of DNA base pairing and receptor-ligand interactions. In addition, the molecular signature provided by this 'DNA mechanical switch' enables the removal of erroneous data that can arise from non-specific, unknown, and multiple interactions. Not only is this construct useful for traditional bond rupture measurements and force spectroscopy, but it also enables the same pair of interacting molecules to be brought back together following rupture, opening the way toward high-throughput serial measurements, single-molecule on-rate studies, and studies of population heterogeneity.

Example 2

Receptor-Ligand Dissociation Kinetics Elucidated by Electrophoresis of a Binary DNA Nanoswitch Materials and Methods Linkers were designed according to protocols for long (2580 bp) and short (600 bp) loops as described herein. (See also Halvorsen K. et al. (2011) Nanotechnology, 22: 494005 incorporated herein by reference.) Here, modified oligos (Bioneer, Inc.) containing a single biotin were used such that a single streptavidin molecule could close the loop. All other oligos were the same as those used previously. Briefly, looped constructs were made by mixing a long single-stranded DNA (M13mp18, in this case) with over 121 oligos that are complementary along its length. Two oligos spaced apart from each other had biotin modifications, causing a loop to form when streptavidin binds both. The constructs come together by self-assembly with a temperature ramp heating and cooling them.

Results

Recognizing that the nanoswitch conformation informs the receptor-ligand binding state (bound or unbound), and that the conformation can be observed on a gel, an assay to measure bulk interaction kinetics was developed. The assay, conceptually shown in FIG. 7, proceeds as follows: 1) form a looped nucleic acid (DNA) construct that relies on a receptor and a ligand being bound to each other, 2) quench the interaction between the receptor and the ligand, for example, with excess receptor or ligand to prevent rebinding following dissociation, 3) monitor the relative amount of looped construct over time to measure kinetics.

To demonstrate the utility of the technique, nanoswitches were developed to measure the unbinding kinetics of the biotin-streptavidin interaction. Linear double-stranded DNA constructs 7249 base pairs (bp) in length were self-assembled by combining the single-stranded M13 bacteriophage genome with 121 complementary oligos. (See also Halvorsen K et al., 2011). Two of the oligos were labeled with single biotins and placed 2580 bp from each other, such that interaction with streptavidin induced the formation of a 2580 bp loop in the structure. Working backwards from a predetermined experiment time, the nanoswitches were immersed in excess biotin and various experimental conditions at various times (in this case: 125, 25, 5, 1, and 0.2 hours). The entire array of 16 conditions with five time points each plus controls was then run on a single 96 lane agarose gel (FIG. 8).

To determine the biotin-streptavidin dissociation kinetics, an image of the gel was analyzed using publicly available software (ImageJ). The gel analysis tool in ImageJ was used to measure the integrated intensity of the band containing looped construct, and this quantity was normalized by the integrated intensity of a reference band in the same lane from a DNA ladder, which was added to the construct prior to starting experiments. Individual time constants for each experimental condition were determined by fitting a single exponential decay to the data using an error weighted least squares fitting.

Under the conditions tested, biotin-streptavidin time constants ranged from about half of an hour to two months (FIG. 8, upper right table). The time constants are multiplied by two to represent a single biotin-streptavidin interaction—the time constants for two bonds in series were directly measured. The interaction was highly sensitive to changing temperature and less sensitive to changing salt. At a given salt concentration, the off-rate varied over 100 fold, from 4° C. to 50° C., whereas at a given temperature, the off-rate changed by less than 2 fold from, 5 mM to 500 mM. At physiological salt concentration (150 mM), dissociation times of 148±10 hours at 25° C. and 11.2±3 hours at 37° C. were measured. The values obtained are within range of previously reported values at 25° C. and 37° C. (Chivers C. E. et al. (2010) Nature Methods 7(5): 391-393; Klumb L. A. et al. (1998) Biochemistry (Washington) 37(21): 7657-7663; Chilkoti A. et al. (1995) Journal of the American Chemical Society 117(43): 10622-10628; Jung L. S. et al. (2000) Langmuir 16(24): 9421-9432; Green N. M. (1990) Methods in Enzymology 184: 51-67).

To demonstrate the versatility of the technique, a small suite of nanoswitches was developed to measure different interactions. Antibody-antigen interaction, protein G-antibody interaction, DNA hybridization interaction, and enzymatic cleavage were demonstrated. The antibody-antigen interaction measured was digoxigenin (dig) and its polyclonal antibody. Using a dig-labeled oligonucleotide (oligo) and an anti-dig-labeled oligo, a dissociation time constant of 18.5 hours was measured. For the protein G-antibody interaction, the anti-dig labeled oligo along with a protein G-labeled oligo was used. DNA hybridization kinetics and enzymatic cleavage were both performed using a single oligo to act as the loop closure. For DNA unhybridization kinetics, an oligo with a 30 bp overlap on one side and a 20 bp overlap on the loop closure was used to measure a 20 bp hybridization off-rate. Enzymatic cleavage rates were measured using an oligo similar to that used for DNA hybridization, but with a central 20 bp insertion (and its complement) that includes the specific cleavage site for XhoI.

With these examples, it has been demonstrated that dissociation times range from minutes to weeks, across a variety of molecular systems. Measurements of more slowly dissociating molecules is possible, and is mainly limited by the patience of the experimenter and the ability to keep the molecules from degrading. Measurements of more quickly dissociating molecules is also possible, but the effect of the electrophoresis time needs to be more carefully considered. The method, as outlined, may be used for interactions with dissociation times at the gel running conditions that are comparatively slower than the gel running time. The reason for this is that the looped constructs are free to become unlooped during electrophoresis, which for these experiments, spanned 90 minutes. This effect will cause an overall reduction in the signal of the looped bands, but all gel lanes will be reduced in the same way. Thus, as long as the bands are still resolvable, there should be no major impact on the off-rate measurements. This sets a limitation on the shortest dissociation time that can be measured relative to the electrophoresis time, which would be approximately 1 hour (off-rate of $10^{-4}$).

There are a few simple ways to circumvent this limitation, one of which has been demonstrated by measuring significantly faster off-rates. For the enzymatic cleavage assay, it was possible to measure an off-rate significantly faster than $10^{-4}$ by "quenching" the cleavage with ethylenediaminetetraacetic acid (EDTA). Once the cleavage site was quenched, dissociation in the gel was not an issue. Similarly, it was possible to measure biotin-streptavidin off-rates as fast as 40 minutes at high temperature because the removal of temperature acts to effectively quench the reaction. For reactions that cannot be quenched in this way, dissociation could be chemically quenched by using a crosslinker to hold the loops closed in the gel. For example, the photoactivated DNA crosslinker trimethylpsoralen can be used to hold DNA loops together, even in cases where they normally dissociate during the gel. This strategy may be adopted to increase the range of kinetic measurements.

Conclusion

The method provided herein has at least two useful advantages: high accessibility and multiplexed measurement capability. The method is neither expensive nor difficult. It requires only minimal infrastructure and equipment (e.g., electrophoresis tools), most of which is already available in almost any biology or chemistry lab. While there is an upfront cost of making the nanoswitches (mostly from the cost of oligos), this cost is quite low on a per experiment basis. Overall, these experiments demonstrate the ability to measure molecular kinetics using a nanoengineered molecular switch along with a gel readout of the switch's state. The method provides an accurate, inexpensive, and multiplexed way to measure kinetics for a wide variety of interactions. The minimal infrastructure and equipment requirements offer a distinct advantage over established methods such as surface plasmon resonance or radioligand assays. This method will provide increased accessibility to the measurement of molecular kinetics.

Example 3

Encryption and Decryption Using Nucleic Acid Complexes

Materials and Methods

Oligonucleotides were designed and purchased (Bioneer, Inc.) to represent 8 different bits, which would be about evenly spaced on a 4% agarose gel. The lengths chosen were 20 nt, 22 nt, 25 nt, 28 nt, 32 nt, 37 nt, 43 nt, and 50 nt. For each length, 3 oligonucleotides were purchased: a randomly generated sequence, its complementary strand, and a random set with arbitrary bases. These are denoted A, A', and B respectively.

To encode messages, the plain text message "Hello world" was first converted into binary code using 8 bit ASCII character encoding with the 8th bit as an even parity bit for error checking. Each letter was prepared using a mixture of A and B oligonucleotides to represent the 0s and 1s. As an example, the "H" in "Hello world" has an 8 bit binary representation of 01001000. The least significant bit is encoded in the smallest (20 nt) oligo, which is denoted oligo 1. To encode the "H", oligonucleotides 4 and 7 from set A are mixed with oligonucleotides 1, 2, 3, 5, 6, and 8 from set B.

For decoding, the encoded message mixtures were individually mixed with the entire set A' of oligonucleotides in a buffer solution (1× Buffer 4, New England Biolabs) and loaded into a gel (within minutes). An automated precast 4% agarose gel (E-gel, Invitrogen) containing a proprietary dye (with characteristics remarkably similar to Sybr gold) was run for 15 minutes and photographs taken immediately thereafter. The binary representation of each gel lane could be read directly from top to bottom.

Results

Figure 11:
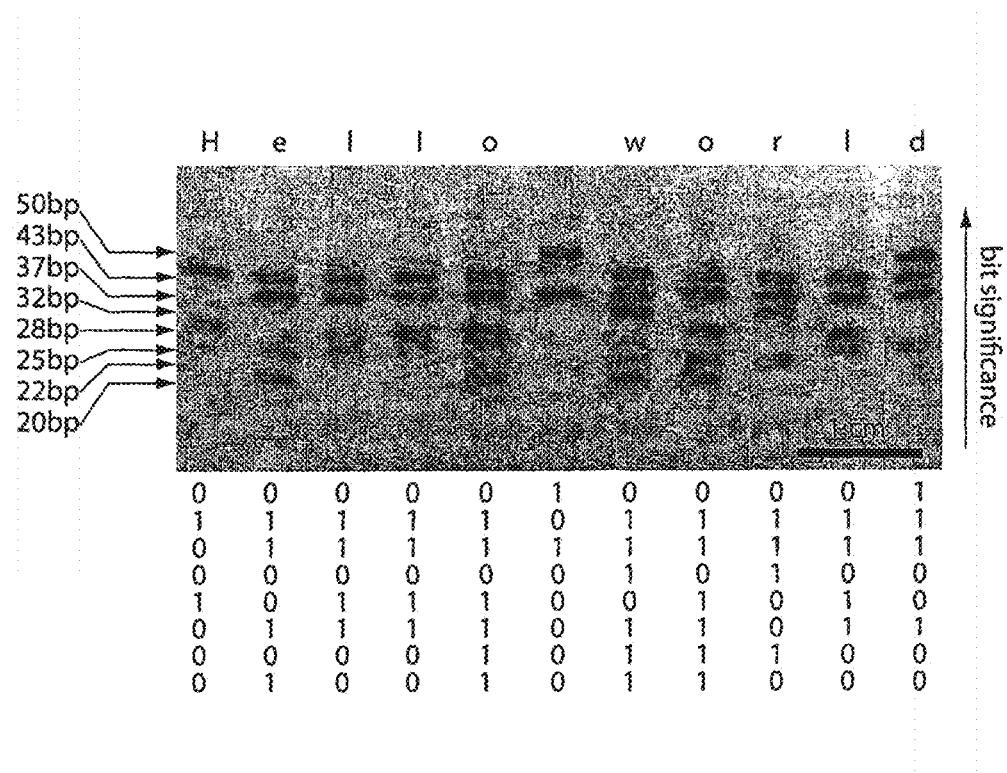
FIG. 11. Decoding a binary message on a gel. Each lane of the gel contains a mixture of oligonucleotides, which together form an 11 byte binary ASCII message which reads "Hello world". The bit strings are read from top to bottom with the most significant bit being the largest DNA segment. Presence of a band indicates a binary 1, while absence of a band indicates a binary 0. All lanes have the same amount of DNA present, but only the double-stranded fragments bind the dye and are visible.

An 8-bit encoding system was used to experimentally demonstrate the encryption aspect of the invention. Eight different lengths of DNA strands were used to represent individual bits. A plaintext message was encoded using 8-bit binary ASCII encoding with the 8th bit as an even parity bit. The message was encrypted into multiple DNA mixtures, one for each letter. These mixtures were then decrypted by mixing them with private key oligonucleotides and decoded by running an agarose gel. Reading/decoding each gel lane from top to bottom, the decrypted message "Hello world" became clear (FIG. 11).

While this Example demonstrates 1 byte (8 bits) of data storage per mixture (and per gel lane), the amount of data stored and read out is not so limited and can be readily increased. If DNA lengths were optimized to be evenly spaced on the gel, a resolution of 1 mm would result in 10 bits/cm of gel length, corresponding to roughly 8 bytes of data for a single short gel lane, 10-20 bytes for longer gels, and up to 125 bytes (1000 bits) for more elaborate sequencing gels with base pair resolution (França, L. et al. (2002) Quarterly Reviews of Biophysics 35: 169-200). Expanding to a few bytes may enable the transmission of entire words or short messages in a single mixture, especially when a more efficient character encoding scheme is used (e.g., the 5 bit Baudot code), or a word-based encoding scheme (e.g., 10 bytes can encode eight words of a 1000 word vocabulary). In addition, data density can be increased by combining multiple messages within a single mixture, with each message associated with a different decryption key.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

REFERENCES

Kim J, Zhang C Z, Zhang X and Springer T A 2010 A mechanically stabilized receptor-ligand flex-bond important in the vasculature. Nature 466 992-5.

Wiita A P, Ainavarapu S R K, Huang H H and Fernandez J M 2006 Force-dependent chemical kinetics of disulfide bond reduction observed with single-molecule techniques Proc. Natl Acad. Sci. 103 7222-7.

What is claimed is:

1. A nucleic acid complex comprising
a single-stranded scaffold nucleic acid hybridized to a plurality of single-stranded oligonucleotides thereby forming a linear partially double-stranded nucleic acid, wherein a first single-stranded oligonucleotide in the plurality is linked to a first binding partner and a second single-stranded oligonucleotide in the plurality is linked to a second binding partner,
wherein the first and second binding partners have
(i) binding affinity for an analyte that is neither the first nor the second binding partner or
(ii) binding affinity for each other, and
a loop is created in the scaffold nucleic acid when the first and second binding partners either (i) bind to the analyte in the presence of the analyte or (ii) bind to each other.

2. The nucleic acid complex of claim 1, wherein the first and second binding partners have binding affinity for an analyte that is neither the first nor the second binding partner.

3. The nucleic acid complex of claim 1, wherein the first and second binding partners have binding affinity for each other.

4. The nucleic acid complex of claim 1, wherein the first binding partner is a receptor and the second binding partner is a ligand for the receptor.

5. The nucleic acid complex of claim 1, wherein the first binding partner is an antibody or an antigen-binding antibody fragment and the second binding partner is an antigen bound by the antibody or the antigen-binding fragment.

6. The nucleic acid complex of claim 1, wherein the first single-stranded oligonucleotide and the second single-stranded oligonucleotide are separated from each other by at least 10 nucleotides.

7. The nucleic acid complex of claim 1, wherein the first single-stranded oligonucleotide and the second single-stranded oligonucleotide are located about equidistant from the center of the scaffold nucleic acid.

8. The nucleic acid complex of claim 1, wherein the first binding partner is an antibody or an antigen-binding antibody fragment.

9. The nucleic acid complex of claim 1, wherein the first and second binding partners are antibodies or antigen-binding antibody fragments.

10. The nucleic acid complex of claim 9, wherein the first and second binding partners are identical to each other.

11. The nucleic acid complex of claim 1, wherein the first and second binding partners have binding affinity for the same analyte, and each is an antibody or an antigen-binding antibody fragment.

12. The nucleic acid complex of claim 1, wherein the first and second binding partners bind to each other or to the analyte non-covalently.

13. The nucleic acid complex of claim 1, wherein the first single-stranded oligonucleotide and the second single-stranded oligonucleotide are separated from each other by at least 200 nucleotides.

14. The nucleic acid complex of claim 1, wherein the first single-stranded oligonucleotide and the second single-stranded oligonucleotide are separated from each other by at least 1000 nucleotides.

15. A nucleic acid complex comprising
a single-stranded scaffold nucleic acid and a plurality of single-stranded oligonucleotides, each of which hybridizes throughout its length to a contiguous nucleotide sequence in the scaffold nucleic acid, wherein a first single-stranded oligonucleotide in the plurality is linked to a first binding partner, and a second single-stranded oligonucleotide in the plurality is linked to a second binding partner,
wherein the first and second binding partners have
(i) binding affinity for an analyte that is neither the first nor the second binding partner or
(ii) binding affinity for each other, and
a loop is created in the scaffold nucleic acid when the first and second binding partners either (i) bind to the analyte in the presence of the analyte or (ii) bind to each other.

16. The nucleic acid complex of claim 15, wherein each oligonucleotide is complementary to a contiguous sequence in the scaffold nucleic acid.

17. The nucleic acid complex of claim 15, wherein the first and second binding partners have binding affinity for an analyte that is neither the first nor the second binding partner.

18. The nucleic acid complex of claim 15, wherein the first and second binding partners have binding affinity for each other.

19. The nucleic acid complex of claim 15, wherein the first single-stranded oligonucleotide and the second single-stranded oligonucleotide are separated from each other by at least 10 nucleotides.

20. The nucleic acid complex of claim 15, wherein the first binding partner is an antibody or an antigen-binding antibody fragment.

21. The nucleic acid complex of claim 15, wherein the first and second binding partners are antibodies or antigen-binding antibody fragments.

22. The nucleic acid complex of claim 21, wherein the first and second binding partners are identical to each other.

23. The nucleic acid complex of claim 15, wherein the first and second binding partners have binding affinity for the same analyte, and each is an antibody or an antigen-binding antibody fragment.

24. The nucleic acid complex of claim 15, wherein the first single-stranded oligonucleotide and the second single-stranded oligonucleotide are separated from each other by at least 1000 nucleotides.

25. A nucleic acid complex comprising
a single-stranded scaffold nucleic acid hybridized to a plurality of single-stranded oligonucleotides thereby forming a linear partially double-stranded nucleic acid, wherein a first single-stranded oligonucleotide in the plurality is linked to a first binding partner, a second single-stranded oligonucleotide in the plurality is linked to a second binding partner, and
wherein the first and second binding partners have
(i) binding affinity for a common analyte that is not a nucleic acid or
(ii) binding affinity for each other, and
a loop is created in the scaffold nucleic acid when the first and second binding partners either (i) bind to the analyte in the presence of the analyte or (ii) bind to each other.

26. The nucleic acid complex of claim 25, wherein the first and second binding partners bind to each other or to the analyte non-covalently.

27. The nucleic acid complex of claim 25, wherein the first and second binding partners have binding affinity for a common analyte.

28. The nucleic acid complex of claim 25, wherein the first and second binding partners have binding affinity for each other.

29. The nucleic acid complex of claim 25, wherein the first single-stranded oligonucleotide and the second single-stranded oligonucleotide are separated from each other by at least 10 nucleotides.

30. The nucleic acid complex of claim 25, wherein the first binding partner is an antibody or an antigen-binding antibody fragment.

31. The nucleic acid complex of claim 25, wherein the first and second binding partners are antibodies or antigen-binding antibody fragments.

32. The nucleic acid complex of claim 31, wherein the first and second binding partners are identical to each other.

33. The nucleic acid complex of claim 25, wherein the first and second binding partners have binding affinity for a common analyte, and each is an antibody or an antigen-binding antibody fragment.

34. The nucleic acid complex of claim 25, wherein the first single-stranded oligonucleotide and the second single-stranded oligonucleotide are separated from each other by at least 1000 nucleotides.

* * * * *

SEQUENCE LISTING

<160> NUMBER OF SEQ ID NOS: 134

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 1
aacatccaat aaatcataca ggcaaggcaa agaattagca aaattaagca ataaagcctc    60

<210> SEQ ID NO 2
<211> LENGTH: 60

```
<212> TYPE: DNA
<213> ORGANISM: Artificial Sequence
<220> FEATURE:
<223> OTHER INFORMATION: Synthetic Oligonucleotide

<400> SEQUENCE: 2
agagcataaa gctaaatcgg ttgtaccaaa aacattatga ccctgtaata cttttgcggg      60

<210> SEQ ID NO 3
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 3
agaagccttt atttcaacgc aaggataaaa attttagaa ccctcatata ttttaaatgc       60

<210> SEQ ID NO 4
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 4
aatgcctgag taatgtgtag gtaaagattc aaagggtga gaaaggccgg agacagtcaa       60

<210> SEQ ID NO 5
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 5
atcaccatca atatgatatt caaccgttct agctgataaa ttaatgccgg agagggtagc     60

<210> SEQ ID NO 6
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 6
tatttttgag agatctacaa aggctatcag gtcattgcct gagagtctgg agcaaacaag     60

<210> SEQ ID NO 7
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 7
agaatcgatg aacggtaatc gtaaaactag catgtcaatc atatgtaccc cggttgataa     60

<210> SEQ ID NO 8
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 8
```
tcagaaaagc cccaaaaaca ggaagattgt ataagcaaat atttaaattg taaacgttaa    60

<210> SEQ ID NO 9
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 9
tattttgtta aaattcgcat taaattttg ttaaatcagc tcatttttta accaatagga    60

<210> SEQ ID NO 10
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 10
acgccatcaa aaataattcg cgtctggcct tcctgtagcc agctttcatc aacattaaat    60

<210> SEQ ID NO 11
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 11
gtgagcgagt aacaacccgt cggattctcc gtgggaacaa acggcggatt gaccgtaatg    60

<210> SEQ ID NO 12
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 12
ggataggtca cgttggtgta gatgggcgca tcgtaaccgt gcatctgcca gtttgagggg    60

<210> SEQ ID NO 13
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 13
acgacgacag tatcggcctc aggaagatcg cactccagcc agctttccgg caccgcttct    60

<210> SEQ ID NO 14
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 14
ggtgccggaa accaggcaaa gcgccattcg ccattcaggc tgcgcaactg ttgggaaggg    60

<210> SEQ ID NO 15
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 15
cgatcggtgc gggcctcttc gctattacgc cagctggcga aaggggatg tgctgcaagg    60

<210> SEQ ID NO 16
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 16
cgattaagtt gggtaacgcc agggttttcc cagtcacgac gttgtaaaac gacggccagt    60

<210> SEQ ID NO 17
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 17
gccaagcttg catgcctgca ggtcgactct agaggatccc cgggtaccga gctcgaattc    60

<210> SEQ ID NO 18
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 18
gtaatcatgg tcatagctgt ttcctgtgtg aaattgttat ccgctcacaa ttccacacaa    60

<210> SEQ ID NO 19
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 19
catacgagcc ggaagcataa agtgtaaagc ctggggtgcc taatgagtga gctaactcac    60

<210> SEQ ID NO 20
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 20
attaattgcg ttgcgctcac tgcccgcttt ccagtcggga aacctgtcgt gccagctgca    60

<210> SEQ ID NO 21
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 21
ttaatgaatc ggccaacgcg cggggagagg cggtttgcgt attgggcgcc agggtggttt    60

<210> SEQ ID NO 22
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 22
ttcttttcac cagtgagacg ggcaacagct gattgccctt caccgcctgg ccctgagaga    60

<210> SEQ ID NO 23
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 23
gttgcagcaa gcggtccacg ctggtttgcc ccagcaggcg aaaatcctgt ttgatggtgg    60

<210> SEQ ID NO 24
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 24
ttccgaaatc ggcaaaatcc cttataaatc aaaagaatag cccgagatag ggttgagtgt    60

<210> SEQ ID NO 25
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 25
tgttccagtt tggaacaaga gtccactatt aaagaacgtg gactccaacg tcaaagggcg    60

<210> SEQ ID NO 26
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 26
aaaaaccgtc tatcagggcg atggcccact acgtgaacca tcacccaaat caagttttt    60

<210> SEQ ID NO 27
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 27
ggggtcgagg tgccgtaaag cactaaatcg gaaccctaaa gggagccccc gatttagagc    60

<210> SEQ ID NO 28
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 28
ttgacgggga aagccggcga acgtggcgag aaaggaaggg aagaaagcga aaggagcggg    60

<210> SEQ ID NO 29
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 29
cgctagggcg ctggcaagtg tagcggtcac gctgcgcgta accaccacac ccgccgcgct    60

<210> SEQ ID NO 30
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 30
taatgcgccg ctacagggcg cgtactatgg ttgctttgac gagcacgtat aacgtgcttt    60

<210> SEQ ID NO 31
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 31
cctcgttaga atcagagcgg gagctaaaca ggaggccgat taaagggatt ttagacagga    60

<210> SEQ ID NO 32
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 32
acggtacgcc agaatcctga gaagtgtttt tataatcagt gaggccaccg agtaaaagag    60

<210> SEQ ID NO 33
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 33
tctgtccatc acgcaaatta accgttgtag caatacttct ttgattagta ataacatcac    60

<210> SEQ ID NO 34
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 34
ttgcctgagt agaagaactc aaactatcgg ccttgctggt aatatccaga acaatattac    60

<210> SEQ ID NO 35

<210> SEQ ID NO 35
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 35
cgccagccat tgcaacagga aaaacgctca tggaaatacc tacatttga cgctcaatcg      60

<210> SEQ ID NO 36
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 36
tctgaaatgg attatttaca ttggcagatt caccagtcac acgaccagta ataaaaggga      60

<210> SEQ ID NO 37
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 37
cattctggcc aacagagata gaaccttct gacctgaaag cgtaagaata cgtggcacag      60

<210> SEQ ID NO 38
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 38
acaatatttt tgaatggcta ttagtcttta atgcgcgaac tgatagccct aaaacatcgc      60

<210> SEQ ID NO 39
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 39
cattaaaaat accgaacgaa ccaccagcag aagataaaac agaggtgagg cggtcagtat      60

<210> SEQ ID NO 40
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 40
taacaccgcc tgcaacagtg ccacgctgag agccagcagc aaatgaaaaa tctaaagcat      60

<210> SEQ ID NO 41
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 41

```
caccttgctg aacctcaaat atcaaaccct caatcaatat ctggtcagtt ggcaaatcaa    60
```

<210> SEQ ID NO 42
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 42

```
cagttgaaag gaattgagga aggttatcta aaatatcttt aggagcacta acaactaata    60
```

<210> SEQ ID NO 43
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 43

```
gattagagcc gtcaatagat aatacatttg aggatttaga agtattagac tttacaaaca    60
```

<210> SEQ ID NO 44
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 44

```
attcgacaac tcgtattaaa tcctttgccc gaacgttatt aatttttaaaa gtttgagtaa    60
```

<210> SEQ ID NO 45
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 45

```
cattatcatt ttgcggaaca aagaaaccac cagaaggagc ggaattatca tcatattcct    60
```

<210> SEQ ID NO 46
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 46

```
gattatcaga tgatggcaat tcatcaatat aatcctgatt gtttggatta tacttctgaa    60
```

<210> SEQ ID NO 47
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 47

```
taatggaagg gttagaacct accatatcaa aattatttgc acgtaaaaca gaaataaaga    60
```

<210> SEQ ID NO 48
<211> LENGTH: 60
<212> TYPE: DNA

<213> ORGANISM: Artificial Sequence
<220> FEATURE:
<223> OTHER INFORMATION: Synthetic Oligonucleotide

<400> SEQUENCE: 48
aattgcgtag attttcaggt ttaacgtcag atgaatatac agtaacagta cctttttacat    60

<210> SEQ ID NO 49
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 49
cgggagaaac aataacggat tcgcctgatt gctttgaata ccaagttaca aaatcgcgca    60

<210> SEQ ID NO 50
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 50
gaggcgaatt attcatttca attacctgag caaagaaga tgatgaaaca aacatcaaga    60

<210> SEQ ID NO 51
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 51
aaacaaaatt aattacattt aacaatttca tttgaattac cttttttaat ggaaacagta    60

<210> SEQ ID NO 52
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 52
cataaatcaa tatatgtgag tgaataacct tgcttctgta aatcgtcgct attaattaat    60

<210> SEQ ID NO 53
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 53
tttcccttag aatccttgaa aacatagcga tagcttagat taagacgctg agaagagtca    60

<210> SEQ ID NO 54
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 54
atagtgaatt tatcaaaatc ataggtctga gagactacct ttttaacctc cggcttaggt    60

<210> SEQ ID NO 55
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 55
tgggttatat aactatatgt aaatgctgat gcaaatccaa tcgcaagaca aagaacgcga    60

<210> SEQ ID NO 56
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 56
gaaaactttt tcaaatatat tttagttaat ttcatcttct gacctaaatt taatggtttg    60

<210> SEQ ID NO 57
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 57
aaataccgac cgtgtgataa ataaggcgtt aaataagaat aaacaccgga atcataatta    60

<210> SEQ ID NO 58
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 58
ctagaaaaag cctgtttagt atcatatgcg ttatacaaat tcttaccagt ataaagccaa    60

<210> SEQ ID NO 59
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 59
cgctcaacag tagggcttaa ttgagaatcg ccatatttaa caacgccaac atgtaattta    60

<210> SEQ ID NO 60
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 60
ggcagaggca ttttcgagcc agtaataaga gaatataaag taccgacaaa aggtaaagta    60

<210> SEQ ID NO 61
<211> LENGTH: 60
<212> TYPE: DNA
<213> ORGANISM: Artificial Sequence
<220> FEATURE:

-continued

<223> OTHER INFORMATION: Synthetic Oligonucleotide

<400> SEQUENCE: 61
attctgtcca gacgacgaca ataaacaaca tgttcagcta atgcagaacg cgcctgttta    60

<210> SEQ ID NO 62
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 62
tcaacaatag ataagtcctg aacaagaaaa ataatatccc atcctaattt acgagcatgt    60

<210> SEQ ID NO 63
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 63
agaaaccaat caataatcgg ctgtctttcc ttatcattcc aagaacgggt attaaaccaa    60

<210> SEQ ID NO 64
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 64
gtaccgcact catcgagaac aagcaagccg tttttatttt catcgtagga atcattaccg    60

<210> SEQ ID NO 65
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 65
cgcccaatag caagcaaatc agatatagaa ggcttatccg gtattctaag aacgcgaggc    60

<210> SEQ ID NO 66
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 66
gttttagcga acctcccgac ttgcgggagg ttttgaagcc taaatcaag attagttgct    60

<210> SEQ ID NO 67
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 67
attttgcacc cagctacaat tttatcctga atcttaccaa cgctaacgag cgtctttcca    60

```
<210> SEQ ID NO 68
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 68
gagcctaatt tgccagttac aaaataaaca gccatattat ttatcccaat ccaaataaga    60

<210> SEQ ID NO 69
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 69
aacgattttt tgtttaacgt caaaaatgaa aatagcagcc tttacagaga gaataacata    60

<210> SEQ ID NO 70
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 70
aaaacaggga agcgcattag acgggagaat taactgaaca ccctgaacaa agtcagaggg    60

<210> SEQ ID NO 71
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 71
taattgagcg ctaatatcag agagataacc cacaagaatt gagttaagcc caataataag    60

<210> SEQ ID NO 72
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 72
agcaagaaac aatgaaatag caatagctat cttaccgaag ccctttttaa gaaaagtaag    60

<210> SEQ ID NO 73
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 73
cagatagccg aacaaagtta ccagaaggaa accgaggaaa cgcaataata acggaatacc    60

<210> SEQ ID NO 74
<211> LENGTH: 60
<212> TYPE: DNA
<213> ORGANISM: Artificial Sequence
<220> FEATURE:
<223> OTHER INFORMATION: Synthetic Oligonucleotide
```

<400> SEQUENCE: 74
caaaagaact ggcatgatta agactcctta ttacgcagta tgttagcaaa cgtagaaaat    60

<210> SEQ ID NO 75
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 75
acatacataa aggtggcaac atataaaaga aacgcaaaga caccacggaa taagtttatt    60

<210> SEQ ID NO 76
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 76
ttgtcacaat caatagaaaa ttcatatggt ttaccagcgc caaagacaaa agggcgacat    60

<210> SEQ ID NO 77
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 77
tcaaccgatt gagggaggga aggtaaatat tgacggaaat tattcattaa aggtgaatta    60

<210> SEQ ID NO 78
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 78
tcaccgtcac cgacttgagc catttgggaa ttagagccag caaaatcacc agtagcacca    60

<210> SEQ ID NO 79
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 79
ttaccattag caaggccgga aacgtcacca atgaaaccat cgatagcagc accgtaatca    60

<210> SEQ ID NO 80
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 80
gtagcgacag aatcaagttt gcctttagcg tcagactgta gcgcgttttc atcggcattt    60

<210> SEQ ID NO 81
<211> LENGTH: 60

<210> SEQ ID NO 81
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 81
tcggtcatag cccccttatt agcgtttgcc atcttttcat aatcaaaatc accggaacca    60

<210> SEQ ID NO 82
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 82
gagccaccac cggaaccgcc tccctcagag ccgccaccct cagaaccgcc accctcagag    60

<210> SEQ ID NO 83
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 83
ccaccaccct cagagccgcc accagaacca ccaccagagc cgccgccagc attgacagga    60

<210> SEQ ID NO 84
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 84
ggttgaggca ggtcagacga ttggccttga tattcacaaa caaataaatc ctcattaaag    60

<210> SEQ ID NO 85
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 85
ccagaatgga aagcgcagtc tctgaattta ccgttccagt aagcgtcata catggctttt    60

<210> SEQ ID NO 86
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 86
gatgatacag gagtgtactg gtaataagtt ttaacggggt cagtgccttg agtaacagtg    60

<210> SEQ ID NO 87
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 87
cccgtataaa cagttaatgc cccctgccta tttcggaacc tattattctg aaacatgaaa    60

<210> SEQ ID NO 88
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 88
gtattaagag gctgagactc ctcaagagaa ggattaggat tagcggggtt ttgctcagta    60

<210> SEQ ID NO 89
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 89
ccaggcggat aagtgccgtc gagagggttg atataagtat agcccggaat aggtgtatca    60

<210> SEQ ID NO 90
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 90
ccgtactcag gaggtttagt accgccaccc tcagaaccgc caccctcaga accgccaccc    60

<210> SEQ ID NO 91
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 91
tcagagccac caccctcatt ttcagggata gcaagcccaa taggaaccca tgtaccgtaa    60

<210> SEQ ID NO 92
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 92
cactgagttt cgtcaccagt acaaactaca acgcctgtag cattccacag acagccctca    60

<210> SEQ ID NO 93
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 93
tagttagcgt aacgatctaa agttttgtcg tctttccaga cgttagtaaa tgaattttct    60

<210> SEQ ID NO 94
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 94
gtatgggatt tgctaaaca actttcaaca gtttcagcgg agtgagaata gaaaggaaca    60

<210> SEQ ID NO 95
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 95
actaaaggaa ttgcgaataa taatttttc acgttgaaaa tctccaaaaa aaaggctcca    60

<210> SEQ ID NO 96
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 96
aaaggagcct taattgtat cggtttatca gcttgctttc gaggtgaatt tcttaaacag    60

<210> SEQ ID NO 97
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 97
cttgataccg atagttgcgc cgacaatgac aacaaccatc gcccacgcat aaccgatata    60

<210> SEQ ID NO 98
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 98
ttcggtcgct gaggcttgca gggagttaaa ggccgctttt gcgggatcgt caccctcagc    60

<210> SEQ ID NO 99
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 99
agcgaaagac agcatcggaa cgagggtagc aacggctaca gaggctttga ggactaaaga    60

<210> SEQ ID NO 100
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 100
ctttttcatg aggaagtttc cattaaacgg gtaaaatacg taatgccact acgaaggcac    60

<210> SEQ ID NO 101
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 101
caacctaaaa cgaaagaggc aaaagaatac actaaaacac tcatctttga cccccagcga    60

<210> SEQ ID NO 102
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 102
ttataccaag cgcgaaacaa agtacaacgg agatttgtat catcgcctga taaattgtgt    60

<210> SEQ ID NO 103
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 103
cgaaatccgc gacctgctcc atgttactta gccggaacga ggcgcagacg gtcaatcata    60

<210> SEQ ID NO 104
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 104
agggaaccga actgaccaac tttgaaagag gacagatgaa cggtgtacag accaggcgca    60

<210> SEQ ID NO 105
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 105
taggctggct gaccttcatc aagagtaatc ttgacaagaa ccggatattc attacccaaa    60

<210> SEQ ID NO 106
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 106
tcaacgtaac aaagctgctc attcagtgaa taaggcttgc cctgacgaga aacaccagaa    60

<210> SEQ ID NO 107
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 107
cgagtagtaa attgggcttg agatggttta atttcaactt taatcattgt gaattacctt        60

<210> SEQ ID NO 108
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 108
atgcgatttt aagaactggc tcattatacc agtcaggacg ttgggaagaa aaatctacgt        60

<210> SEQ ID NO 109
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 109
taataaaacg aactaacgga acaacattat tacaggtaga agattcatc agttgagatt        60

<210> SEQ ID NO 110
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 110
taggaatacc acattcaact aatgcagata cataacgcca aaaggaatta cgaggcatag        60

<210> SEQ ID NO 111
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 111
taagagcaac actatcataa ccctcgttta ccagacgacg ataaaaacca aaatagcgag        60

<210> SEQ ID NO 112
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 112
aggcttttgc aaaagaagtt ttgccagagg gggtaatagt aaaatgttta gactggatag        60

<210> SEQ ID NO 113
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 113
cgtccaatac tgcggaatcg tcataaatat tcattgaatc ccctcaaat gctttaaaca        60

<210> SEQ ID NO 114

<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 114
gttcagaaaa cgagaatgac cataaatcaa aaatcaggtc tttaccctga ctattatagt    60

<210> SEQ ID NO 115
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 115
cagaagcaaa gcggattgca tcaaaaagat taagaggaag cccgaaagac ttcaaatatc    60

<210> SEQ ID NO 116
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 116
gcgttttaat tcgagcttca aagcgaacca gaccggaagc aaactccaac aggtcaggat    60

<210> SEQ ID NO 117
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 117
tagagagtac ctttaattgc tccttttgat aagaggtcat ttttgcggat ggcttagagc    60

<210> SEQ ID NO 118
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 118
ttaattgctg aatataatgc tgtagctcaa catgttttaa atatgcaact aaagtacggt    60

<210> SEQ ID NO 119
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 119
gtctggaagt ttcattccat ataacagttg attcccaatt ctgcgaacga gtagatttag    60

<210> SEQ ID NO 120
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 120
tttgaccatt agatacattt cgcaaatggt caataacctg tttagctata ttttcatttg    60

<210> SEQ ID NO 121
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 121
gggcgcgagc tgaaaaggtg gcatcaattc tactaatagt agtagcatt    49

<210> SEQ ID NO 122
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 122
ctactaatag tagtagcatt aacatccaat aaatcataca    40

<210> SEQ ID NO 123
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 123
aacatccaat aaatcataca ggcaaggcaa agaattagca aaattaagca ataaagcctc    60

<210> SEQ ID NO 124
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 124
tctgtccatc acgcaaatta accgttgtag caatacttct tgattagta ataacatcac    60

<210> SEQ ID NO 125
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 125
attcgacaac tcgtattaaa tcctttgccc gaacgttatt aattttaaaa gtttgagtaa    60

<210> SEQ ID NO 126
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 126
gggcgcgagc tgaaaaggtg gcatcaattc tactaatagt agtagcatt    49

<210> SEQ ID NO 127
<211> LENGTH: 60
<212> TYPE: DNA

<213> ORGANISM: Artificial Sequence
<220> FEATURE:
<223> OTHER INFORMATION: Synthetic Oligonucleotide

<400> SEQUENCE: 127
caatacttct tgattagta ataacatcac attcgacaac tcgtattaaa tcctttgccc    60

<210> SEQ ID NO 128
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 128
caatacttct tgattagta ataacatcac attcgacaac tcgtattaaa    50

<210> SEQ ID NO 129
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 129
caatacttct tgattagta ataacatcac attcgacaac tcgta    45

<210> SEQ ID NO 130
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 130
caatacttct tgattagta ataacatcac attcgacaac    40

<210> SEQ ID NO 131
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 131
caatacttct tgattagta ataacatcac tcaaccgatt gagggaggga aggtaaatat    60

<210> SEQ ID NO 132
<211> LENGTH: 50
<212> TYPE: DNA
<213> ORGANISM: Artificial Sequence
<220> FEATURE:
<223> OTHER INFORMATION: Synthetic Oligonucleotide

<400> SEQUENCE: 132
caatacttct tgattagta ataacatcac tcaaccgatt gagggaggga    50

<210> SEQ ID NO 133
<211> LENGTH: 45
<212> TYPE: DNA
<213> ORGANISM: Artificial Sequence
<220> FEATURE:
<223> OTHER INFORMATION: Synthetic Oligonucleotide

<400> SEQUENCE: 133
caatacttct tgattagta ataacatcac tcaaccgatt gaggg    45

```
<210> SEQ ID NO 134
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 134
caatacttct ttgattagta ataacatcac tcaaccgatt                            40
```